United States Patent
Small et al.

(10) Patent No.: US 8,334,420 B2
(45) Date of Patent: Dec. 18, 2012

(54) OLEFIN OLIGOMERIZATION CATALYSTS AND METHODS OF USING SAME

(75) Inventors: Brooke L. Small, Kingwood, TX (US); Jeffery C. Gee, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 879 days.

(21) Appl. No.: 12/116,365

(22) Filed: May 7, 2008

(65) Prior Publication Data

US 2008/0207857 A1    Aug. 28, 2008

Related U.S. Application Data

(62) Division of application No. 11/459,795, filed on Jul. 25, 2006, now Pat. No. 7,378,537.

(51) Int. Cl.
C07C 2/32 (2006.01)
C07C 2/08 (2006.01)
C07F 9/28 (2006.01)
B01J 31/22 (2006.01)

(52) U.S. Cl. ........ 585/523; 585/513; 585/514; 585/527; 502/103; 502/121; 502/123

(58) Field of Classification Search ............... 585/513, 585/514, 523, 527; 502/103, 121, 123
See application file for complete search history.

(56) References Cited

U.S. PATENT DOCUMENTS

| | | | |
|---|---|---|---|
| 4,112,007 A | 9/1978 | Sanfilippo et al. | |
| 4,490,481 A | 12/1984 | Boitiaux et al. | |
| 5,198,563 A | 3/1993 | Reagen et al. | |
| 5,260,499 A | 11/1993 | Wu | |
| 5,288,823 A | 2/1994 | Reagan et al. | |
| 5,320,993 A | 6/1994 | Wu | |
| 5,331,104 A | 7/1994 | Reagen et al. | |
| 5,340,785 A | 8/1994 | Reagen et al. | |
| 5,360,879 A | 11/1994 | Reagen et al. | |
| 5,376,612 A | 12/1994 | Reagen et al. | |
| 5,382,738 A | 1/1995 | Reagen et al. | |
| 5,393,719 A | 2/1995 | Pettijohn et al. | |
| 5,399,539 A | 3/1995 | Reagen et al. | |
| 5,414,178 A | 5/1995 | Wu | |
| 5,438,027 A | 8/1995 | Reagen et al. | |
| 5,451,645 A | 9/1995 | Reagen et al. | |
| 5,470,926 A | 11/1995 | Reagen et al. | |
| 5,523,507 A | 6/1996 | Reagen et al. | |
| 5,543,375 A | 8/1996 | Lashier et al. | |
| 5,563,312 A | 10/1996 | Knudsen et al. | |
| 5,763,723 A | 6/1998 | Reagen et al. | |
| 5,786,431 A | 7/1998 | Reagen et al. | |
| 5,814,575 A | 9/1998 | Reagen et al. | |
| 5,856,257 A | 1/1999 | Freeman et al. | |
| 5,859,303 A | 1/1999 | Lashier | |
| 5,919,996 A | 7/1999 | Freeman et al. | |
| 5,955,555 A | 9/1999 | Bennett | |
| 6,103,946 A | 8/2000 | Brookhart, III et al. | |
| 6,133,387 A | 10/2000 | Xu et al. | |
| 6,239,237 B1 | 5/2001 | Xu et al. | |
| 6,291,733 B1 | 9/2001 | Small et al. | |
| 6,300,435 B1 | 10/2001 | Gao et al. | |
| 6,451,939 B1 | 9/2002 | Britovsek et al. | |
| 6,455,648 B1 | 9/2002 | Freeman et al. | |
| 6,458,739 B1 | 10/2002 | Kimberley et al. | |
| 6,489,497 B1 | 12/2002 | Brookhart, III et al. | |
| 6,548,672 B1 | 4/2003 | Gibson et al. | |
| 6,555,633 B1 | 4/2003 | Tanaka et al. | |
| 6,683,187 B2 | 1/2004 | De Boer et al. | |
| 6,689,848 B2 | 2/2004 | Nagy et al. | |
| 6,710,006 B2 | 3/2004 | De Boer et al. | |
| 6,734,130 B2 | 5/2004 | Cheung et al. | |

(Continued)

FOREIGN PATENT DOCUMENTS

| | | |
|---|---|---|
| CN | 1306014 A | 8/2001 |
| CN | 1358772 A | 7/2002 |
| CN | 1651142 A | 8/2005 |
| CN | 1727367 A | 2/2006 |
| CN | 1872416 A | 12/2006 |
| EP | 1907116 A2 | 4/2008 |
| GB | 1186869 | 4/1970 |
| WO | 9837966 A1 | 9/1998 |
| WO | 0069923 A1 | 11/2000 |
| WO | 0110875 A1 | 2/2001 |

(Continued)

OTHER PUBLICATIONS

Bollman, Annette, et al., "Ethylene tetramerization: a new route to produce 1-octene in exceptionally high selectivities," Journal of the American Chemical Society, pp. 14712-14713, 2004, vol. 126.

Carter, Anthea, et al., "High activity ethylene trimerisation catalysts based on diphospine ligands," Chemical Communications, vol. 8, 2002, pp. 858-859.

(Continued)

Primary Examiner — Caixia Lu

(74) Attorney, Agent, or Firm — Conley Rose, P.C.; Rodney B. Carroll; Lynda S. Jolly

(57) ABSTRACT

A metal complex comprising a metal compound complexed to a heteroatomic ligand, the metal complex having Structure X:

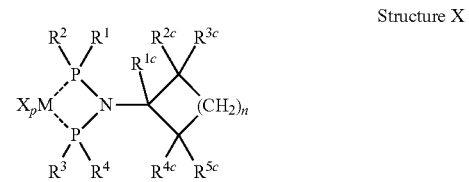

Structure X wherein $R^1$, $R^2$, $R^3$, and $R^4$ are each independently an alkyl group, a cycloalkyl group, a substituted cycloalkyl group, an aromatic group, or a substituted aromatic group, $R^{1c}$, $R^{2c}$, $R^{3c}$, $R^{4c}$, and $R^{5c}$ are each independently hydrogen or an alkyl group, and $MX_p$ comprises a group IVB, VB, or VIB metal. A metal complex comprising a metal compound complexed to a diphosphino aminyl ligand comprising at least two diphosphino aminyl moieties and a linking group linking each aminyl nitrogen atom of the diphosphino aminyl moieties.

21 Claims, No Drawings

U.S. PATENT DOCUMENTS

| | | | |
|---|---|---|---|
| 6,740,715 | B2 | 5/2004 | Brookhart, III et al. |
| 6,841,693 | B1 | 1/2005 | Watanabe et al. |
| 6,911,505 | B2 | 6/2005 | Small |
| 6,911,506 | B2 | 6/2005 | Small et al. |
| 6,916,892 | B2 | 7/2005 | Tharappel et al. |
| 7,001,964 | B2 | 2/2006 | Small |
| 7,037,988 | B2 | 5/2006 | De Boer et al. |
| 7,045,632 | B2 | 5/2006 | Small |
| 7,049,442 | B2 | 5/2006 | De Boer et al. |
| 7,053,020 | B2 | 5/2006 | De Boer et al. |
| 7,053,259 | B2 | 5/2006 | Culver et al. |
| 7,129,304 | B1 | 10/2006 | Small et al. |
| 7,157,612 | B2 | 1/2007 | Ewert et al. |
| 7,179,871 | B2 | 2/2007 | De Boer et al. |
| 7,223,893 | B2 | 5/2007 | Small et al. |
| 7,238,764 | B2 | 7/2007 | De Boer et al. |
| 7,268,096 | B2 | 9/2007 | Small et al. |
| 7,271,121 | B2 | 9/2007 | Small et al. |
| 7,285,607 | B2 | 10/2007 | Blann et al. |
| 7,297,806 | B2 | 11/2007 | Brookhart, III et al. |
| 7,297,832 | B2 * | 11/2007 | Blann et al. .................. 585/527 |
| 7,378,537 | B2 | 5/2008 | Small et al. |
| 7,384,886 | B2 | 6/2008 | Knudsen et al. |
| 7,442,819 | B2 | 10/2008 | Ionkin et al. |
| 7,456,284 | B2 | 11/2008 | Small |
| 7,820,581 | B2 | 10/2010 | Knudsen et al. |
| 2004/0122271 | A1 | 6/2004 | Van Zon et al. |
| 2005/0187098 | A1 | 8/2005 | Knudsen et al. |
| 2007/0043181 | A1 | 2/2007 | Knudsen et al. |
| 2007/0112150 | A1 | 5/2007 | Small et al. |
| 2007/0232481 | A1 | 10/2007 | Zhang et al. |
| 2008/0177122 | A1 | 7/2008 | Knudsen et al. |
| 2008/0207857 | A1 | 8/2008 | Small et al. |

FOREIGN PATENT DOCUMENTS

| | | | |
|---|---|---|---|
| WO | 0110876 A1 | 2/2001 | |
| WO | 0158874 A1 | 8/2001 | |
| WO | 0200339 A2 | 1/2002 | |
| WO | 0204119 A1 | 1/2002 | |
| WO | 0228805 A2 | 4/2002 | |
| WO | 03011876 A1 | 2/2003 | |
| WO | 2004026795 A2 | 4/2004 | |
| WO | 2004029011 A1 | 4/2004 | |
| WO | 2004037415 A2 | 5/2004 | |
| WO | 2004043887 A2 | 5/2004 | |
| WO | 2004056477 A1 | 7/2004 | |
| WO | 2004056478 A1 | 7/2004 | |
| WO | 2004056479 A1 | 7/2004 | |
| WO | 2004056480 A1 | 7/2004 | |
| WO | 2004058480 A1 | 7/2004 | |
| WO | WO 2004/056478 | * | 7/2004 |
| WO | 2005123633 A1 | 12/2005 | |
| WO | 2005123884 A2 | 12/2005 | |
| WO | WO 2005/123633 | * | 12/2005 |
| WO | 2006108803 A1 | 10/2006 | |
| WO | 2007015742 A2 | 2/2007 | |
| WO | 2007057455 A1 | 5/2007 | |
| WO | 2007057458 A1 | 5/2007 | |
| WO | 2008014139 A2 | 1/2008 | |
| WO | 2008014139 A3 | 1/2008 | |

OTHER PUBLICATIONS

Dixon, John T., et al., "Advances in selective ethylene trimerisation—a critical overview," Journal of Organometallic Chemistry, vol. 689, 2004, pp. 3641-3668.

Foreign communication from a related counterpart application—Invitation to Pay Additional Fees, PCT/US2007/073606, Nov. 19, 2007, 12 pgs.

Foreign communication from a related counterpart application—Notification of Transmittal of the International Search Report and Written Opinion of the International Searching Authority, PCT/US2007/073606, Feb. 13, 2008, 20 pgs.

Jabri, Amir, et al., "Isolation of a cationic chromium(II) species in a catalytic system for ethylene tri- and tetramerization," 2006, pp. 715-718, vol. 25, No. 3, Organometallics.

Jiang, Tao, et al., "Highly selective diphoshinoamine/Cr(III) catalysts for ethylene tetramerization," Chinese Chemical Letters, 2006, pp. 358-360, vol. 17, No. 3.

Jiang, Tao, et al., "Preparation of 1-octene by the selective tetramerization of ethylene," Journal of Molecular Catalysis A: Chemical, 2006, pp. 161-165, vol. 259, ScienceDirect.

Kuhlmann, Sven, et al., "N-substituted diphosphinoamines: toward rational ligand design for the efficient tetramerization of ethylene," Journal of Catalysis, 2007, vol. 245, pp. 279-284, ScienceDirect.

Luo, He-Kuan, et al., "The effect of halide and the coordination geometry of chromium center in homogeneous catalyst system for ethylene trimerization," Journal of Molecular Catalysis, A: Chemical, Elsevier B.V. vol. 221, 2004, pp. 9-17.

Tobisch, Sven, et al., "Catalytic oligomerization of ethylene to higher linear a-olefins promoted by the cationic group 4 [(n5-Cp-(CMe2-bridge)-Ph)MII(ethylene)2]+(M=Ti, Zr, Hf) active catalysts: a density functional investigation of the influence of the metal on the catalytic activity and selectivity," Journal of the American Chemical Society, vol. 126, 2004, pp. 9059-9071.

Tobisch, Sven, et al., "Catalytic oligomerization of ethylene to higher linear a-olefins promoted by cationic group 4 cyclopentadienyl-arene active catalysts: a DFT investigation exploring the influence of electronic factors on the catalytic properties by modification of the hemilabile arene functionality," Organometallics, vol. 23, 2004, pp. 4077-4088.

Britovsek, George J. P., et al., "Oligomerisation of ethylene by bis(imino)pyridyliron and -cobalt complexes," Chem. Eur. J., 2000, pp. 2221-2231, vol. 6, No. 12. Wiley-VCH Verlag GmbH, Weinheim.

Small, Brooke L, et al., "Highly active iron and cobalt catalysts for the polymerization of ethylene," Journal of the American Chemical Society, 1998, pp. 4049-4050 plus cover page, vol. 120, No. 16, American Chemical Society.

Small, Brooke L, et al., "Iron Catalysts for the Head-to-Head Dimerization of a-Olefins and Mechanistic Implications for the Production of Linear a-Olefins," Organometallics—American Chemical Society, Nov. 22, 2001, pp. 5738-5744, vol. 20.

Small, Brooke L., et al., "Iron-based catalysts with exceptionally high activities and selectivities for oligomerization of ethylene to linear a-olefins," Journal of the American Chemical Society, 1998, pp. 7143-7144 plus cover page, vol. 120, No. 28, American Chemical Society.

Small, Brooke L., et al., "Polymerization of propylene by a new generation of iron catalysts: mechanisms of chain initiation, propagation, and termination," Macromolecules, 1999, pp. 2120-2130, vol. 32, No. 7, American Chemical Society.

Foreign communication from a related counterpart application, Examination Report, Application No. GCC/P/2007/8774 dated Nov. 2, 2010, 15 pages.

Foreign communication from a related counterpart application—Office Action, CN 200780031316.5, Oct. 10, 2011, 6 pages.

Foreign communication from a related counterpart application—Office Action, CN 200780031316.5, Aug. 3, 2012, 7 pages.

Foreign communication from a related counterpart application, EP Examination Report, Application No. 07812978.0 dated Aug. 31, 2009, 3 pages.

Foreign communication from a related counterpart application, EP Examination Report, Application No. 07812978.0 dated Oct. 19, 2010, 4 pages.

Foreign communication from a related counterpart application, EP Examination Report, Application No. 07812978.0 dated May 3, 2012, 3 pages.

Foreign communication from a related counterpart application, EP Search Report, Application No. 10192303.5 dated Jan. 27, 2011, 14 pages.

Foreign communication from a related counterpart application, EP Examination Report, Application No. 10192303.5 dated May 3, 2012, 4 pages.

Majoumo-Mbe, Felicite, et al., "Oligodentate P, N ligands: N,N,N',N'-tetrakis(diphenylphosphanyl)-1,3-diaminobenzene complexes of rhodium, nickel and palladium", Dalton Transactions, vol. 20, pp. 3326-3330, 2005, XP002457473.

Foreign communication from a related counterpart application, EP Search Report, Application No. 10192305.0, dated Jan. 20, 2011, 7 pages.

* cited by examiner

OLEFIN OLIGOMERIZATION CATALYSTS AND METHODS OF USING SAME

CROSS-REFERENCE TO RELATED APPLICATIONS

This is a Divisional Application of U.S. patent application Ser. No. 11/459,795, filed Jul. 25, 2006 and published as US 2008/0027188 A1, and entitled "Olefin Oligomerization Catalysts and Methods of Using Same," which is hereby incorporated herein by reference in its entirety for all purposes.

FIELD OF THE INVENTION

The present invention relates to catalysts and catalyst systems for producing an olefin oligomer. The present invention also relates to the preparation of catalyst systems for use in a process for producing an olefin oligomer. More particularly, the present invention relates to olefin oligomerization catalyst systems for use in a process for producing an alpha-olefin oligomer comprising 1-hexene, 1-octene, or both from ethylene.

BACKGROUND OF THE INVENTION

Olefin oligomerization catalysts and catalyst systems are known in the art, but sometimes lack selectivity to a desired product and also have a low product yield. Enhancements in preparation methods for olefin oligomerization catalysts and catalyst systems to improve productivity and selectivity to the desired product can reduce catalyst cost and improve process economics.

SUMMARY OF THE INVENTION

Disclosed herein is a metal complex comprising a metal compound complexed to a heteroatomic ligand, the metal complex having Structure X:

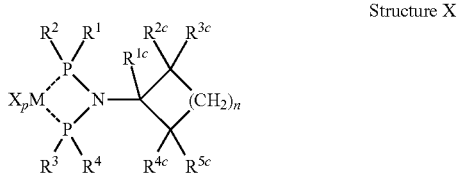

Structure X wherein $R^1$, $R^2$, $R^3$, and $R^4$ are each independently an alkyl group, a cycloalkyl group, a substituted cycloalkyl group, an aromatic group, or a substituted aromatic group, $R^{1c}$, $R^{2c}$, $R^{3c}$, $R^{4c}$, and $R^{5c}$ are each independently hydrogen or an alkyl group, and $MX_p$ comprises a group IVB, VB, or VIB metal.

Further disclosed herein is a metal complex comprising a metal compound complexed to a diphosphino aminyl ligand comprising at least two diphosphino aminyl moieties and a linking group linking each aminyl nitrogen atom of the diphosphino aminyl moieties.

Also disclosed herein is an oligomerization process comprising contacting an olefin, a metal complex, and a cocatalyst, and forming an olefin oligomer product; wherein the metal complex comprises a metal compound complexed to a diphosphino aminyl ligand comprising at least two diphosphino aminyl moieties and a linking group linking the aminyl nitrogen atoms of the diphosphino aminyl moieties.

Also disclosed herein is an oligomerization process comprising contacting an olefin, a metal complex, a cocatalyst, and hydrogen, and forming an olefin oligomer product; wherein the metal complex comprises a metal compound complexed to a diphosphino aminyl ligand comprising a diphosphino aminyl moiety.

Also disclosed herein is a process for reducing an amount of polymer produced in an olefin production process comprising contacting an olefin, a diphosphino aminyl ligand metal complex, a cocatalyst, and hydrogen, providing an olefin production process parameter selected from the group consisting of i) a concentration of diphosphino aminyl complexed metal compound greater than or equal to $2 \times 10^{-5}$ equivalents/liter, ii) a cocatalyst metal to catalyst metal molar ratio greater than or equal to 400:1, iii) a diphosphino aminyl moiety to catalyst metal molar ratio greater than or equal to 2:1, iv) a hydrogen partial pressure ranging from 1 psi (6.9 kPa) to 40 psi (275 kPa), or any combination of i, ii, iii, and iv thereof, and forming an olefin oligomer product.

Also disclosed herein is a catalyst system comprising a metal compound, a ligand comprising a diphosphino aminyl moiety, and a cocatalyst; and having a diphosphino aminyl moiety to metal of the metal compound molar ratio greater than 1.8:1 and a cocatalyst metal to metal of the metal compound molar ratio greater than 200:1.

DETAILED DESCRIPTION OF THE PREFERRED EMBODIMENTS

Disclosed herein are catalyst and catalyst systems comprising a catalyst and a cocatalyst. The catalyst may be a metal complex comprising a metal compound complexed to a heteroatomic ligand. Additional details of the heteroatomic ligand, metal compound, catalyst, cocatalyst, and catalyst system are disclosed herein. Further disclosed herein are methods of using the catalysts and/or catalyst systems for oligomerization of an olefin. The olefin oligomerization catalyst and/or catalyst systems may be used to oligomerize an olefin such as ethylene to 1-hexene, 1-octene or combinations thereof and may display desirable properties such as enhanced productivity and selectivity.

For purposes of this application, a "hydrocarbyl group" has the definition specified by IUPAC: a univalent group formed by removing a hydrogen atom from a hydrocarbon (i.e. a group containing only carbon and hydrogen). A hydrocarbyl group can include the term "alkyl" or "alkyl group." A hydrocarbyl group can include rings, ring systems, aromatic rings, and aromatic ring systems which contain only carbon and hydrogen. Similarly, a "hydrocarbylene group" refers to a group formed by removing two hydrogen atoms from a hydrocarbon and a "hydrocarbon group" refers to a generalized group formed by removing one or more hydrogen atoms from a hydrocarbon.

For purposes of this application, an "organyl group" has the definition specified by IUPAC: an organic substituent group, regardless of functional type, having one free valence at a carbon atom. Thus, an organyl group can contain organic functional group(s) and/or atom(s) other than carbon and hydrogen (i.e. an organic group that can comprise functional groups and/or atoms in addition to carbon and hydrogen). For example, non-limiting examples of atoms other than carbon and hydrogen include halogens, oxygen, nitrogen, and phosphorus, among others. Non-limiting examples of functional groups include ethers, aldehydes, ketones, esters, sulfides, amines, and phosphines, among others. Included in the organyl group definition are heteroatom containing rings, heteroatom containing ring systems, heteroaromatic rings, and heteroaromatic ring systems. Finally, it should be noted that the organyl group definition includes the organyl group consisting of inert functional groups, and the hydrocarbyl group as a members. Similarly, an "organylene group" refers to a organic group, regardless of functional type, formed by removing two hydrogen atoms from one or two carbon atoms of an organic compound and an "organic group" refers to a generalized organic group formed by removing one or more hydrogen atoms from one or more carbon atoms of an organic compound.

For the purposes of this application, the term or variations of the term "organyl group consisting of inert functional groups" refers to an organyl group wherein the organic functional group(s) and/or atom(s) other than carbon and hydrogen present in the functional group are restricted to those functional group(s) and/or atom(s) other than carbon and hydrogen which do not complex with a metal compound and/or are inert under the process conditions defined herein. Thus, the term or variation of the term "organyl groups consisting of inert functional groups" further defines the particular organyl groups that can be present within the organyl group consisting of inert functional groups. Additionally, the term "organyl group consisting of inert functional groups" can refer to the presence of one or more inert functional groups within the organyl group. The term or variation of the term "organyl group consisting of inert functional group" definition includes the hydrocarbyl group as a member. Similarly, an "organylene group consisting of inert functional groups" refers to an organic group formed by removing two hydrogen atoms from one or two carbon atoms of an organic compound consisting of inert functional groups and an "organic group consisting of inert functional group" refers to a generalized organic group consisting of inert functional groups formed by removing one or more hydrogen atoms from one or more carbon atoms of an organic compound consisting of inert functional groups.

For purposes of this application, an "inert functional group" is a group which does not substantially interfere with the process described herein in which the material having an inert functional group takes part and/or does not complex with the metal compound of the metal complex. The term "does not complex with the metal compound" can include groups that could complex with a metal compound but in particular molecules described herein cannot complex with a metal compound due to its positional relationship within a ligand. For example, while an ether group can complex with a metal compound, an ether group located at a para position of a substituted phenyl phosphino aminyl group is an inert functional group because a single metal compound cannot complex with both the para ether group and diphosphino aminyl ligand within the same metal complex molecule. Thus, the inertness of a particular functional group is not only related to its functional group's inherent inability to complex the metal compound but can also be related to the functional group's position within the metal complex. Non-limiting examples of inert functional groups which due not substantially interfere with processes described herein can include halo (fluoro, chloro, bromo and iodo), ethers (alkoxy group or etheryl group), sulfides (sulfidyl group), and/or hydrocarbyl groups among others.

The term or variation of the terms an "oligomerized product having X carbon atoms" and "$C_X$ oligomer product," wherein X can be any positive non-zero integer, refers to materials produced by monomer oligomerization which have X carbon atoms. Thus, the term oligomerized product having X carbon atoms excludes materials having X carbon atoms which were not produced by the olefin oligomerization (e.g. solvent). These terms may also include other descriptive words (e.g. olefin, liquid, and mixture, among others) without detracting from the essence of the term referring to materials having X carbon atoms, produced by monomer oligomerization, and fitting the additional descriptive terms.

In an embodiment, the catalyst comprises a metal compound complexed to a heteroatomic ligand. In an aspect the heteroatomic ligand comprises a moiety characterized by having a P—N—P (phosphorus-nitrogen-phosphorus) linkage. The moiety having the P—N—P linkage may hereafter be referred to a PNP moiety or as a diphosphino aminyl moiety. The heteroatomic ligand comprising the diphosphino aminyl moiety may be referred to as a PNP ligand or as a diphosphino aminyl ligand.

In an embodiment, the heteroatomic ligand comprises a diphosphino aminyl moiety having the Structure 1:

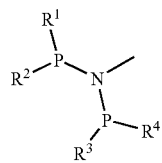

Structure 1 wherein $R^1$, $R^2$, $R^3$, and $R^4$ can be any group described herein and the undesignated aminyl nitrogen valence represents the remainder of the heteroatomic ligand. In an embodiment, $R^1$, $R^2$, $R^3$, and $R^4$ can each be different. In some embodiments, $R^1$, $R^2$, $R^3$, and $R^4$ can be the same. In other embodiments, $R^1$ and $R^2$ can be the same and $R^3$ and $R^4$ can be the same but different from $R^1$ and $R^2$. In yet other embodiments, $R^1$ and $R^3$ can be the same and $R^2$ and $R^4$ can be the same but different from $R^1$ and $R^3$.

In an embodiment, $R^1$, $R^2$, $R^3$, and $R^4$ may each be independently selected from the group consisting of an organyl group, an organyl group consisting of inert functional groups, and a hydrocarbyl group. In some embodiments, $R^1$, $R^2$, $R^3$, and $R^4$ may each be independently selected from the group consisting of an organyl group consisting of inert functional groups, and a hydrocarbyl group. In other embodiments, $R^1$, $R^2$, $R^3$, and $R^4$ may each be independently an organyl group; alternatively, an organyl group consisting of inert functional groups; or alternatively, a hydrocarbyl group. In further embodiments, two or more of $R^1$, $R^2$, $R^3$, and $R^4$ may be joined to form a ring or a ring system.

In some embodiments, $R^1$, $R^2$, $R^3$, and $R^4$ may each be independently selected from the group consisting of an alkyl group, a cycloalkyl group, a substituted cycloalkyl group, an aromatic group, a substituted aromatic group, a heteroaromatic group and a substituted heteroaromatic group. In other embodiments, the $R^1$, $R^2$, $R^3$, and $R^4$ may each independently be an alkyl group, a cycloalkyl group, a substituted cycloalkyl group, an aromatic group, or a substituted aromatic group. In yet other embodiments, the $R^1$, $R^2$, $R^3$, and $R^4$ may each independently be an alkyl group; alternatively, a cycloalkyl group; alternatively, a substituted cycloalkyl group; alternatively, an aromatic group; alternatively, a substituted aromatic group; alternatively, a heteroaromatic group; or alternatively, a substituted heteroaromatic group.

In an embodiment, $R^1$, $R^2$, $R^3$, and $R^4$ can each be independently selected from the group consisting of methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,2-diethyl-1-propyl), n-hexyl (1-hexyl)cyclopentyl, substituted cyclopentyl cyclohexyl, a substituted cyclohexyl, benzyl, substituted benzyl, phenyl, a substituted phenyl, 4-phenyl-phenyl (4-biphenyl) substituted 4-phenyl-phenyl (substituted biphenyl), 2-naphthyl, substituted 2-naphthyl, anthracenyl, substituted anthracenyl pyridinyl, substituted pyridinyl, tetrahydrofuranyl, and a substituted tetrahydrofuranyl group. In some embodiments, $R^1$, $R^2$, $R^3$, and $R^4$ can each be independently selected from the group consisting of methyl, ethyl, isopropyl (2-propyl), tert-butyl (2-methyl-2-propyl), neo-pentyl (2,2-dimethyl-1-propyl), benzyl, substituted benzyl, phenyl, and a substituted phenyl group. Alternatively, $R^1$, $R^2$, $R^3$, and $R^4$ may each independently be a phenyl group or a substituted phenyl group. In some embodiments, $R^1$, $R^2$, $R^3$, and $R^4$ may each independently be a phenyl group; or alternatively, a substituted phenyl group.

In an aspect, the substituents of the substituted cycloalkyl, aromatic, heteroaromatic, phenyl, 4-phenyl-phenyl (4-biphenyl), 2-naphthyl, anthracenyl, pyridinyl, or tetrahydrofuranyl embodiments of $R^1$, $R^2$, $R^3$, and $R^4$ may be a hydrocarbyl group, an organyl group, an organyl group consisting of inert functional groups, or an inert functional group. In an embodiment, the cycloalkyl, aromatic, heteroaromatic, phenyl, 4-phenyl-phenyl (4-biphenyl), 2-naphthyl, anthracenyl, pyridinyl, or tetrahydrofuranyl substituents can be an alkyl group or an inert functional group. In some embodiments, the inert functional group can be a halogen, an etheryl group, or a sulfidyl group. In other embodiments, the cycloalkyl, aromatic, heteroaromatic, phenyl, 4-phenyl-phenyl (4-biphenyl), 2-naphthyl, anthracenyl, pyridinyl, or tetrahydrofuranyl substituents can be an alkyl group, an etheryl group, or a halogen. In yet other embodiments, the cycloalkyl, aromatic, heteroaromatic, phenyl, 4-phenyl-phenyl (4-biphenyl), 2-naphthyl, anthracenyl, pyridinyl, or tetrahydrofuranyl substituents can be an alkyl group; alternatively, an etheryl group; or alternatively, a halogen.

In an embodiment, alkyl substituents of the substituted cycloalkyl, aromatic, heteroaromatic, phenyl, biphenyl, naphthyl, anthracenyl, pyridinyl, or tetrahydrofuranyl embodiments of $R^1$, $R^2$, $R^3$, and $R^4$ can have from 1 to 10 carbon atoms; alternatively, from 1 to 6 carbon atoms; or alternatively, from 1 to 4 carbon atoms. In an embodiment, the alkyl substituent(s) of the substituted cycloalkyl, aromatic, heteroaromatic, phenyl, 4-phenyl-phenyl (4-biphenyl), naphthyl, anthracenyl, pyridinyl, or tetrahydrofuranyl embodiments of $R^1$, $R^2$, $R^3$, and $R^4$ can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,2-dimethyl-1-propyl), or n-hexyl (1-hexyl) group. In some embodiments, the alkyl substituent(s) of the substituted cycloalkyl, aromatic, heteroaromatic, phenyl, 4-phenyl-phenyl (4-biphenyl), naphthyl, anthracenyl, pyridinyl, or tetrahydrofuranyl embodiments of $R^1$, $R^2$, $R^3$, and $R^4$ can be a methyl group; alternatively, an ethyl group; alternatively, an isopropyl group (2-propyl group); alternatively, a tert-butyl group (2-methyl-2-propyl group); or alternatively, a neo-pentyl group (2,2-dimethyl-1-propyl group).

In an embodiment, an etheryl substituent(s) of the substituted cycloalkyl, aromatic, heteroaromatic, phenyl, biphenyl, naphthyl, anthracenyl, pyridinyl, or tetrahydrofuranyl embodiments of $R^1$, $R^2$, $R^3$, and $R^4$ can be a methoxy, ethoxy, n-propoxy (1-propoxy), isopropoxy (2-propoxy), n-butoxy (1-butoxy), sec-butoxy (2-butoxy), isobutoxy (2-methyl-1-propoxy), tert-butoxy (2-methyl-2-propoxy), n-pentoxy (1-pentoxy), 2-pentoxy, 3-pentoxy, 2-methyl-1-butoxy, tert-pentoxy (2-methyl-2-butoxy), 3-methyl-1-butoxy, 3-methyl-2-butoxy, or neo-pentoxy (2,2-dimethyl-1-propoxy) group. In some embodiments, the etheryl substituent(s) of the substituted cycloalkyl, aromatic, heteroaromatic, phenyl, biphenyl, naphthyl, anthracenyl, pyridinyl, or tetrahydrofuranyl embodiments of $R^1$, $R^2$, $R^3$, and $R^4$ can be a methoxy group; alternatively, an ethoxy group; alternatively, an isopropoxy group (2-propoxy group); or alternatively, a tert-butoxy group (2-methyl-2-propoxy group).

In an embodiment, a halogen substituent(s) of the substituted cycloalkyl, aromatic, heteroaromatic, phenyl, 4-phenyl-phenyl (4-biphenyl), naphthyl, anthracenyl, pyridinyl, or tetrahydrofuranyl embodiments of $R^1$, $R^2$, $R^3$, and $R^4$ can be fluorine, chlorine, bromine, or iodine. In other embodiments, the halogen substituent of the substituted cycloalkyl, aromatic, heteroaromatic, phenyl, 4-phenyl-phenyl (4-biphenyl), naphthyl, anthracenyl, pyridinyl, or tetrahydrofuranyl embodiments of $R^1$, $R^2$, $R^3$, and $R^4$ can be fluorine; alternatively, chlorine; alternatively, bromine; or alternatively, iodine.

In some embodiments, one or more of $R^1$, $R^2$, $R^3$, and $R^4$ can be a phenyl group or a substituted phenyl group. When one or more of $R^1$, $R^2$, $R^3$, and $R^4$ is a phenyl group or a substituted phenyl group $R^1$, $R^2$, $R^3$, and $R^4$ can have Structure 2:

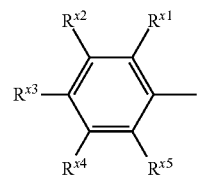

Structure 2 wherein $R^{x1}$, $R^{x2}$, $R^{x3}$, $R^{x4}$, and $R^{x5}$ can each separately be hydrogen, an alkyl group, an etheryl group, or a halogen atom. The potential alkyl groups, alkoxy groups, and halogen atom substituents are described herein and can be utilized in any combination within Structure 2. In some embodiments, $R^{x1}$ is an alkyl group and $R^{x2}$, $R^{x3}$, $R^{x4}$, and $R^{x5}$ are hydrogen; or alternatively, $R^{x3}$ is an alkyl group and $R^{x1}$, $R^{x2}$, $R^{x4}$, and $R^{x5}$ are hydrogen. In other embodiments, $R^{x3}$ is an alkoxy group and $R^{x1}$, $R^{x2}$, $R^{x4}$, and $R^{x5}$ are hydrogen. In yet other embodiments, $R^{x4}$ is an alkoxy group and $R^{x1}$, $R^{x2}$, $R^{x3}$, and $R^{x5}$ are hydrogen. In further embodiments, $R^{x1}$, $R^{x2}$, $R^{x3}$, $R^{x4}$, and $R^{x5}$ are hydrogen.

When the diphosphino aminyl moiety comprises more that one phenyl group, the substituents of one phenyl group can be independent of the substituents of one or more of the other phenyl groups. In this scenario, the substituent designations of each phenyl group can be represented by replacing the x within R group designations of Structure 2 with the number of the diphosphino aminyl moiety R group in Structure 1 which it represents. For example, if the $R^1$ group of the diphosphino aminyl moiety having Structure 1 is a phenyl group (or a substituted phenyl group), the designations of the $R^1$ phenyl group having Structure 2 would be represented by the designations $R^{11}$, $R^{12}$, $R^{13}$, $R^{14}$, and $R^{15}$. Likewise, the designations of a $R^3$ phenyl group (or substituted phenyl group) would be represented by the designations $R^{31}$, $R^{32}$, $R^{33}$, $R^{34}$, and $R^{35}$.

In an embodiment, the diphosphino aminyl moiety can have Structure 3:

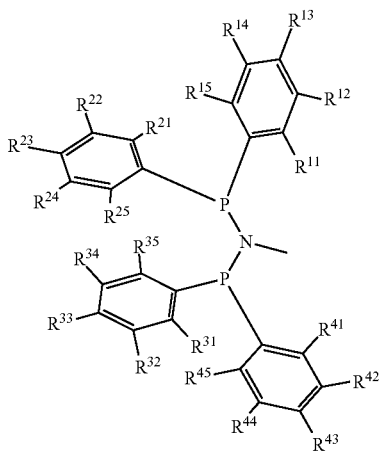

Structure 3 wherein the substituents $R^{11}$, $R^{12}$, $R^{13}$, $R^{14}$, and $R^{15}$, $R^{21}$, $R^{22}$, $R^{23}$, $R^{24}$ and $R^{25}$, $R^{31}$, $R^{32}$, $R^{33}$, $R^{34}$, and $R^{35}$, $R^{41}$, $R^{42}$, $R^{43}$, $R^{44}$, and $R^{45}$ can independently have any combination of substituent(s) described herein and/or have any substituent pattern for the substituted phenyl groups as described herein.

In some diphosphino aminyl moiety embodiments having Structure 3, $R^{11}$, $R^{21}$, $R^{31}$, and $R^{41}$ are alkyl groups and $R^{12}$, $R^{13}$, $R^{14}$, $R^{15}$, $R^{22}$, $R^{23}$, $R^{24}$, $R^{25}$, $R^{32}$, $R^{33}$, $R^{34}$, $R^{35}$, $R^{42}$, $R^{43}$, $R^{44}$, and $R^{45}$ are hydrogen; alternatively, $R^{11}$, $R^{21}$, and $R^{41}$ are alkyl groups and $R^{12}$, $R^{13}$, $R^{14}$, $R^{15}$, $R^{22}$, $R^{23}$, $R^{24}$, $R^{25}$, $R^{31}$, $R^{32}$, $R^{33}$, $R^{34}$, $R^{35}$, $R^{42}$, $R^{43}$, $R^{44}$, and $R^{45}$ are hydrogen; alternatively, $R^{11}$ and $R^{41}$ are alkyl groups and $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{44}$, and $R^{45}$ are hydrogen; alternatively, $R^{11}$ and $R^{21}$, are alkyl groups and $R^{12}$, $R^{13}$, $R^{15}$, $R^{22}$, $R^{23}$, $R^{24}$ $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are hydrogen; or alternatively, $R^{11}$ is an alkyl group and $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are hydrogen. In other diphosphino aminyl moiety embodiments having Structure 3, $R^{13}$, $R^{23}$, $R^{33}$, and $R^{43}$ are alkyl groups and $R^{11}$, $R^{12}$, $R^{14}$, $R^{15}$, $R^{21}$, $R^{22}$, $R^{24}$, $R^{25}$, $R^{31}$, $R^{32}$, $R^{34}$, $R^{35}$, $R^{41}$, $R^{42}$, $R^{44}$, and $R^{45}$ are hydrogen; alternatively, $R^{13}$, $R^{23}$, and $R^{43}$ are alkyl groups and $R^{11}$, $R^{12}$, $R^{14}$, $R^{15}$ $R^{21}$, $R^{22}$, $R^{24}$, $R^{25}$, $R^{31}$, $R^{32}$, $R^{33}$, $R^{34}$, $R^{35}$, $R^{41}$, $R^{42}$, $R^{44}$, and $R^{45}$ are hydrogen; alternatively, $R^{13}$ and $R^{43}$ are alkyl groups and $R^{11}$, $R^{12}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{44}$, and $R^{45}$ are hydrogen; alternatively, $R^{13}$, and $R^{23}$ are alkyl groups and $R^{11}$, $R^{12}$, $R^{14}$, $R^{15}$, $R^{21}$, $R^{22}$, $R^{24}$, $R^{25}$, $R^{31}$, $R^{32}$, $R^{33}$, $R^{34}$, $R^{35}$, $R^{41}$, $R^{42}$, $R^{44}$, and $R^{45}$ are hydrogen; or alternatively, $R^{13}$, is an alkyl group and $R^{11}$, $R^{12}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are hydrogen. In yet other diphosphino aminyl moiety embodiments having Structure 3, $R^{13}$, $R^{23}$, $R^{33}$, and $R^{43}$ are etheryl groups and $R^{11}$, $R^{12}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{44}$, and $R^{45}$ are hydrogen; alternatively, $R^{13}$, $R^{23}$, and $R^{43}$ are etheryl groups and $R^{11}$, $R^{12}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$ $R^{44}$, and $R^{45}$ are hydrogen; alternatively, $R^{13}$ and $R^{43}$ are etheryl groups and $R^{11}$, $R^{12}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{44}$, and $R^{45}$ are hydrogen; alternatively, $R^{13}$ and $R^{23}$ are etheryl groups and $R^{11}$, $R^{12}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are hydrogen; or alternatively, $R^1$ is an etheryl group and $R^{11}$, $R^{12}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are hydrogen. In a further embodiment, $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are hydrogen. The alkyl or etheryl group substituents for substituted phenyl group of the diphosphino aminyl moiety have been described previously and can be applied to the diphosphino aminyl moiety substituent patterns having Structure 3 as described herein.

In a non-limiting embodiment, the diphosphino aminyl moiety or moieties of the diphosphino aminyl ligand can be (methyl$_2$P)$_2$N-(a bis(dimethylphosphino)aminyl group), (ethyl$_2$P)$_2$N-(a bis(diethylphosphino)aminyl group), (isopropyl$_2$P)$_2$N-(a bis(diisopropylphosphino)aminyl group), (tert-butyl$_2$P)$_2$N-(a bis(di-tert-butylphosphino)aminyl group), (neo-pentyl$_2$P)$_2$N-(a bis(dineopentylphosphino) aminyl group), (phenyl$_2$P)$_2$N-(a bis(diphenyl-phosphino) aminyl group) (2-naphthyl$_2$P)$_2$N-(a bis(di-2-naphthylphospino)aminyl group), or (4-biphenyl$_2$P)$_2$N-(a bis (di-4-biphenylphospino)aminyl group). In a non-limiting embodiment, the diphosphino aminyl moiety or moieties of the diphosphino aminyl ligand can be (phenyl$_2$P)$_2$N-(a bis (diphenylphospino)aminyl group).

In some non-limiting embodiments, the diphosphino aminyl moiety or moieties of the diphosphino aminyl ligand can be ((2-methylphenyl)$_2$P)$_2$N-(a bis(di(2-methylphenyl)-phosphino)aminyl group), ((2-ethylphenyl)$_2$P)$_2$N-(a bis(di(2-ethylphenyl)phosphino)aminyl group), ((2-isopropylphenyl)$_2$P)$_2$N-(a bis(di(2-isopropylphenyl)phosphino)aminyl group), ((2-tert-butylphenyl)$_2$P)$_2$N-(a bis(di(2-tert-butylphenyl) phosphino)aminyl group), or ((2-neopentyl-phenyl)$_2$P)$_2$N-(a bis(di(2-neopentylphenyl)phosphino)aminyl group). In other non-limiting embodiments, the diphosphino aminyl moiety or moieties of the diphosphino aminyl ligand can be ((4-methylphenyl)$_2$P)$_2$N-(a bis(di(4-methylphenyl)phosphino) aminyl group), ((4-ethyl-phenyl)$_2$P)$_2$N-(a bis(di(4-ethylphenyl)phosphino)aminyl group), ((4-isopropylphenyl)$_2$P)$_2$N-(a bis(di(4-isopropylphenyl)phosphino)aminyl group), ((4-tert-butylphenyl)$_2$P)$_2$N-(a bis(di(4-tert-butylphenyl)phosphino) aminyl group), or ((4-neopentylphenyl)$_2$P)$_2$N-(a bis(di(4-neopentyl-phenyl)phosphino)aminyl group).

In other non-limiting embodiments, the diphosphino aminyl moiety or moieties of the diphosphino aminyl ligand can be ((3-methoxyphenyl)$_2$P)$_2$N-(a bis(di(3-methoxyphenyl) phosphino)aminyl group), ((4-methoxyphenyl)$_2$P)$_2$N-(a bis (di(4-methoxyphenyl)phosphino)-aminyl group), ((3-ethoxyphenyl)$_2$P)$_2$N-(a bis(di(3-ethoxyphenyl)phosphino)aminyl group), ((4-ethoxyphenyl)$_2$P)$_2$N-(a bis(di(4-ethoxyphenyl) phosphino)aminyl group), ((3-isopropoxy-phenyl)$_2$P)$_2$N-(a bis(di(3-isopropoxyphenyl)phosphino)aminyl group), ((4-isopropoxy-phenyl)$_2$P)$_2$N-(a bis(di(4-isopropoxyphenyl) phosphino)aminyl group), ((3-tert-butoxy-phenyl)$_2$P)$_2$N-(a bis(di(3-tert-butoxyphenyl)phosphino)aminyl group), ((4-tert-butoxy-phenyl)$_2$P)$_2$N-(a bis(di(4-tert-butoxyphenyl) phosphino)aminyl group). In a non-limiting embodiment, the diphosphino aminyl moiety or moieties of the diphosphino aminyl ligand can be ((3-methoxyphenyl)$_2$P)$_2$N-(a bis(di(3-methoxyphenyl)phosphino)aminyl group).

In yet other non-limiting embodiments, the diphosphino aminyl moiety or moieties of the diphosphino aminyl ligand can be ((2-thiophenyl)$_2$P)$_2$N-(a bis(di(2-thiophenyl)phosphino) aminyl group), ((3-thiophenyl)$_2$P)$_2$N-(a bis(di(3-thiophenyl)phosphino) aminyl group), ((3-ethyl-2-thiophenyl)$_2$P)$_2$N-(a bis(di(3-ethyl-2-thiophenyl)phosphino) aminyl group), ((2-ethyl-3-thiophenyl)$_2$P)$_2$N-(a bis(di(2-ethyl-3-thiophenyl)phosphino) aminyl group), ((2-pyridine)$_2$P)$_2$N-(a bis(di(2-pyridinyl)phosphino) aminyl group), ((3-pyridine)₂P)₂N-(a bis(di(3-pyridinyl) phosphino) aminyl group), ((4-pyridine)₂P)₂N-(a bis(di(4-pyridinyl)phosphino) aminyl group), or ((2-ethyl-4-pyridinyl)₂P)₂N-(a bis(di(2-ethyl-4-pyridinyl)phosphino aminyl group). In further non-limiting embodiments, the diphosphino aminyl moiety or moieties of the diphosphino aminyl ligand can be ((2-thiophenyl)₂P)₂N-(a bis(di(2-thiophenyl)phosphino) aminyl group); or alternatively, (2-pyridine)₂P)₂N-(a bis(di(2-pyridinyl)phosphino) aminyl group).

In an embodiment, the diphosphino aminyl ligand can have the formula $R^1R^2P—N(R^5)—PR^3R^4$ wherein the $(R^1R^2P)(PR^3R^4)N—$ represents the diphosphino aminyl moiety and $R^5$ represent the remainder of the diphosphino aminyl ligand. The diphosphino aminyl moieties are described herein and can be utilized in any combination with group $R^5$ as described herein. The diphosphino aminyl ligands disclosed herein may be prepared using procedures known to one skilled in the art and procedures in published literature.

In an aspect, $R^5$ can be a cycloalkyl group or a substituted cycloalkyl group. In an embodiment, $R^5$ can be a cycloalkyl group; or alternatively, a substituted cycloalkyl group. In some embodiments, $R^5$ can be a cyclobutyl group, a substituted cyclobutyl group, a cyclopentyl group, a substituted cyclopentyl group, a cyclohexyl group, a substituted cyclohexyl group, a cycloheptyl group, a substituted cycloheptyl group, a cyclooctyl group, or a substituted cyclooctyl group. In other embodiments, $R^5$ can be a substituted cyclopentyl group, a substituted cyclohexyl group, or a substituted cycloheptyl group. In yet other embodiments, $R^5$ can be a substituted cyclohexyl group. Within the substituted cycloalkyl group embodiments of $R^5$, the cycloalkyl group substituents can be an organyl group, an organyl group consisting of inert functional groups, a hydrocarbyl group, or an inert functional group. In some embodiments, the cycloalkyl group substituents can be an alkyl group. In an embodiment, the substituted cycloalkyl group comprises an alkyl substituent located on a carbon atom adjacent to (i.e. attached to) a carbon atom attached to the aminyl nitrogen atom of the diphosphino aminyl moiety. In some embodiments, the substituted cycloalkyl group comprises only one alkyl substituent located on a carbon atom adjacent to a carbon atom attached to the aminyl nitrogen atom of the diphosphino aminyl moiety. In other embodiments, the substituted cycloalkyl group consists of only one alkyl substituent located on a carbon atom adjacent to the carbon atom attached to an aminyl nitrogen atom of the diphosphino aminyl moiety.

In an embodiment, the alkyl substituents of the substituted cycloalkyl $R^5$ group can have from 1 to 10 carbon atoms; alternatively, from 1 to 6 carbon atoms; or alternatively, from 1 to 4 carbon atoms. In some embodiments, the alkyl substituents of the substituted cycloalkyl $R^5$ group can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,2-dimethyl-1-propyl), or n-hexyl (1-hexyl) group. In other embodiments, the alkyl substituents of the substituted cycloalkyl $R^5$ group can be a methyl, ethyl, n-propyl (1-propyl), n-butyl (1-butyl), isobutyl (2-methyl-1-propyl), n-pentyl (1-pentyl), 2-methyl-1-butyl, 3-methyl-1-butyl, neo-pentyl (2,2-dimethyl-1-propyl), or n-hexyl (1-hexyl) group. In yet other embodiments, the alkyl substituent(s) of the substituted cycloalkyl $R^5$ group can be a methyl group; alternatively, a ethyl group; alternatively, an isopropyl group; or alternatively, a tert-butyl group.

In an embodiment, $R^5$ can be a cyclopentyl group, a 2-methylcyclopentyl group, a cyclohexyl group, a 2-methylcyclohexyl group, a cycloheptyl group, or a 2-methylcycloheptyl group. In some embodiments, $R^5$ can be a cyclopentyl group, a cyclohexyl group, or a cycloheptyl group. In other embodiments, $R^5$ can be a 2-methylcyclopentyl group, a 2-methylcyclohexyl group, or a 2-methylcycloheptyl group. In yet other embodiments, $R^5$ can be a cyclohexyl group; or alternatively, a 2-methylcyclohexyl group.

In an aspect, $R^5$ can have Structure 4:

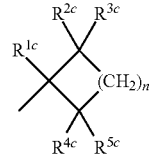

Structure 4 wherein $R^{1c}$, $R^{2c}$, $R^{3c}$, $R^{4c}$, and $R^{5c}$ can independently be hydrogen, a hydrocarbyl group, an organyl group, an organyl group consisting of inert functional groups, or an inert functional group, n can be an integer ranging from 1 to 5, and the undesignated valency is attached to the aminyl nitrogen atom of the diphosphino aminyl group. In an embodiment, n ranges from 2 to 4. In some embodiments, n can be 2; alternatively, 3; or alternatively, 4. In an embodiment, $R^{1c}$, $R^{2c}$, $R^{3c}$, $R^{4c}$, and $R^{5c}$ can independently be hydrogen, or an alkyl group. Within Structure 4, the substituents $R^{1c}$, $R^{2c}$, $R^{3c}$, $R^{4c}$, and $R^{5c}$ can be any substituted cycloalkyl $R^5$ group described herein and/or have any substituent pattern as described herein. In some embodiments, $R^{2c}$ is an alkyl group and $R^{1c}$, $R^{3c}$, $R^{4c}$, and $R^{5c}$ are hydrogen.

In an embodiment, the diphosphino aminyl ligand can have Structure I:

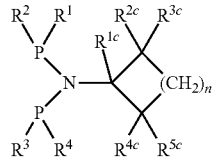

Structure I wherein $R^1$, $R^2$, $R^3$, and $R^4$ can independently be any group as described herein, $R^{1c}$, $R^{2c}$, $R^{3c}$, $R^{4c}$, and $R^{5c}$ can be any cycloalkyl substituent described herein, and/or any cycloalkyl substituent pattern described herein for the $R^5$ group having Structure 4, and n can have any value described herein for the $R^5$ group having Structure 4. In some embodiments, the diphosphino aminyl ligands can have Structure I wherein $R^1$, $R^2$, $R^3$, and $R^4$ can independently be any group as described herein, $R^{1c}$, $R^{2c}$, $R^{3c}$, $R^{4c}$, and $R^{5c}$ can have any substituent pattern comprising an alkyl substituent located on a carbon atom adjacent to the carbon atom attached to an aminyl nitrogen atom of the diphosphino aminyl moiety, and n can have any value described herein for the $R^5$ group having Structure 4. In other embodiments, the diphosphino aminyl ligands can have Structure I wherein $R^1$, $R^2$, $R^3$, and $R^4$ can independently be any group as described herein, $R^{1c}$, $R^{2c}$, $R^{3c}$, $R^{4c}$, and $R^{5c}$ can have any substituent pattern comprising only one alkyl substituent located on a carbon atom adjacent to the carbon atom attached to an aminyl nitrogen atom of the diphosphino aminyl moiety, and n can have any value described herein for the $R^5$ group having Structure 4. In yet other embodiments, the diphosphino aminyl ligands can have Structure I wherein $R^1$, $R^2$, $R^3$, and $R^4$ can independently be any group as described herein, $R^{2c}$ is an alkyl substituent, $R^{1c}$, $R^{3c}$, $R^{4c}$, and $R^{5c}$ are hydrogen, and n can have any value described herein for the $R^5$ group having Structure 4.

In an embodiment, the diphosphino aminyl ligand can have Structure II:

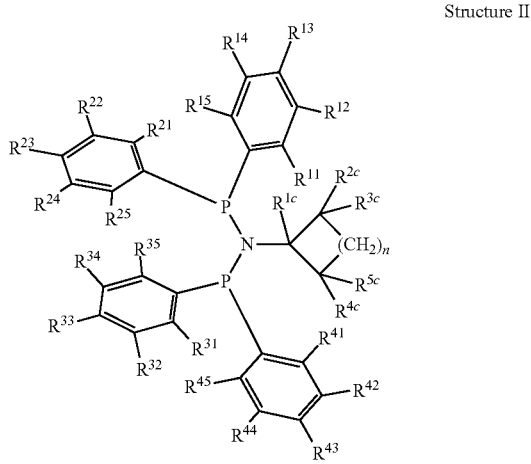

Structure II wherein $R^{11}$, $R^{12}$, $R^{13}$, $R^{14}$, and $R^{15}$, $R^{21}$, $R^{22}$, $R^{23}$, $R^{24}$, and $R^{25}$, $R^{31}$, $R^{32}$, $R^{33}$, $R^{34}$, and $R^{35}$, $R^{41}$, $R^{42}$, $R^{43}$, $R^{44}$, and $R^{45}$ can be any substituent described herein and/or have any substituent pattern described herein for the diphosphino aminyl moiety having Structure 3, $R^{1c}$, $R^{2c}$, $R^{3c}$, $R^{4c}$, and $R^{5c}$ can be any cycloalkyl substituent described herein and/or have any cycloalkyl substituent pattern described herein for the $R^5$ group having Structure 4, and n can have any value described herein for the $R^5$ group having Structure 4.

In some embodiments, the diphosphino aminyl ligands can have Structure II wherein, $R^{11}$, $R^{12}$, $R^{13}$, $R^{14}$, and $R^{15}$, $R^{21}$, $R^{22}$, $R^{23}$, $R^{24}$, and $R^{25}$, $R^{31}$, $R^{32}$, $R^{33}$, $R^{34}$, and $R^{35}$, $R^{41}$, $R^{42}$, $R^{43}$, $R^{44}$, and $R^{45}$ can be any substituent described herein and/or have any substituent pattern described herein for the diphosphino aminyl moiety having Structure 3, $R^{1c}$, $R^{2c}$, $R^{3c}$, $R^{4c}$, and $R^{5c}$ can have any substituent pattern comprising an alkyl substituent located on a carbon atom adjacent to a carbon atom attached to an aminyl nitrogen atom of the diphosphino aminyl moiety, and n can have any value described herein for the $R^5$ group having Structure 4. In other embodiments, the diphosphino aminyl ligands can have Structure II wherein $R^{11}$, $R^{12}$, $R^{13}$, $R^{14}$, $R^{15}$, $R^{21}$, $R^{22}$, $R^{23}$, $R^{24}$, and $R^{25}$, $R^{31}$, $R^{32}$, $R^{33}$, $R^{34}$, and $R^{35}$, $R^{41}$, $R^{42}$, $R^{43}$, $R^{44}$, and $R^{45}$ can be any substituent described herein and/or have any substituent pattern described herein for the diphosphino aminyl moiety having Structure 3, $R^{1c}$, $R^{2c}$, $R^{3c}$, $R^{4c}$, and $R^{5c}$ can have any substituent pattern comprising only one alkyl substituent located on a carbon atom adjacent to the carbon atom attached to an aminyl nitrogen atom of the diphosphino aminyl moiety, and n can have any value described herein for the $R^5$ group having Structure 4. In yet other embodiments, the diphosphino aminyl ligands can have Structure I wherein $R^{11}$, $R^{12}$, $R^{13}$, $R^{14}$, $R^{15}$, $R^{21}$, $R^{22}$, $R^{23}$, $R^{24}$, and $R^{25}$, $R^{31}$, $R^{32}$, $R^{33}$, $R^{34}$, and $R^{35}$, $R^{41}$, $R^{42}$, $R^{43}$, $R^{44}$, and $R^{45}$ can be any substituent described herein and/or have any substituent pattern described herein for the diphosphino aminyl moiety having Structure 3, $R^{2c}$ is an alkyl substituent, $R^{1c}$, $R^{3c}$, $R^{4c}$, and $R^{5c}$ are hydrogen, and n can have any value described herein for the $R^5$ group having Structure 4.

In an embodiment, the diphosphino aminyl ligand can be (methyl$_2$P)$_2$N-(2-methylcyclohexyl), (ethyl$_2$P)$_2$N-(2-methylcyclohexyl), (isopropyl$_2$P)$_2$N-(2-methylcyclohexyl), (tert-butyl$_2$P)$_2$N-(2-methylcyclohexyl), (neopentyl$_2$P)$_2$N-(2-methylcyclohexyl), (phenyl$_2$P)$_2$N-(2-methylcyclohexyl), (2-naphthyl$_2$P)$_2$N-(2-methylcyclohexyl), or (4-biphenyl$_2$P)$_2$N-(2-methylcyclohexyl). In a non-limiting embodiment, the diphosphino aminyl ligand can be (phenyl$_2$P)$_2$N-(2-methylcyclohexyl).

In some non-limiting embodiments, the diphosphino aminyl ligand can be ((2-methylphenyl)$_2$P)$_2$N-(2-methylcyclohexyl), ((2-ethylphenyl)$_2$P)$_2$N-(2-methylcyclohexyl), ((2-isopropylphenyl)$_2$P)$_2$N-(2-methylcyclohexyl), ((2-tert-butylphenyl)$_2$P)$_2$N-(2-methylcyclohexyl), or ((2-neopentylphenyl)$_2$P)$_2$N-(2-methylcyclohexyl). In other non-limiting embodiments, the diphosphino aminyl ligand can be ((4-methylphenyl)$_2$P)$_2$N-(2-methylcyclohexyl), ((4-ethylphenyl)$_2$P)$_2$N-(2-methylcyclohexyl), ((4-isopropylphenyl)$_2$P)$_2$N-(2-methylcyclohexyl), ((4-tert-butylphenyl)$_2$P)$_2$N-(2-methylcyclohexyl), or ((4-neopentylphenyl)$_2$P)$_2$N-(2-methylcyclohexyl). In further embodiments, the diphosphino aminyl ligand can be ((2-methylphenyl)$_2$P)$_2$N-(2-methylcyclohexyl); or alternatively, ((4-methylphenyl)$_2$P)$_2$N-(2-methylcyclohexyl).

In a non-limiting embodiment, the diphosphino aminyl ligand can be ((3-methoxyphenyl)$_2$P)$_2$N-(2-methylcyclohexyl), ((4-methoxyphenyl)$_2$P)$_2$N-(2-methylcyclohexyl), ((3-ethoxyphenyl)$_2$P)$_2$N-(2-methylcyclohexyl), ((4-ethoxyphenyl)$_2$P)$_2$N-(2-methylcyclohexyl), ((3-iso-propoxyphenyl)$_2$P)$_2$N-(2-methylcyclohexyl), ((4-isopropoxyphenyl)$_2$P)$_2$N-(2-methylcyclohexyl), ((3-tert-butoxyphenyl)$_2$P)$_2$N-(2-methylcyclohexyl), or ((4-tert-butoxyphenyl)$_2$P)$_2$N-(2-methylcyclohexyl). In some non-limiting embodiment, the diphosphino aminyl ligand can be ((3-methoxyphenyl)$_2$P)$_2$N-(2-methylcyclohexyl); or alternatively, ((4-methoxyphenyl)$_2$P)$_2$N-(2-methylcyclohexyl).

In a non-limiting embodiment, the diphosphino aminyl ligand can be ((2-thiophenyl)$_2$P)$_2$N-(2-methylcyclohexyl), ((3-thiophenyl)$_2$P)$_2$N-(2-methylcyclohexyl), ((3-ethyl-2-thiophenyl)$_2$P)$_2$N-(2-methylcyclohexyl), ((2-ethyl-3-thiophenyl)$_2$P)$_2$N-(2-methylcyclohexyl), ((2-pyridine)$_2$P)$_2$N-(2-methylcyclohexyl), ((3-pyridine)$_2$P)$_2$N-(2-methylcyclohexyl), ((4-pyridine)$_2$P)$_2$N-(2-methylcyclohexyl), or ((2-ethyl-4-pyridinyl)$_2$P)$_2$N-(2-methylcyclohexyl). In other non-limiting embodiments, the diphosphino aminyl ligand can be ((2-thiophenyl)$_2$P)$_2$N-(2-methylcyclohexyl); or alternatively, (2-pyridine)$_2$P)$_2$N-(2-methylcyclohexyl).

In an embodiment, the diphosphino aminyl ligands can be represented by Structure (I) wherein $R_1$, $R_2$, $R_3$, and $R_4$ are phenyl groups and $R^5$ is a methylcyclohexyl group (Structure III).

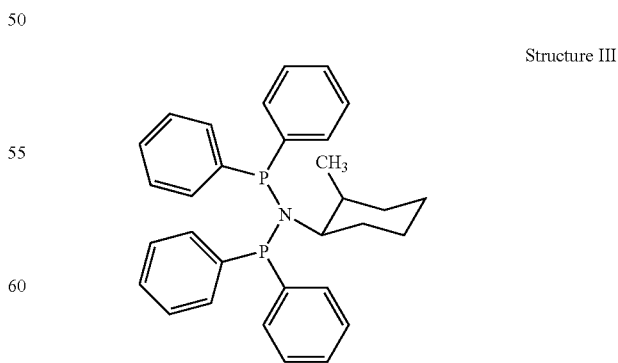

Structure III

In an aspect, the heteroatomic ligand can comprise multiple diphosphino aminyl moieties. In a non-limiting embodiment, the heteroatomic ligand comprises at least 2 diphosphino aminyl moieties; alternatively, from 2 to 5 diphosphino aminyl moieties; or alternatively, from 2 to 3 diphosphino aminyl moieties. In an embodiment, the heteroatomic ligand comprises only 2 diphosphino aminyl moieties. In some embodiments, the heteroatomic ligand comprising multiple diphosphino aminyl moieties further comprises a linking group, L, linking the aminyl nitrogen atoms of the diphosphino aminyl moieties. In some embodiments, the heteroatomic ligand comprises at least 2 diphosphino aminyl moieties (or any other number of diphosphino aminyl moieties described herein) and a linking group linking the aminyl nitrogen atoms of the diphosphino aminyl moieties. In other embodiments, the heteroatomic ligand comprises only 2 diphosphino aminyl moieties and a linking group linking the aminyl nitrogen atoms of the 2 diphosphino aminyl moieties. Hereafter the heteroatomic ligand comprising multiple diphosphino aminyl moieties and a linking group, L, linking the aminyl nitrogen atoms of the diphosphino aminyl moieties can be denoted as $(PNP)_qL$ wherein PNP represent a diphosphino aminyl moiety, q represents the number of PNP moieties present in the heteroatomic ligand and L represents the linking group linking the aminyl nitrogen atoms of the diphosphino aminyl moieties. In an embodiment, q is greater than or equal to 2; alternatively, q ranges from 2 to 5; alternatively, q ranges from 2 to 3; or alternatively, q is exactly 2. The diphosphino aminyl moieties have been described herein and can be used without limitation and/or in any combination within the descriptions of the heteroatomic ligand containing multiple diphosphino aminyl moieties.

In an embodiment, the linking group linking the aminyl nitrogen atoms of the diphosphino aminyl moieties can be an organic group, an organic group consisting of inert functional groups, or a hydrocarbon group. In some embodiments, the linking group linking the aminyl nitrogen atoms of the diphosphino aminyl groups can be an organic group; alternatively, an organic group consisting of inert functional groups; or alternatively a hydrocarbon group. The organic linking group, organic linking group consisting of inert functional group, or hydrocarbon linking group can have from 1 to 50 carbon atoms; alternatively from 2 to 30 carbon atoms; or alternatively, from 2 to 20 carbon atoms.

In an embodiment, the linking group, linking the aminyl nitrogen atoms of the diphosphino aminyl moieties, can be acyclic. In some embodiments, the linking group, linking the aminyl nitrogen atoms of the diphosphino aminyl moieties, can comprise a cyclic group (i.e. a ring). In other embodiments, the linking group, linking the aminyl nitrogen atoms of the diphosphino aminyl moieties, comprises at least one cyclic group; alternatively, at least two cyclic groups; alternatively, from 1 to 5 cyclic groups; alternatively, from 1 to 3 cyclic groups; or alternatively, from 1 to 2 cyclic groups. In further embodiments, the linking group, linking the aminyl nitrogen atoms of the diphosphino aminyl moieties, comprises only one cyclic group; or alternatively, comprises only two cyclic groups.

Generally, with exception to the presence of the groups containing the diphosphino aminyl moieties, the linking group, linking the aminyl nitrogen atoms of the diphosphino aminyl moieties, can comprise an unsubstituted cyclic group(s); or alternatively, can comprise a substituted cyclic group(s) (i.e. have moieties attached to a ring carbon which do not comprise a diphosphino aminyl moiety). In some embodiments wherein the linking group linking the aminyl nitrogen atoms of the diphosphino aminyl moieties comprises a cyclic group, the linking group can comprise a saturated cyclic group; alternatively, a substituted saturated cyclic group; alternatively, a saturated heteroatomic cyclic group; alternatively, a substituted saturated heteroatomic cyclic group; alternatively, an aromatic cyclic group; alternatively, a substituted aromatic cyclic group; alternatively, a heteroaromatic cyclic group; or alternatively, a substituted heteroaromatic cyclic group. In an embodiment wherein the linking group linking the aminyl nitrogen atoms of the diphosphino aminyl moieties is a hydrocarbon linking group, the hydrocarbon linking group can comprise a saturated cyclic group; alternatively, a substituted saturated cyclic group; alternatively, an aromatic cyclic group; or alternatively, a substituted aromatic cyclic group.

In an embodiment wherein the linking group comprises a cyclic group, the aminyl nitrogen atom of the diphosphino aminyl moiety can be attached to a ring carbon of the linking group. In an embodiment wherein the diphosphino aminyl ligand comprises two or more diphosphino aminyl moieties, the linking group can comprise at least one cyclic group (or any other number of cyclic groups described herein) and the aminyl nitrogen atom of at least one of the diphosphino aminyl moieties can be attached to a ring carbon of the linking group. In another embodiment wherein the diphosphino aminyl ligand comprises two or more diphosphino aminyl moieties, the linking group can comprise at least one cyclic group (or any other number of cyclic groups described herein) and the aminyl nitrogen atoms of each diphosphino aminyl moiety can be attached to a ring carbon of the linking group. In some embodiments wherein the diphosphino aminyl ligand comprises two or more diphosphino aminyl moieties, the linking group can comprise at least one cyclic group (or any other number of cyclic groups described herein) and the aminyl nitrogen atoms of two or more of the diphosphino aminyl moieties can be attached to a ring carbon of the same cyclic group of the linking group. In other embodiments wherein the diphosphino aminyl ligand comprises two or more diphosphino aminyl moieties, the linking group can comprise at least one cyclic group (or any other number of cyclic groups described herein) and the aminyl nitrogen atoms of each of the diphosphino aminyl moieties can be attached to a ring carbon of a different cyclic group of the linking group. In other embodiments wherein the diphosphino aminyl ligand comprises two or more diphosphino aminyl moieties, the linking group can comprise at least the same number of cyclic groups as there are diphosphino aminyl moieties and the aminyl nitrogen atoms of each diphosphino aminyl moiety can be attached to a ring carbon of a different cyclic group of the linking group. In yet other embodiments wherein the diphosphino aminyl ligand comprises two or more diphosphino aminyl moieties, the linking group can comprise the same number of cyclic groups as there are diphosphino aminyl moieties and the aminyl nitrogen atoms of each diphosphino aminyl moiety can be attached to a ring carbon of a different cyclic group of the linking group. Generally, any cyclic group of the linking group linking the aminyl nitrogen atoms of the diphosphino aminyl moieties may be an unsubstituted cyclic group or a substituted cyclic group(s). Furthermore, any cyclic groups of the linking group linking the aminyl nitrogen atoms of the diphosphino aminyl moieties may be any cyclic group or type of cyclic group (e.g. saturated cyclic, saturated heteroatomic, aromatic, or heteroaromatic) described herein.

In an embodiment, a linking group having at least one aminyl nitrogen atom of the diphosphino aminyl moiety attached to a ring carbon can comprise at least one alkyl substituent located on a carbon atom adjacent to a carbon atom on which the aminyl nitrogen of the diphosphino aminyl moiety is attached. In other embodiments, a linking group having at least one aminyl nitrogen atom of the diphosphino aminyl moiety attached to ring carbon can comprise only one alkyl substituent located on a carbon atom adjacent to each carbon atom on which the aminyl nitrogen atom of the diphosphino aminyl moiety is attached.

In an embodiment, a linking group having the aminyl nitrogen atom of each diphosphino aminyl moiety attached to a ring carbon can comprise at least one alkyl substituent located on a carbon atom adjacent to a carbon atom on which an aminyl nitrogen atom of the diphosphino aminyl moiety is attached. In some embodiments, the linking group having the aminyl nitrogen atom of each diphosphino aminyl moiety attached to a ring carbon can comprise at least one alkyl substituent located on a carbon atom adjacent to each carbon atom on which an aminyl nitrogen atom of the diphosphino aminyl moiety is attached. In other embodiments, the linking group having the aminyl nitrogen atom of each diphosphino aminyl moiety attached to a ring carbon can comprise only one alkyl substituent located on a carbon atom adjacent to each carbon atom on which an aminyl nitrogen atom of the diphosphino aminyl moiety is attached.

In an embodiment wherein the diphosphino aminyl ligand comprises only two diphosphino aminyl moieties, the linking group linking the aminyl nitrogen atoms of the two diphosphino aminyl moieties can be an organylene group, an organylene group consisting of inert functional groups, or a hydrocarbylene group. In some embodiments, the linking group linking the aminyl nitrogen atoms of the two diphosphino aminyl moieties can be an organylene group; alternatively, an organylene group consisting of inert functional groups; or alternatively, a hydrocarbylene group. In an embodiment, the linking group linking the aminyl nitrogen atoms of the two diphosphino aminyl moieties can be a $C_1$ to $C_{50}$ organylene group; alternatively, a $C_2$ to $C_{30}$ organylene group; or alternatively, a $C_2$ to $C_{20}$ organylene group. In some embodiments, the linking group linking the aminyl nitrogen atoms of the two diphosphino aminyl moieties can be a $C_1$ to $C_{50}$ organylene group consisting of inert functional groups; alternatively, a $C_2$ to $C_{30}$ organylene group consisting of inert functional groups; or alternatively, a $C_2$ to $C_{20}$ organylene group consisting of inert functional groups. In other embodiments, the linking group linking the aminyl nitrogen atoms of the diphosphino aminyl moieties can be a $C_2$ to $C_{50}$ hydrocarbylene group; alternatively, a $C_2$ to $C_{30}$ hydrocarbylene group; or alternatively, a $C_2$ to $C_{20}$ hydrocarbylene group.

In an embodiment wherein the diphosphino aminyl ligand comprises only two diphosphino aminyl moieties, the linking group, linking the aminyl nitrogen atoms of the two diphosphino aminyl moieties, can be acyclic. In some embodiments wherein the diphosphino aminyl ligand comprises only two diphosphino aminyl moieties, the linking group, linking the aminyl nitrogen atoms of the two diphosphino aminyl moieties, can comprise a cyclic group (a ring); or alternatively, a substituted cyclic group (a substituted ring). In other embodiments wherein the diphosphino aminyl ligand comprises only two diphosphino aminyl moieties, the linking group, linking the aminyl nitrogen atoms of the two diphosphino aminyl moieties, can comprise a saturated cyclic group; alternatively, a substituted saturated cyclic group; alternatively, a saturated heteroatomic cyclic group; alternatively, a substituted saturated heteroatomic cyclic group; alternatively, an aromatic group; alternatively, a substituted aromatic group; alternatively, a heteroaromatic group; or alternatively, a substituted heteroaromatic group. In some embodiments wherein the linking group linking the aminyl nitrogen atoms of the two diphosphino aminyl moieties is a hydrocarbon linking group, the hydrocarbon linking group, can comprises a saturated cyclic group; alternatively, a substituted saturated cyclic group; alternatively, an aromatic group; or alternatively, a substituted aromatic group. In an embodiment wherein the diphosphino aminyl ligand comprises only two diphosphino aminyl moieties, at least one of the aminyl nitrogen atoms of the two diphosphino aminyl groups can be attached to a ring carbon atom of a linking group comprising any cyclic group or type of cyclic group (e.g. saturated, substituted, unsubstituted, heteroatomic, aromatic, or heteroaromatic) described herein.

In an embodiment wherein the diphosphino aminyl ligand comprises only two diphosphino aminyl moieties, the linking group can comprise at least one cyclic group and the aminyl nitrogen atom of at least one of the two diphosphino aminyl moieties can be attached to a ring carbon of the linking group. In some embodiments wherein the diphosphino aminyl ligand comprises only two diphosphino aminyl moieties, the linking group can comprise at least one cyclic group and the aminyl nitrogen atom of each of the two diphosphino aminyl moieties can be attached to a ring carbon atom of the linking group. In other embodiments wherein the diphosphino aminyl ligand comprises only two diphosphino aminyl moieties, the aminyl nitrogen atoms of the two diphosphino aminyl moieties are attached to ring carbons of the same cyclic group of the linking group. In further embodiments wherein the diphosphino aminyl ligand comprises only two diphosphino aminyl moieties, the aminyl nitrogen atoms of the two diphosphino aminyl moieties can be attached different ring carbons of the same cyclic group of the linking group. In some embodiments wherein the diphosphino aminyl ligand comprises only two diphosphino aminyl moieties, the linking group can comprise two (or can comprise only two) cyclic groups and the aminyl nitrogen atoms of the two diphosphino aminyl moieties can be attached to a ring carbon of different cyclic groups of the linking group. Generally, any cyclic group of the linking group linking the aminyl nitrogen atoms of the two diphosphino aminyl moieties may be an unsubstituted cyclic group or a substituted cyclic group. Furthermore, any cyclic group of the linking group linking the aminyl nitrogen atoms of the two diphosphino aminyl moieties may be any cyclic group or type of cyclic group (e.g. saturated, heteroatomic, aromatic, or heteroaromatic) described herein.

In an embodiment, the linking group, L, linking the aminyl nitrogen atoms of the two diphosphino aminyl moieties can comprise a biscyclohexylene group, or a bisphenylene group. Alternatively, the linking group, L, linking the aminyl nitrogen atoms of the two diphosphino aminyl groups can be a substituted biscyclohexylene group; or alternatively, a substituted bisphenylene group. The substituents of the substituted linking group can be any substituent(s) described herein and can have any substituent pattern described herein. It is to be understood that since the diphosphino aminyl moiety and the linking group, L, can be independently selected from the groups disclosed herein, the heteroatomic ligand can have any combination of the diphosphino moieties described herein and the linking group described herein.

In an embodiment, the hydrocarbylene linking group, linking the aminyl nitrogen atoms of the two diphosphino aminyl moieties, can be $-(CR^PR^{P'})_m-$ where each $R^P$ and $R^{P'}$ can independently be hydrogen, methyl, ethyl, propyl, isopropyl, or butyl groups and m can be an integer from 1 to 12. In some embodiments, the linking group, linking the aminyl nitrogen atoms of the two diphosphino aminyl moieties, can be a methylene group ($-CH_2-$), an ethylene group ($-CH_2CH_2-$), a propylene group ($-CH_2CH_2CH_2-$), a $-CH(CH_3)CH_2-$ group, $-C(CH_3)_2-$ group, a butylene group ($-CH_2CH_2CH_2-CH_2-$), or a $-CH_2CH(CH_3)-CH_2-$ group. In other non-limiting embodiments, the linking group, linking the aminyl nitrogen atoms of the two diphosphino aminyl moieties, can be a methylene group (—CH$_2$—), an ethylene group (—CH$_2$CH$_2$—), or a —CH(CH$_3$)CH$_2$— group; alternatively, a methylene group (—CH$_2$—); alternatively, an ethylene group (—CH$_2$CH$_2$—); alternatively, a propylene group (—CH$_2$CH$_2$CH$_2$—); alternatively, a —CH(CH$_3$)CH$_2$— group; alternatively, a —C(CH$_3$)$_2$— group; or alternatively, or a —CH$_2$CH(CH$_3$)—CH$_2$— group.

In an embodiment, the hydrocarbylene linking group linking the aminyl nitrogen atoms of the two diphosphino aminyl moieties can be 1,2-phenylene (benzene-1,2-diyl), a substituted 1,2-phenylene (substituted benzene-1,2-diyl), 1,3-phenylene (benzene-1,3-diyl), a substituted 1,3-phenylene (substituted benzene-1,3-diyl), 1,4-phenylene (benzene-1,4-diyl), a substituted 1,4-phenylene (substituted benzene-1,4-diyl), 3,3'-biphenylene (biphenyl-3,3'-diyl), a substituted 3,3'-biphenylene (a substituted biphenyl-3,3'-diyl), 4,4'-biphenylene (biphenyl-4,4'-diyl), a substituted 4,4'-biphenylene (a substituted biphenyl-4,4'-diyl), bis(3-phenylene)methane, a substituted bis(3-phenylene)methane, bis(4-phenylene)methane, a substituted bis(4-phenylene)methane, 1,2-bis(3-phenylene)ethane, a substituted 1,2-bis(3-phenylene)ethane, 1,2-bis(4-phenylene)ethane, a substituted 1,2-bis(4-phenylene)ethane, 1,2-bis(3-phenylene)propane, a substituted 1,2-bis(3-phenylene)propane, 1,2-bis(4-phenylene)propane, a substituted 1,2-bis(4-phenylene)propane, 2,2-bis(3-phenylene)propane, a substituted 2,2-bis(3-phenylene)propane, 2,2-bis(4-phenylene)propane, or a substituted 2,2-bis(4-phenylene)propane. In some embodiments, the hydrocarbylene linking group linking the aminyl nitrogen atoms of the two diphosphino aminyl moieties can be a substituted 1,2-phenylene (substituted benzene-1,2-diyl), a substituted 1,3-phenylene (substituted benzene-1,3-diyl), a substituted 1,4-phenylene (substituted benzene-1,4-diyl), a substituted 3,3'-biphenylene (a substituted biphenyl-3,3'-diyl), a substituted 4,4'-biphenylene (a substituted biphenyl-4,4'-diyl), a substituted bis(3-phenylene)methane, a substituted bis(4-phenylene)methane, a substituted 1,2-bis(3-phenylene)ethane, a substituted 1,2-bis(4-phenylene)ethane, a substituted 1,2-bis(3-phenylene)propane, a substituted 1,2-bis(4-phenylene)propane, a substituted 2,2-bis(3-phenylene)propane, or a substituted 2,2-bis(4-phenylene)propane.

In an embodiment, the hydrocarbylene linking group linking the aminyl nitrogen atoms of the two diphosphino aminyl moieties can be 1,2-cyclohexylene (cyclohexane-1,2-diyl), a substituted 1,2-cyclohexylene (substituted cyclohexane-1,2-diyl), 1,3-cyclohexylene (cyclohexane-1,3-diyl), a substituted 1,3-cyclohexylene (substituted cyclohexane-1,3-diyl), 1,4-cyclohexylene (cyclohexane-1,4-diyl), a substituted 1,4-cyclohexylene (substituted cyclohexane-1,4-diyl), 3,3'-bicyclohexylene (bicyclohexyl-3,3'-diyl), a substituted 3,3'-bicyclohexylene (substituted bicyclohexyl-3,3'-diyl), 4,4'-bicyclohexylene (bicyclohexyl-4,4'-diyl), a substituted 4,4'-bicyclohexylene (substituted bicyclohexyl-4,4'-diyl), bis(3-cyclohexylene)methane, a substituted bis(3-cyclohexylene)methane, bis(4-cyclohexylene)methane, a substituted bis(4-cyclohexylene)methane, 1,2-bis(3-cyclohexylene)ethane, a substituted 1,2-bis(3-cyclohexylene)-ethane, 1,2-bis(4-cyclohexylene)ethane, a substituted 1,2-bis(4-cyclohexylene)ethane, 1,2-bis(3-cyclohexylene)propane, a substituted 1,2-bis(3-cyclohexylene)propane, 1,2-bis(4-cyclohexylene)propane, a substituted 1,2-bis(4-cyclohexylene)propane, 2,2-bis(3-cyclohexylene)propane, a substituted 2,2-bis(3-cyclohexylene)propane, 2,2-bis(4-cyclohexylene)propane, or a substituted 2,2-bis(4-cyclohexylene)propane. In some embodiments, the hydrocarbylene linking group linking the aminyl nitrogen atoms of the two diphosphino aminyl moieties can be a substituted 1,2-cyclohexylene (substituted cyclohexane-1,2-diyl), a substituted 1,3-cyclohexylene (substituted cyclohexane-1,3-diyl), a substituted 1,4-cyclohexylene (substituted cyclohexane-1,4-diyl), a substituted 3,3'-bicyclohexylene (substituted bicyclohexyl-3,3'-diyl), a substituted 4,4'-bicyclohexylene (substituted bicyclohexyl-4,4'-diyl), a substituted bis(3-cyclohexylene)methane, a substituted bis(4-cyclohexylene)methane, a substituted 1,2-bis(3-cyclohexylene)ethane, a substituted 1,2-bis(4-cyclohexylene)ethane, a substituted 1,2-bis(3-cyclohexylene)propane, a substituted 1,2-bis(4-cyclohexylene)propane, a substituted 2,2-bis(3-cyclohexylene)propane, or a substituted 2,2-bis(4-cyclohexylene)propane.

In some embodiments, the linking group can be a 3,3'-dialkyl-4,4'-biphenylene; alternatively, a bis(3-alkyl-4-phenylene)methane; alternatively, 1,2-bis(3-alkyl-4-phenylene)ethane; alternatively, 1,2-bis(3-alkyl-4-phenylene)propane; or alternatively, 2,2-bis(3-alkyl-4-phenylene)propane. In other embodiments the linking group can be can be a 3,3'-dialkyl-4,4'-bicyclohexylene; alternatively, a bis(3-alkyl-4-cyclohexylene)methane; alternatively, 1,2-bis(3-alkyl-4-cyclohexylene)ethane; alternatively, 1,2-bis(3-alkyl-4-cyclohexylene)propane; or alternatively, 2,2-bis(3-alkyl-4-cyclohexylene)propane. In some non-limiting embodiments the alkyl group can be any alkyl substituent described herein. In other embodiments, the alkyl group can be a methyl group.

In an embodiment, the substituents of the substituted linking group, L, can be a hydrocarbyl group, an organyl group, an organyl group consisting of an inert functional group, or an inert functional group. In some embodiments, the substituents of the substituted linking group, L, can be an alkyl group. In an embodiment, the hydrocarbyl, organyl, or organyl consisting of inert functional group substituents of the substituted linking group, L, can have from 1 to 10 carbon atoms; alternatively, from 1 to 6 carbon atoms; or alternatively, from 1 to 4 carbon atoms.

In an embodiment, the alkyl substituents of the substituted linking group, L, can be a methyl, ethyl, n-propyl (1-propyl), isopropyl (2-propyl), n-butyl (1-butyl), sec-butyl (2-butyl), isobutyl (2-methyl-1-propyl), tert-butyl (2-methyl-2-propyl), n-pentyl (1-pentyl), 2-pentyl, 3-pentyl, 2-methyl-1-butyl, tert-pentyl (2-methyl-2-butyl), 3-methyl-1-butyl, 3-methyl-2-butyl, neo-pentyl (2,2-dimethyl-1-propyl), or n-hexyl (1-hexyl) group. In some embodiments, the alkyl substituents of the substituted linking group, L, can be a methyl, ethyl, n-propyl (1-propyl), n-butyl (1-butyl), isobutyl (2-methyl-1-propyl), n-pentyl (1-pentyl), 2-methyl-1-butyl, 3-methyl-1-butyl, neo-pentyl (2,2-dimethyl-1-propyl), or n-hexyl (1-hexyl) group. In other embodiments, the alkyl substituents of the substituted linking group, L, can be a methyl group.

In an embodiment, the diphosphino aminyl ligand can comprise any number of diphosphino aminyl moieties as disclosed herein and can comprise at least one primary diphosphino aminyl moiety; alternatively, at least one secondary diphosphino aminyl moiety; or alternatively, at least one tertiary diphosphino aminyl moiety. In some embodiments, the diphosphino aminyl moieties can consist of secondary diphosphino aminyl moieties. The terms primary, secondary, and tertiary diphosphino aminyl moieties refers to the type of carbon atom that the aminyl nitrogen atom of the diphosphino aminyl moiety is attached. A primary diphosphino moiety is one in which the aminyl nitrogen atom of the diphosphino aminyl moiety is attached to a carbon atom which is attached to only one other carbon atom. A secondary diphosphino moiety is one in which the aminyl nitrogen atom of the diphosphino aminyl moiety is attached to a carbon atom which is attached to two other carbon atoms. A tertiary diphosphino moiety is one in which the aminyl nitrogen atom of the diphosphino aminyl moiety is attached to a carbon atom which is attached to three other carbon atoms. The terms "wherein the diphosphino aminyl moieties consist of secondary diphosphino aminyl moieties" only refers to the type of carbon atom to which the diphosphino aminyl moiety of the diphosphino aminyl ligand is attached and does not imply the presence or absence of any other diphosphino aminyl ligand element. The diphosphino aminyl ligand can and will likely contain other elements as described herein.

In an embodiment, the diphosphino aminyl ligand, regardless of the number of diphosphino aminyl moieties, can comprise at least one tertiary carbon atom adjacent (i.e. attached) to a carbon atom to which the aminyl nitrogen atom of a diphosphino aminyl moiety is attached. In some embodiments, the diphosphino aminyl ligand, regardless of the number of diphosphino aminyl moieties, can comprise at least one tertiary carbon atom adjacent (i.e. attached) to each carbon atom to which the aminyl nitrogen atom of the diphosphino aminyl moiety is attached. In other embodiments, the diphosphino aminyl ligand, regardless of the number of diphosphino aminyl moieties, can have only one tertiary carbon atom adjacent (i.e. attached) to each carbon atom to which the aminyl nitrogen atom of the diphosphino aminyl moiety is attached.

For illustrative purposes, general structures AA-AU comprising only two diphosphino moieties linked by a saturated hydrocarbylene and having various tertiary carbon atoms within the hydrocarbylene linking group are presented. Statements regarding which of structures AA-AU meet or do not meet three criteria for the location of the tertiary carbon atoms in relation to the diphosphino aminyl moiety(ies) are presented to assist the skilled artisan in visualizing the relationship between the tertiary carbon atoms and the aminyl nitrogen atom of the diphosphino aminyl moiety. Structures AA-AU do not limit the herein disclosed invention to these structures, to diphosphino aminyl ligands comprising only 2 diphosphino aminyl moieties, and/or saturated hydrocarbylene linking groups. The diphosphino aminyl ligand can have any number of diphosphino aminyl moieties as described herein and/or any type of linking group linking the aminyl nitrogen atoms of the diphosphino aminyl moieties as described herein (e.g. aromatic of heteroaromatic linking groups). Upon review a skilled artisan will be able to apply the criteria for the location of tertiary carbon atoms to build and determine other materials having 1, 2, 3 or more diphosphino aminyl moieties that can meet the criteria for the location of the tertiary carbon atoms in relation to the diphosphino aminyl moiety(ies).

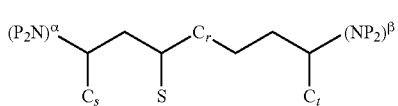

Structure AA

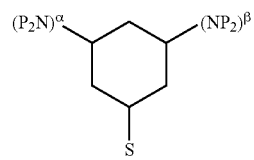

Structure AB

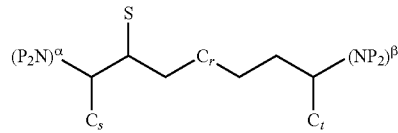

Structure AC

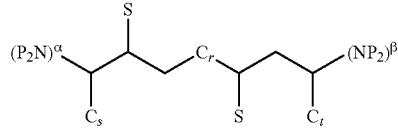

Structure AD

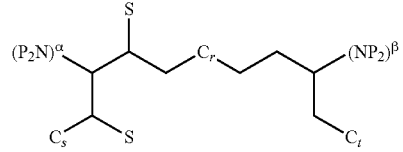

Structure AE

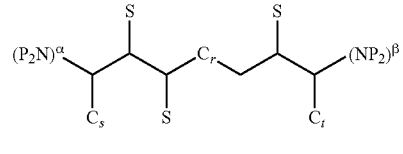

Structure AF

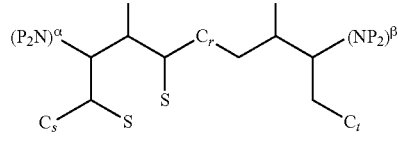

Structure AG

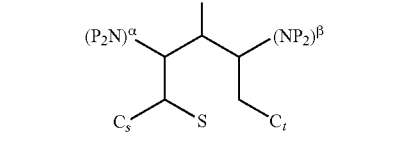

Structure AH

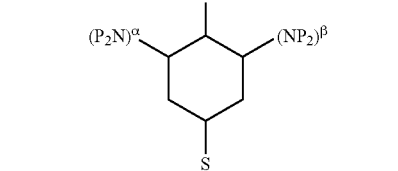

Structure AI

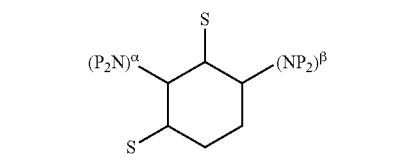

Structure AJ

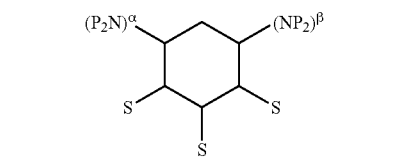

Structure AK

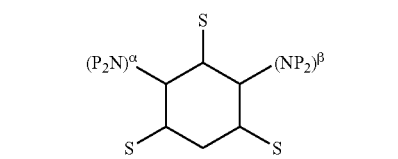

Structure AL

-continued

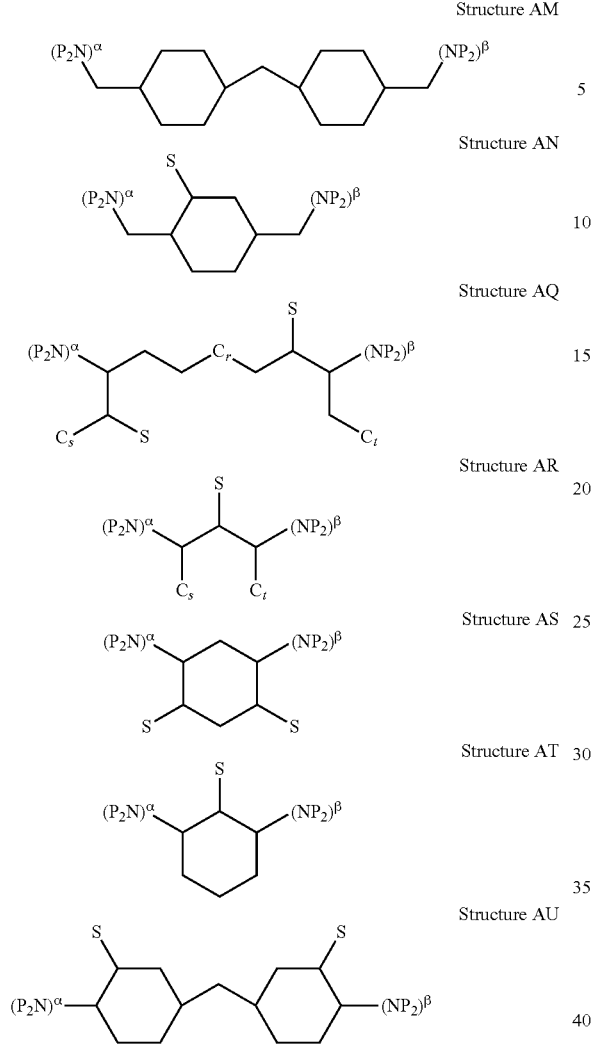

Structure AM

Structure AN

Structure AQ

Structure AR

Structure AS

Structure AT

Structure AU

Within Structures AA-AU, $(P_2N)^\alpha$— and —$(NP_2)^\beta$ represent generalized diphosphino aminyl moieties, $C_r$ represents a generalized hydrocarbon group, a generalized organyl group, or a generalized organyl group consisting of inert functional groups, $C_s$, and $C_t$, can represent a hydrogen atom, a generalized hydrocarbyl group, a generalized organyl group, or a generalized organyl group consisting of inert functional groups, and S represents a generalized substituent.

Structures AA and AB do not satisfy the criteria of the phrase "comprises at least one tertiary carbon atom adjacent to a carbon atom on which an aminyl nitrogen atom of a diphosphino aminyl moiety is attached." While each of these structures have tertiary carbon atom within the structure, the tertiary carbon atom is not adjacent to the carbon atom on which the aminyl nitrogen atom of the diphosphino aminyl moiety alpha or beta are attached.

Structures AC-AU satisfy the criteria of the phrase "comprises at least one tertiary carbon atom adjacent to a carbon atom on which an aminyl nitrogen atom of a diphosphino aminyl moiety is attached."

1. Structures AC, AD, AI, AR, and AT each have one tertiary carbon atom located on a carbon atom adjacent to a carbon atom on which the aminyl nitrogen atom of the diphosphino aminyl moiety alpha is attached.
   (a) Structures AC and AD have one tertiary carbon atom located on a carbon adjacent to the carbon atom on which the aminyl nitrogen atom of a diphosphino aminyl moiety is attached.
   (b) Structures AI, AR, and AT each have one tertiary carbon atom located on a carbon atom adjacent to both the carbon atom on which the aminyl nitrogen atom of diphosphino aminyl moiety alpha is attached and the aminyl nitrogen atom of diphosphino aminyl moiety beta is attached.
   (c) Structures AD and AI have an additional tertiary carbon atom not located on carbon atom adjacent to a carbon atom on which an aminyl nitrogen atom of a diphosphino aminyl moiety is attached. However, Structures AD and AI meet the requirement of comprising at least one tertiary carbon atom adjacent to a carbon atom on which an aminyl nitrogen atom of a diphosphino aminyl moiety is attached.
2. Structures AE, AF, AH, AJ, AK, AM, AN, AQ, AS, and AU have two tertiary carbon atoms located on a carbon atoms adjacent to a carbon atom on which the aminyl nitrogen atom of the diphosphino aminyl moiety is attached.
   (a) Structure AE has two tertiary carbon atoms located on a carbon atom adjacent to the carbon on which the aminyl nitrogen atom of diphosphino aminyl moiety alpha is located.
   (b) Structures AF, AK, AM, AN, AQ, AS, and AU have a tertiary carbon atom located on a carbon atom adjacent to the carbon atom on which the aminyl nitrogen atom of diphosphino aminyl moiety alpha is located and a second tertiary carbon atom located on a carbon atom adjacent to the carbon atom on which the aminyl nitrogen atom of diphosphino aminyl moiety beta is located.
   (c) Structures AH and AJ have a tertiary carbon atom located on a carbon atom adjacent to the carbon atom on which the aminyl nitrogen atom of diphosphino aminyl moiety alpha is located and a second tertiary carbon atom located adjacent to the carbon atom on which the aminyl nitrogen atom of diphosphino aminyl moiety alpha and the aminyl nitrogen atom of diphosphino aminyl moiety beta is located.
   (d) Structures AF, AK, AM, and AN have additional tertiary carbon atoms not located on carbon atoms which are not adjacent to a carbon atom on which an aminyl nitrogen atom of a diphosphino aminyl moiety is attached. However, Structures AF, AK, AM, and AN meet the criteria of comprising "at least one tertiary carbon atom adjacent to a carbon atom on which an aminyl nitrogen atom of a diphosphino aminyl moiety is attached."
3. Structures AG and AL have three tertiary carbon atoms located on carbon atoms adjacent to the carbon atom on which the aminyl nitrogen atom of a diphosphino aminyl moiety is attached.
   (a) Structure AG has two tertiary carbon atoms located on a carbon atom adjacent to the carbon atom on which the aminyl nitrogen atom of diphosphino aminyl moiety alpha is located and a third tertiary carbon atom located on a carbon atom adjacent to a carbon atom on which the aminyl nitrogen atom of diphosphino aminyl moiety beta is located.
   (b) Structure AL has one tertiary carbon atom located on a carbon atom adjacent to the carbon atom on which the aminyl nitrogen atom of diphosphino aminyl moiety alpha is located, a second tertiary carbon atom located on a carbon atom adjacent to the carbon atom on which the aminyl nitrogen atom of diphosphino aminyl moiety beta is located, and a third tertiary carbon atom located on a carbon atom adjacent to the carbon atoms on which the aminyl nitrogen atom of diphosphino aminyl moiety alpha and the aminyl nitrogen atom of diphosphino aminyl moiety beta is located.

(c) Structure AG has an additional tertiary carbon atom not located on carbon atom adjacent to a carbon atom on which an aminyl nitrogen atom of a diphosphino aminyl moiety is attached. However, Structure AG meets the criteria of comprising "at least one tertiary carbon atom adjacent to a carbon atom on which an aminyl nitrogen atom of a diphosphino aminyl moiety is attached."

Structures AA, AB, AC, AD, and AE do not satisfy the criteria of the phrase "comprises at least one tertiary carbon atom adjacent to each carbon atom to which the aminyl nitrogen atom of the diphosphino aminyl moiety is attached."

1. Structures AA and AB do not have any tertiary carbon atoms located on carbon atom adjacent to a carbon atoms on which an aminyl nitrogen atom of which a diphosphino aminyl moiety is attached.
2. Structures AC, AD, and AE have at least one tertiary atom located adjacent to the carbon atom on which the aminyl nitrogen atom of diphosphino aminyl moiety alpha is attached but no tertiary carbon atom adjacent to the carbon atom on which the diphosphino aminyl moiety beta is attached.

Structures AF-AU satisfy the criteria of the phrase "comprises at least one tertiary carbon atom adjacent to each carbon atom on which an aminyl nitrogen atom of a diphosphino aminyl moiety is attached."

1. Structures AI, AR, and AT each have one tertiary carbon atom located on a carbon atom adjacent to both the carbon atom on which the diphosphino aminyl moiety alpha is located and the aminyl nitrogen atom of diphosphino aminyl moiety beta is attached. Structure AI has an additional tertiary carbon atom not located on carbon atom adjacent to a carbon atom on which an aminyl nitrogen atom of a diphosphino aminyl moiety is attached. However, Structure AI meets the criteria of comprising "at least one tertiary carbon atom adjacent to each carbon atom on which an aminyl nitrogen atom of a diphosphino aminyl moiety is attached."
2. Structures AF, AH, AJ, AK, AM, AN, AQ, AS, and AU have two tertiary carbon atoms located on a carbon atoms adjacent to a carbon atom on which the aminyl nitrogen atom of the diphosphino aminyl moiety is attached.
   (a) Structures AF, AK, AM, AN, AQ, AS, and AU have a tertiary carbon atom located on a carbon atom adjacent to the carbon atom on which a diphosphino aminyl moiety alpha is located and a second tertiary carbon atom located on a carbon atom adjacent to the carbon atom on which a diphosphino aminyl moiety beta is located.
   (b) Structures AH and AJ have a tertiary carbon atom located on a carbon atom adjacent to the carbon atom on which a diphosphino aminyl moiety alpha is located and a second tertiary carbon atom located adjacent to both the carbon atom on which the aminyl nitrogen atom of diphosphino aminyl moiety alpha is located and the aminyl nitrogen atom of diphosphino aminyl moiety beta is located.
   (c) Structures AF, AK, AM, and AN have additional tertiary carbon atoms not located on carbon atoms adjacent to a carbon atom on which an aminyl nitrogen atom of a diphosphino aminyl moiety is attached. However, Structures AF, AK, AM, and AN meet the criteria of comprising "at least one tertiary carbon atom adjacent to a carbon atom on which an aminyl nitrogen atom of a diphosphino aminyl moiety is attached."
3. Structures AG and AL have three tertiary carbon atoms located on carbon atoms adjacent to the carbon atom on which the aminyl nitrogen atom of a diphosphino aminyl moiety is attached.
   (a) Structure AG has two tertiary carbon atoms located on a carbon atom adjacent to the carbon atom on which the aminyl nitrogen atom of diphosphino aminyl moiety alpha is located and a third tertiary carbon atom located on a carbon atom adjacent to a carbon atom on which the aminyl nitrogen atom of diphosphino aminyl moiety beta is located.
   (b) Structure AL has one tertiary carbon atom located on a carbon atom adjacent to the carbon atom on which the aminyl nitrogen atom of diphosphino aminyl moiety alpha is located, a second tertiary carbon atom located adjacent to a carbon atom on which the aminyl nitrogen atom of diphosphino aminyl moiety beta is located, and a third tertiary carbon atom located adjacent to the carbon atom on which the aminyl nitrogen atom of diphosphino aminyl moiety alpha and the aminyl nitrogen atom of diphosphino aminyl moiety beta is located.
   (c) Structure AG has an additional tertiary carbon atom not located on carbon atom adjacent to a carbon atom on which an aminyl nitrogen atom of a diphosphino aminyl moiety is attached. However, Structure AG meets the criteria of comprising "at least one tertiary carbon atom adjacent to a carbon atom on which an aminyl nitrogen atom of a diphosphino aminyl moiety is attached."

Structures AA-AE, AG-AH, AJ, and AL do not satisfy the criteria of the phrase "comprises only one tertiary carbon atom adjacent to each carbon atom to which the aminyl nitrogen atom of the diphosphino aminyl moiety is attached."

1. Structures AA and AB do not have any tertiary carbon atoms located on a carbon atom adjacent to a carbon atoms on which an aminyl nitrogen atom of which a diphosphino aminyl moiety is attached.
2. Structures AC, AD, and AE have at least one tertiary atom located on a carbon atom adjacent to the carbon atom on which the aminyl nitrogen atom of diphosphino aminyl moiety alpha is attached but no tertiary carbon atom adjacent to the carbon atom on which the diphosphino aminyl moiety beta is attached.
3. Structures AG, AH, AJ, and AL have more that one tertiary carbon atom located on a carbon atom adjacent to the carbon atom on which the aminyl nitrogen atom of diphosphino aminyl moiety alpha is located.

Structures AF, AI, AK, AM, AN, AQ, AR, AS, AT, and AU satisfy the criteria of the phrase "comprises only one tertiary carbon atom adjacent to each carbon atom to which the aminyl nitrogen atom of the diphosphino aminyl moiety is attached."

1. Structures AI, AR, and AT each have one tertiary carbon atom located on a carbon atom adjacent to both the carbon atom on which the diphosphino aminyl moiety alpha is located and the aminyl nitrogen atom of diphosphino aminyl moiety beta is attached and has no other tertiary carbon atoms located on a carbon atom adjacent to a carbon atom on which the aminyl nitrogen atom of a diphosphino aminyl moiety is attached.

2. Structures AF, AK, AM, AN, AQ, AS, and AU have one tertiary carbon atom located on a carbon atom adjacent to the carbon atom on which the aminyl nitrogen atom of a diphosphino aminyl moiety alpha is located and a second tertiary carbon atom located on a carbon atom adjacent to the carbon atom on which the aminyl nitrogen atom diphosphino aminyl moiety beta is located.
3. Structures AF, AI, AK, and AM have at least one additional tertiary carbon atom that is not located on carbon atom adjacent to a carbon atom on which an aminyl nitrogen atom of a diphosphino aminyl moiety is attached. However, AF, AI, AK, AM, and AO meets the criteria of comprising "only one tertiary carbon atom adjacent to each carbon atom to which the aminyl nitrogen atom of the diphosphino aminyl moiety is attached."

In an aspect, the heteroatomic ligand having multiple diphosphino aminyl moieties can have two diphosphino aminyl moieties connected by a linking group. In an embodiment, the heteroatomic ligand can be represented by the chemical formula $(R^1R^2P)(R^3R^4P)N-L-N(R^{1'}R^{2'}P)(R^{3'}R^{4'}P)$, Structure IV:

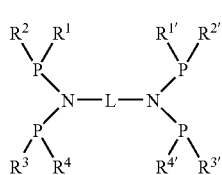

Structure IV wherein the two diphosphino aminyl moieties can independently be any diphosphino aminyl moiety described herein and wherein L can be any linking group linking the two diphosphino aminyl moieties as described herein. In some embodiments, the first diphosphino aminyl moiety $(R^1R^2P)(R^3R^4P)N-$) and the second diphosphino aminyl group $(-N(R^{1'}R^{2'}P)(R^{3'}R^{4'}P))$ are different; or alternatively, the first diphosphino aminyl group $(R^1R^2P)(R^3R^4P)N-$) and the second diphosphino aminyl group $(-N(R^{1'}R^{2'}P)(R^{3'}R^{4'}P))$ are the same. In another embodiment, a heteroatomic ligand can be represented by Structure V:

wherein the two bis(diphenylphosphino) aminyl moieties can independently be any bis(diphenyl-phosphino) aminyl moiety described herein and L can be any linking group linking the nitrogen atoms of the bis(diphenylphosphino) aminyl moieties described herein. In some embodiments, the two bis(diphenylphosphino) aminyl moieties are different; or alternatively, the two bis(diphenyl-phosphino) aminyl moieties are the same.

In an embodiment, the linking group can have any Structure in Table 1. In some embodiments, the linking group can have Structure 1L; alternatively, Structure 2L; alternatively, Structure 3L; alternatively Structure 4L; alternatively, Structure 5L; alternatively, Structure 6L; alternatively, Structure 7L; alternatively, Structure 8L; alternatively, Structure 9L; or alternatively, Structure 10L.

TABLE 1

Linking groups for heteroatomic ligand having two diphosphino aminyl group linked by a linking group, L.

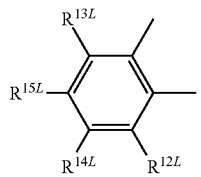

Structure 1L

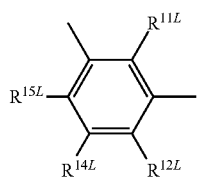

Structure 2L

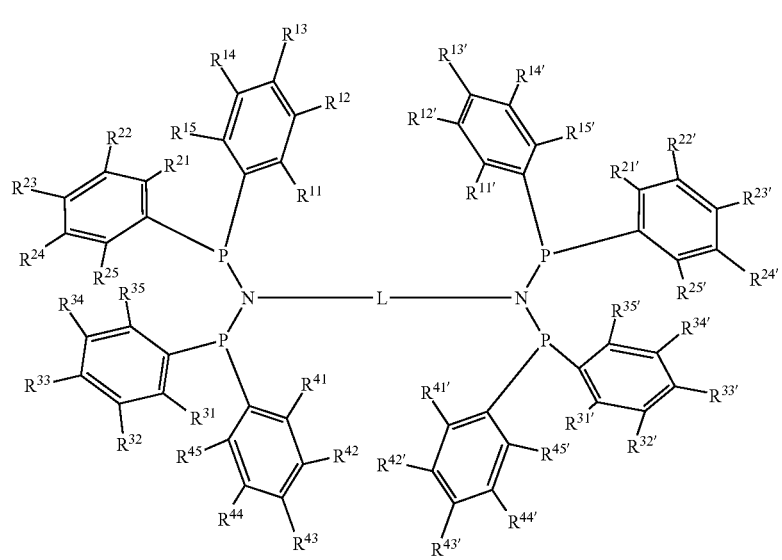

Structure V

TABLE 1-continued

Linking groups for heteroatomic ligand having two diphosphino aminyl group linked by a linking group, L.

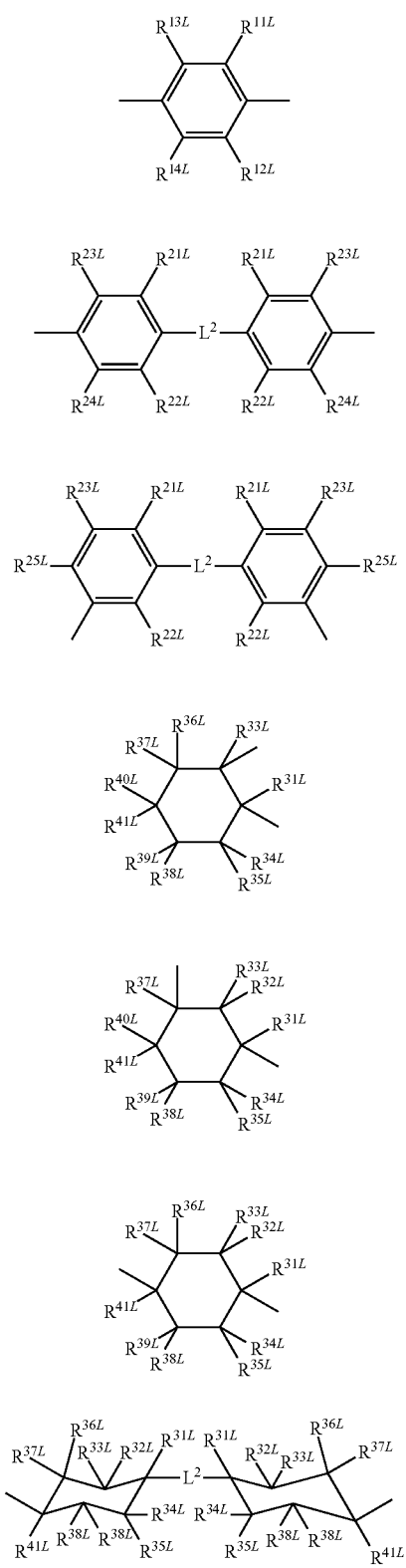

Structure 3L

Structure 4L

Structure 5L

Structure 6L

Structure 7L

Structure 8L

Structure 9L

TABLE 1-continued

Linking groups for heteroatomic ligand having two diphosphino aminyl group linked by a linking group, L.

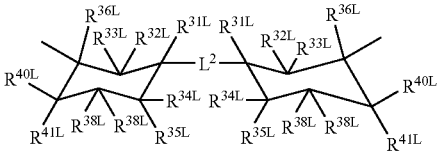

Structure 10L

Within the Structures of Table 1, $R^{11L}$ to/through $R^{15L}$, $R^{21L}$ to/through $R^{25L}$, $R^{31L}$ to/through $R^{41L}$ can each independently be hydrogen, an organyl group consisting of inert functional groups, a hydrocarbyl group, or an inert functional groups, $L^2$ represents a linking group, and the undesignated valencies represent the positions at which the nitrogen atoms of the diphosphino aminyl moieties are attached. In some embodiments, $R^{11L}$ to/through $R^{15L}$, $R^{21L}$ to/through $R^{25L}$, $R^{31L}$ to/through $R^{41L}$ of each Structure of Table 1 can independently be hydrogen, a $C_1$ to $C_{10}$ organyl group consisting of inert functional groups, a $C_1$ to $C_{10}$ hydrocarbyl group, or an inert functional group; or alternatively, hydrogen, a $C_1$ to $C_5$ organyl group consisting of inert functional groups, a $C_1$ to $C_5$ hydrocarbyl group or an inert functional group. The substituent(s) of the linking groups having Structure 1L, Structure 2L, Structure 3L, Structure 4L, Structure 5L, Structure 6L, Structure 7L, Structure 8L, Structure 9L or Structure 10L can independently be any substituent described herein, have any substituent pattern described herein, and/or have any pattern necessary to meet any criteria of the diphosphino aminyl ligand as described herein.

In an embodiment, linking group $L^2$ can be $—(CR^LR^L)_m—$ where each $R^L$ and $R^L$ can independently be hydrogen, methyl, ethyl, propyl, isopropyl, or butyl groups and m can be an integer from 1 to 5. In other embodiments, the linking group $L^2$ can be a bond, a methylene group (—CH$_2$—), an ethylene group (—CH$_2$CH$_2$—), a propylene group (—CH$_2$CH$_2$CH$_2$—), a —CH(CH$_3$)CH$_2$— group, —C(CH$_3$)$_2$— group, or a butylene group (—CH$_2$CH$_2$CH$_2$CH$_2$—). In some non-limiting embodiments, the linking group $L^2$ can be a methylene group (—CH$_2$—), an ethylene group (—CH$_2$CH$_2$—), or a —CH(CH$_3$)CH$_2$— group; or alternatively, an ethylene group (—CH$_2$CH$_2$—), or a —CH(CH$_3$)CH$_2$— group. In yet other embodiments, the linking group can be a methylene group; alternatively, an ethylene group; alternatively, a propylene group; alternatively, a —CH(CH$_3$)CH$_2$— group; or alternatively —C(CH$_3$)$_2$— group.

In some embodiments, the heteroatomic ligand can have Structure VI:

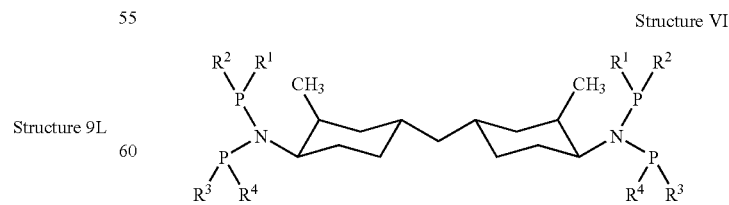

Structure VI wherein the diphosphino aminyl moieties, $(R^1R^2P)(R^3R^4P)$ N—, can be any described herein and the undesignated valencies represent hydrogen. In other embodiments, the heteroatomic ligand can have Structure VII:

Structure VII

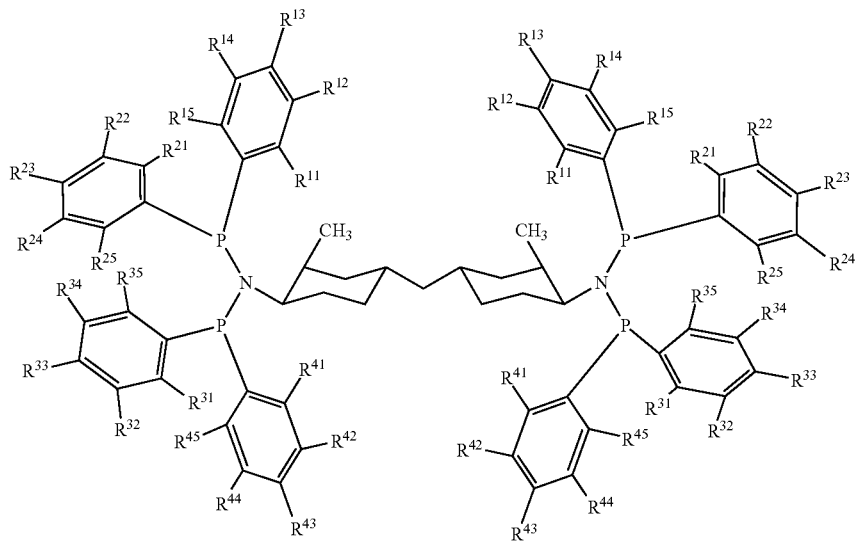

wherein the bis(diphenylphosphino) aminyl moieties can be any described herein and the undesignated valencies represent hydrogen. In other embodiments, the heteroatomic ligand can have Structure VIII:

Structure VIII

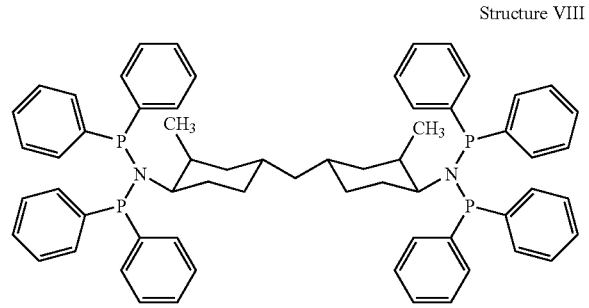

wherein the undesignated valencies represent hydrogen. Skilled artisans will readily know how to produce other heteroatomic ligand comprising multiple diphosphino aminyl moieties and a linking group linking the nitrogen atoms of the diphosphino aminyl moieties by utilizing the diphosphino aminyl moieties described herein, the linking groups L and/or $L^2$ described herein, the substituents described herein, the substituent patterns described herein, and other aspects of the diphosphino aminyl moieties and/or diphosphino aminyl ligands as described herein. Though not specifically drawn, these structures are incorporated in this disclosure.

In an embodiment, the metal compound, $M\text{-}X_p$, of the olefin oligomerization catalyst comprising a metal compound complexed to a heteroatomic ligand can comprise any transition metal. In some embodiments, the metal compound comprises a group IVB, VB, or VIB metal (the group designation is CAS group designations). In other embodiments, the metal compound comprises titanium, vanadium, or chromium. In yet other embodiments, the metal compound comprises chromium.

The anion X, of the metal compound can be any anion. In some embodiments, the anion X can be a halide, carboxylate, acetonate, alkoxide, phenoxide, nitrate, sulfate, phosphate, or chlorate. In some embodiments, the anion, X, is a halide, carboxylate, or acetonate. In other embodiments, the anion can be a halide; alternatively, a carboxylate; or alternatively, acetonate.

In an embodiment, the halide anion can be fluoride, chloride, bromide, iodide, or combinations thereof; alternatively, chloride, bromide, iodide, or combinations thereof. In other embodiments, the halide anion can be chloride; alternatively, bromide; or alternatively, iodide.

In carboxylate, acetonate, alkoxide or phenoxide embodiments, the carboxylate, acetonate, alkoxide, or phenoxide can be any $C_1$ to $C_{20}$ carboxylate, acetonate, alkoxide, or phenoxide; or alternatively, any $C_1$ to $C_{10}$ carboxylate, acetonate, alkoxide, or phenoxide. In some embodiments, the anion, X, can be a $C_1$ to $C_{10}$ acetonate; alternatively, a $C_1$ to $C_{10}$ carboxylate; alternatively, a $C_1$ to $C_{10}$ alkoxide; or alternatively, a $C_1$ to $C_{10}$ phenoxide. In other embodiments, the anion X, can be acetylacetonate; alternatively, acetate; alternatively, 2-ethylhexanoate; or alternatively, triflate.

Generally, the number, p, of anions, X, is such that the total number of negative charges on the total number of X anions equals the oxidation state of M. In an embodiment, p is 2, or 3, and the total number of negative charges on the Xs bonded to the metal atom is equal to the oxidation state of M. In other embodiments, the total number of anions, p, is 2; or alternatively, 3.

In some embodiments wherein the metal compound comprises chromium, the chromium-containing compound may be a chromium(II) compound, chromium(III) compound, or combinations thereof. Suitable chromium(II) compounds include, but are not limited to, chromium(II) fluoride, chromium(II) chloride, chromium(II) bromide, chromium(II) iodide, chromium(II) (2-ethylhexanoate), chromium(II) acetate, chromium(II) butyrate, chromium(II) neopentanoate, chromium(II) laurate, chromium(II) stearate, chromium(II) oxalate, chromium(II) benzoate, or combinations thereof. Suitable chromium(III) compounds include, but are not limited to, chromium(III) trichloride tris-tetrahydrofuran complex, chromium(III) 2,2,6,6-tetramethylheptanedionate, chromium(III) naphthenate, chromium(III) chloride, chromium(III) bromide, chromium(III) chloride, chromium(III) fluoride, chromium(III) acetylacetonate, or combinations thereof.

In an embodiment, the chromium-containing compound can be a chromium(III) carboxylate. Without limitation, examples of chromium(III) carboxylates include chromium (III) isooctanoate, chromium(III) (2-ethylhexanoate), chromium(III) oxy-2-ethylhexanoate, chromium(III) dichloroethylhexanoate, chromium(III) acetate, chromium(III)

butyrate, chromium(III) neopentanoate, chromium(III) laurate, chromium(III) stearate, chromium(III) oxalate, chromium(III) benzoate, chromium(III) octanoate, chromium (III) propionate, or combinations thereof. In an embodiment, the chromium-containing compound can be chromium(III) (2-ethylhexanoate).

In another embodiment, the chromium-containing compound can be a chromium β-diketonate. Examples of such chromium β-diketonates include without limitation chromium (III) acetylacetonate, chromium (III) hexafluoroacetylacetonate and tris(2,2,6,6-tetramethyl-3,5-heptanedionato) chromium (III). In an embodiment, the chromium β-diketonate is chromium (III) acetylacetonate (also referred to as Cr(acac)$_3$).

In an aspect, the oligomerization catalyst can be a metal complex comprising a metal compound complexed to a heteroatomic ligand. In an embodiment, the heteroatomic ligand can be any heteroatomic ligand described herein. In some embodiments, the heteroatomic ligand can be any ligand comprising any dialkylphosphino moiety described herein; alternatively, any heteroatomic ligand comprising multiple dialkylphosphino moieties described herein; alternatively, any heteroatomic ligand comprising at least two dialkylphosphino moieties; or alternatively, any heteroatomic ligand comprising only two dialkylphosphino moieties. In general, the heteroatomic ligand and the metal compound are independent elements of the catalyst. Thus, the catalyst can be described using any combination of the heteroatomic ligand described herein and the metal compound described herein.

In an embodiment, the metal complex can be described as a product of contacting a metal compound with a heteroatomic ligand. As the metal compound and the heteroatomic ligand are independent elements, the metal complex can be as described as contacting any metal compound described herein with any heteroatomic ligand described herein. In an embodiment, the metal complex can be described as the product of contacting a metal compound with a heteroatomic ligand comprising a diphosphino aminyl moiety; alternatively, with a heteroatomic ligand comprising at least 2 diphosphino aminyl moieties; alternatively, with a heteroatomic ligand comprising 2 to 5 diphosphino aminyl moieties; alternatively, with a heteroatomic ligand comprising 2 to 3 diphosphino aminyl moieties; or alternatively, with a heteroatomic ligand comprising 2 diphosphino aminyl moieties.

In an embodiment, the heteroatomic ligand can be a diphosphino aminyl ligand. In some embodiments, the diphosphino aminyl moieties of the diphosphino aminyl ligand can be any diphosphino aminyl moiety described herein. In some embodiments, the diphosphino aminyl moieties can have Structure 1, Structure 3, or any combination thereof. In other embodiments, the diphosphino aminyl moieties can have Structure 1, or alternatively, Structure 3.

In an embodiment, the metal complex comprising a metal compound complexed to a heteroatomic ligand can be a metal compound complexed to heteroatomic ligand having Structure I, Structure II, Structure III, or any combination thereof. In some embodiments, the metal complex comprising a metal compound complexed to a heteroatomic ligand can be a metal compound complexed to heteroatomic ligand having Structure I; alternatively, Structure II; or alternatively, Structure III. In other embodiments, the metal complex comprising a metal compound complexed to a heteroatomic ligand can be a metal compound complexed to heteroatomic ligand having Structure IV, Structure V, Structure VI, Structure VII, Structure VIII, or any combination thereof. In yet other embodiments, the metal complex comprising a metal compound complexed to a heteroatomic ligand can be a metal compound complexed to heteroatomic ligand having Structure VI; alternatively, Structure VII; or alternatively, Structure VIII.

In an embodiment, the metal complex may be represented by the formula $[R^1R^2P-N(R^5)-PR^3R^4]M-X_p$, wherein $R^1$, $R^2$, $R^3$, and $R^4$ can be any substituent or have any substituent pattern described herein, $R^5$ can be any group as described herein, and $M-X_p$ can be any metal compound as described herein. In some embodiments, the metal complex may be represented by Structure X:

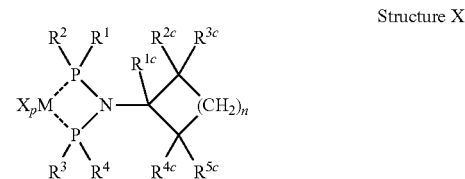

Structure X

Within the metal complex having Structure X embodiments, $R^1$, $R^2$, $R^3$, and $R^4$ can be any substituent or have any substituent pattern described herein for the dialkyl phosphino aminyl moiety, $R^{1c}$, $R^{2c}$, $R^{3c}$, $R^{4c}$, and $R^{5c}$ can be any substituent or have any substituent pattern described herein for the cycloalkyl aminyl nitrogen group, n of the cycloalkyl aminyl nitrogen group can be any value described herein, and $M-X_p$ can be any metal compound described herein. In some embodiments, the metal complex may have Structure XI:

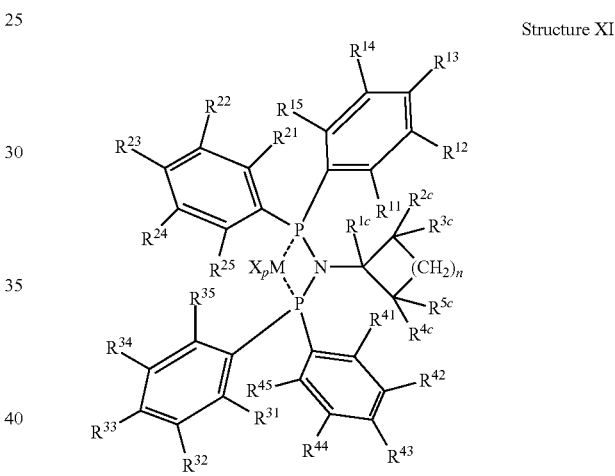

Structure XI

Within the metal complex embodiments having Structure XI, $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ can be any substituent or have any substituent pattern described herein for the diphosphino aminyl moiety, $R^{1c}$, $R^{2c}$, $R^{3c}$, $R^{4c}$, and $R^{5c}$ can be any substituent or have any substituent pattern described herein for the cycloalkyl aminyl nitrogen group, n of the cycloalkyl aminyl nitrogen group can be any value described herein, and $MX_p$ can be any metal compound described herein. In other embodiments, the metal complex may have Structure XII:

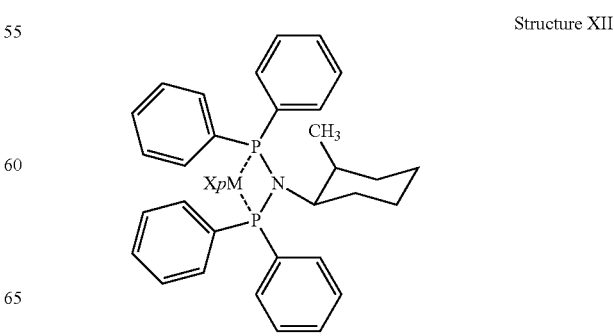

Structure XII

Alternatively, the metal complex can be the product of contacting a metal compound, $M-X_p$, with a heteroatomic ligand comprising multiple diphosphino aminyl moieties, $(PNP)_qL(M-X_p)_q$, wherein PNP represents the diphosphino aminyl moieties, L represents the linking group linking the aminyl nitrogen atoms of the diphosphino aminyl moieties, $M-X_p$ represents the metal compound, and q represents the number of diphosphino aminyl moieties present in the diphosphino aminyl ligand and the number of metal compounds in the metal complex. Generally, the diphosphino moieties, the linking group linking the diphosphino moieties, the metal compound, and q are independent elements. Therefore, the metal complex can be described as a metal compound complexed to a diphosphino aminyl ligand wherein the diphosphino aminyl ligand can have any combination of diphosphino aminyl moieties as described herein, linking group linking the diphosphino aminyl moieties as described herein, and number of diphosphino aminyl moieties, q, as described herein, and the metal compound can be any metal compound as described herein.

Alternatively, a metal complex may be the product of contacting a metal compound, $M-X_p$, with a heteroatomic ligand comprising two diphosphino aminyl moieties and a linking group linking the aminyl nitrogen atoms of the two diphosphino aminyl moieties; $(PNP)_2L(M-X_p)_2$. The resulting metal complex may be dinuclear and have the chemical formula $[R^1R^2P-N(R^5)-PR^3R^4]_2L(M-X_p)_2$. In an embodiment, the metal complex is represented by Structure XIII:

Structure XIII

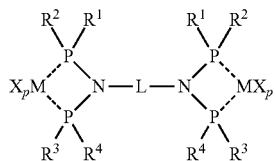

wherein $R^1$, $R^2$, $R^3$, and $R^4$ can be any substituent or have any substituent pattern described herein, L can be any linking group described herein and $M-X_p$ can be any metal compound described herein. In some embodiments, the metal complex is represented by Structure XIV:

wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ can be any substituent or have any substituent pattern described herein, L can be any linking group described herein and $M-X_p$ can be any metal compound described herein. In other embodiments, the metal complex can be represented by Structure XV:

Structure XV

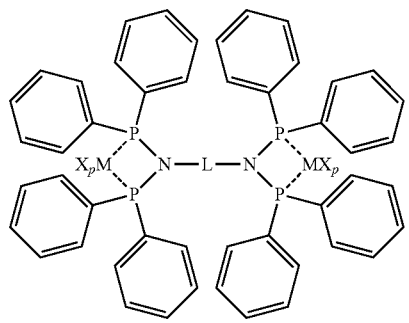

wherein L can be any linking group described herein and $M-X_p$ can be any metal compound described herein, and the undesignated phenyl ring valencies are hydrogen.

In an embodiment, the metal complex can have Structure XVI:

Structure XVI

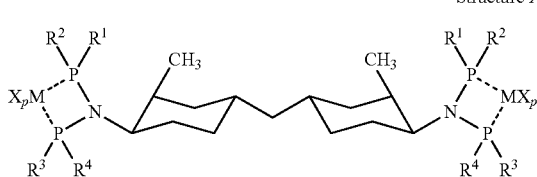

wherein $R^1$, $R^2$, $R^3$, and $R^4$ can be any substituent or have any substituent pattern described herein, $M-X_p$ can be any metal Structure XIV

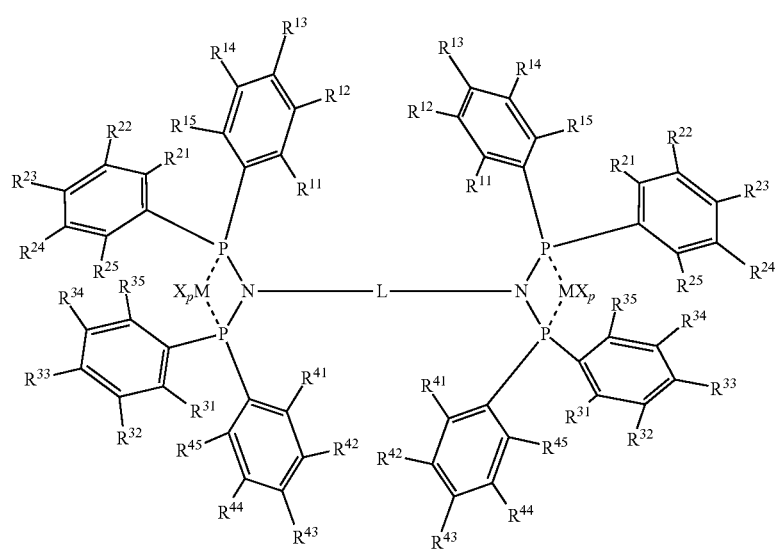

compound described herein, and the undesignated valencies represent hydrogen. In an embodiment, the metal complex can have Structure XVII:

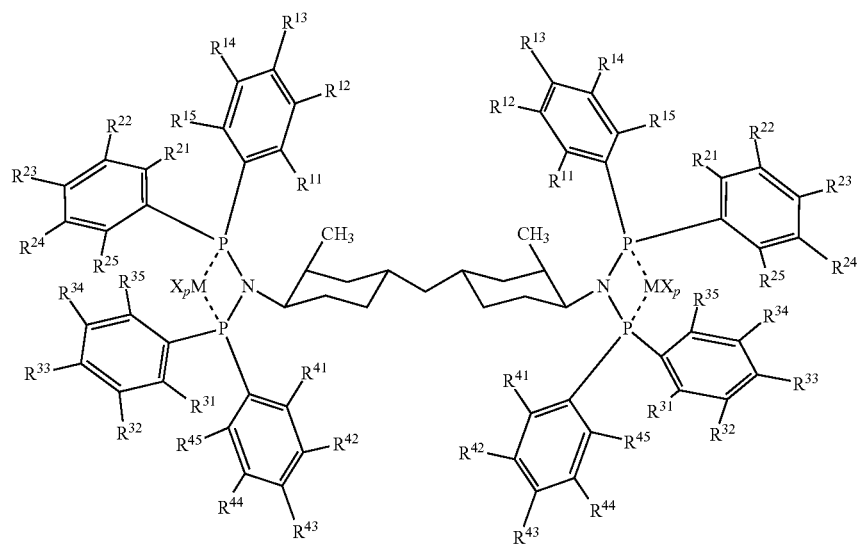

Structure XVII wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ can be any substituent or have any substituent pattern described herein, $M\text{-}X_p$ can be any metal compound described herein and the undesignated valencies represent hydrogen. In an embodiment, the metal complex can have Structure XVIII:

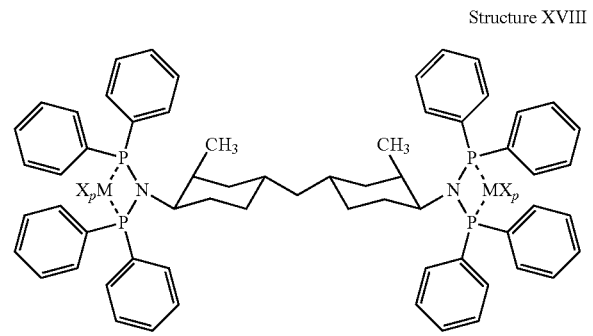

Structure XVIII wherein the undesignated valencies represent hydrogen.

In an embodiment, the metal compound of the metal complex having Structure X, Structure XI, Structure XII, Structure XIII, Structure XIV, Structure XV, Structure XVI, Structure XVII, or Structure XVIII, can comprise titanium, vanadium, or chromium. In an embodiment, the metal compound of the metal complex having Structure X, Structure XI, Structure XII, Structure XIII, Structure XIV, Structure XV, Structure XVI, Structure XVII, or Structure XVIII, comprises chromium. Generally, the chromium compound can have a formula of $CrX_p$, wherein X can be the same or different and can be any organic or inorganic radical, and p may be an integer from 0 to 6. Suitable organic radicals are described herein. In some embodiments, the metal compound of the metal complex having Structure X, Structure XI, Structure XII, Structure XIII, Structure XIV, Structure XV, Structure XVI, Structure XVII, or Structure XVIII can be a chromium halide, a chromium carboxylate, a chromium acetonate, or mixture thereof. In other embodiments, the metal compound of the metal complex having Structure X, Structure XI, Structure XII, Structure XIII, Structure XIV, Structure XV, Structure XVI, Structure XVII, or Structure XVIII can be a chromium halide; alternatively, a chromium carboxylate; or alternatively, a chromium acetonate. Applicable chromium halides, chromium carboxylates, and chromium acetonates are described herein and may generally be utilized as the metal compound of the metal complexes having Structure X, Structure XI, Structure XII, Structure XIII, Structure XIV, Structure XV, Structure XVI, Structure XVII, or Structure XVIII. In some embodiments the chromium compound can be chromium(III) tris(2-ethylhexanoate); or alternatively, chromium (III) acetylacetonate ($Cr(acac)_3$).

One skilled in the art will recognize that metal complex structures formally show a monomeric form of a metal compound complexed to a heteroatomic ligand (or a metal compound complexed to a ligand comprising a diphosphino aminyl moiety). However, it should be noted that these structures do not necessarily imply that dimeric and/or oligomeric forms of Structures having bridging $X_p$ groups which connect metal atoms complexed to the heteroatomic ligand (or the ligand comprising a diphosphino aminyl moiety) are not formed. The monomeric structures provided herein encompass the dimeric and/or oligomeric forms of Structures having bridging $X_p$ groups which connect metal atoms complexed to the heteroatomic ligand (or the ligand comprising a diphosphino aminyl moiety).

In an embodiment, the olefin oligomerization catalyst system comprises a catalyst and a cocatalyst. Generally, the cocatalyst can be any organometallic compound capable of activating the catalyst comprising a metal compound complexed to a heteroatomic ligands described herein to polymerize or oligomerize olefins. Suitable cocatalysts can include monomeric or oligomeric metal alkyls, metal aryls, metal alkyl-aryls comprising at least one of the metals selected from the group consisting of B, Al, Be, Mg, Ca, Sr, Ba, Li, Na, K, Rb, Cs, Zn, Cd, and Sn. In an embodiment, the cocatalyst can be selected from the group consisting of organoaluminum compounds, organoboron compounds, organomagnesium compounds, organozinc compounds, organolithium compounds, or mixtures thereof. In some embodiments, the cocatalyst can be an organoaluminum compound. Applicable organoaluminum compounds can include trialkyl-aluminums, alkylaluminum halides, alumoxanes, or mixtures thereof. In some embodiments, the cocatalyst comprises an alumoxane. In other embodiments, the cocatalyst consists essentially of one or more alumoxanes. In yet other embodiments, the cocatalyst consists of one or more alumoxanes. The metal alkyl can have any number of carbon atoms. However, due to commercial availability and ease of use, the metal alkyl will usually comprise less than about 70 carbon atoms per metal alkyl molecule and alternatively less than about 20 carbon atoms per molecule.

Suitable cocatalysts include, but are not limited to, n-butyllithium, s-butyllithium, t-butyllithium, diethylmagnesium, dibutylmagnesium, diethylzinc, triethylaluminum, trimethylaluminum, tripropylaluminum, tributylaluminum, triisobutylaluminum, tri-n-hexylaluminum, tri-n-octylaluminum, diethylaluminum ethoxide, diethylaluminum phenoxide, ethylaluminum dichloride, diethylaluminum chloride, diethylaluminum bromide, diethylaluminum sesquichloride, diisobutylaluminum chloride, ethylaluminum sesquichloride, diethylaluminum bromide, diethylaluminum iodide, ethylaluminumethoxychloride, and mixtures thereof. In an embodiment, the alkylaluminum compound may be triethylaluminum.

In an embodiment, the cocatalyst may comprise at least one alkylaluminum compound. In some embodiments, the cocatalyst can be a trialkylaluminum compound. Suitable organoaluminum cocatalysts can include, but are not limited to, trimethylaluminum, triethylaluminum, tripropylaluminum, tri-n-butylaluminum, tri-iso-butylaluminum, tri-n-hexylaluminum, tri-n-octylaluminum, diethylaluminumchloride, diethylaluminumbromide, diethylaluminumethoxide, diethylaluminum phenoxide, ethylaluminumethoxychloride, diethylaluminum cyanide, ethylaluminum dichloride, diethylaluminum chloride, diethylaluminum bromide, ethylaluminum sesquichloride, diisobutylaluminum chloride, methylaluminoxane (MAO), modified methylaluminoxane (MMAO), ethylaluminoxanes, isobutyl alumoxanes, t-butyl alumoxanes, and mixtures thereof. In other embodiments, the alumoxane can include methylalumoxane (MAO), modified methylalumoxane (MMAO), isobutyl alumoxanes, t-butyl alumoxanes, or mixtures thereof. In other embodiments, the cocatalyst can comprise methylalumoxane, modified methylalumoxane, or mixtures thereof. In yet other embodiments, the cocatalyst can comprise methylalumoxane; alternatively, modified methylalumoxane; isobutylalumoxane (IBAO); or alternatively, a partially hydrolyzed trialkylaluminum.

Generally, the olefin oligomerization catalyst system comprises an olefin oligomerization catalyst and a cocatalyst. As the olefin oligomerization catalyst and the cocatalyst are independent elements, the olefin oligomerization catalyst system can comprise any combination of the olefin oligomerization catalyst described herein and the cocatalyst as described herein. In some non-limiting embodiments, the olefin oligomerization catalyst is a metal complex comprising a metal compound complexed to a ligand having a diphosphino aminyl moiety (a diphosphino aminyl ligand). In some embodiments, the olefin oligomerization catalyst comprises a metal compound complexed to a diphosphino aminyl ligand comprising multiple diphosphino aminyl moieties. In some embodiments, the olefin oligomerization catalyst comprises a metal compound complexed to a diphosphino aminyl ligand comprising at least 2 diphosphino aminyl moieties; alternatively, with a diphosphino aminyl ligand comprising 2 to 5 diphosphino aminyl moieties; alternatively, with a diphosphino aminyl ligand comprising 2 to 3 diphosphino aminyl moieties; or alternatively, with a diphosphino aminyl ligand comprising only 2 diphosphino aminyl moieties. Further aspects of the diphosphino aminyl ligand are described herein and can be utilized to further describe the diphosphino aminyl ligand utilized as the catalyst used in the olefin oligomerization catalyst system.

Generally, the olefin oligomerization catalyst system can be formed by contacting an olefin oligomerization catalyst and a metal alkyl. In an embodiment, the contacting of the olefin oligomerization catalyst and the metal alkyl can occur in the presence of a solvent. In an embodiment, an olefin oligomerization catalyst system can be formed by contacting an olefin oligomerization catalyst comprising a metal compound complexed to a diphosphino aminyl ligand, and an aluminoxane. In some embodiments, an olefin oligomerization catalyst system is formed by contacting a olefin oligomerization catalyst comprising a chromium compound complexed to a diphosphino aminyl ligand and a metal alkyl; or alternatively, contacting a olefin oligomerization catalyst comprising a chromium compound complexed to a diphosphino aminyl ligand and a metal alkyl in the presence of a solvent. In other embodiments, an olefin oligomerization catalyst system is formed by contacting an olefin oligomerization catalyst comprising a chromium compound complexed to a diphosphino aminyl having at least two diphoshino aminyl ligands (or any other number of diphosphino aminyl ligands disclosed herein) and an alkyl aluminum compound; or alternatively, by contacting an olefin oligomerization catalyst comprising a chromium compound complexed to a ligand having at least two diphosphino aminyl ligands (or any other number of diphosphino aminyl ligands disclosed herein) and an alkyl aluminum compound in the presence of a solvent. In yet other embodiments, an olefin oligomerization catalyst system can be formed by contacting an olefin oligomerization catalyst comprising $Cr(acac)_3$ complexed to a ligand having at least two diphosphino aminyl ligands (or any other number of diphosphino aminyl ligands disclosed herein) and an aluminoxane; or alternatively, by contacting an olefin oligomerization catalyst comprising $Cr(acac)_3$ complexed to a ligand having at least two diphosphino aminyl ligands (or any other number of diphosphino aminyl ligands disclosed herein) and an aluminoxane in the presence of a solvent. Without wishing to be limited by theory, the oligomerization catalyst systems disclosed comprise chromium complexes formed when the heteroatomic ligands coordinate the chromium compounds of this disclosure. Said chromium complexes may comprise the chromium complexed with the heteroatomic ligand and solvent molecules. Such chromium complexes may be further contacted with a cocatalyst such as a metal alkyl to produce olefin oligomerization catalyst systems. The olefin oligomerization catalyst systems may function as the catalyst for the oligomerization of olefins such as the trimerization or tetramerization of ethylene to 1-hexene and 1-octene, respectively.

Generally, the molar ratio of the metal of the cocatalyst and the metal of the catalyst (alternatively, the cocatalyst metal to catalyst metal molar ratio) can be any molar ratio that produces an olefin oligomer product (oligomerized olefin product). In an embodiment, the molar ratio of the metal of the cocatalyst to the metal of the catalyst is greater than 100:1; alternatively, greater than 200:1; alternatively, greater than 300:1; alternatively, greater than 400:1; alternatively greater than 500:1; alternatively, greater than 600:1 or alternatively greater than 700:1. In some embodiments, the molar ratio of the metal of the cocatalyst to the metal of the catalyst can range from 1:1 to 10,000:1; alternatively, from 10:1 to 5,000:1; or alternatively, from 100:1 to 3,000:1; alternatively, from 200:1 to 2,000:1; alternatively, from 400:1 to 1600:1; or alternatively, or alternatively, from 600:1 to 1000:1. In embodiments wherein the metal of the catalyst comprises chromium and the cocatalyst is an alumoxane the molar ratio of aluminum to chromium can range from 1:1 to 10,000:1; alternatively, from 10:1 to 5,000:1; alternatively, from 100:1 to 3,000:1; or alternatively, from 200:1 to 2,000:1.

In an aspect, the catalyst system can further comprise a molar diphosphino aminyl moiety to metal of the metal compound ratio greater than the 1:1 ratio required to form the oligomerization catalyst. This additional diphosphino aminyl moiety can be added during the preparation of the catalyst and/or added during the preparation of the catalyst system (e.g. with the cocatalyst). In an embodiment, the molar diphosphino aminyl moiety to metal of the metal compound ratio in the oligomerization catalyst system is greater than 1.8:1; alternatively, greater than 1.9:1; alternatively, greater than 2.0:1; alternatively, greater than 2.5:1; or alternatively, greater than 3.0:1. In other embodiments, the molar diphosphino aminyl moiety to metal of the metal compound ratio in the catalyst system ranges from 1.8:1 to 10:1; alternatively, ranges from 1.9:1 to 7:1; or alternatively, ranges from 1.95:1 to 5:1.

In some embodiments, the catalyst system can be described as comprising a metal compound, a ligand comprising a diphosphino aminyl moiety, and a cocatalyst. The catalyst system can be further described by the diphosphino aminyl moiety to catalyst metal molar ratio and/or the cocatalyst metal to catalyst metal molar ratio utilized in the catalyst system. Generally, the metal compound, the ligand comprising a diphosphino aminyl moiety, the cocatalyst, the diphosphino aminyl moiety to catalyst metal molar ratio, and the cocatalyst metal to catalyst metal ratio utilized to describe the catalyst system are independent elements of the of catalyst system. Thus, the catalyst system can comprise any combination of metal compound described herein, compound comprising a diphosphino aminyl ligand described herein, cocatalyst described herein, diphosphino aminyl moiety to catalyst metal molar ratio described herein, and/or cocatalyst metal to catalyst molar ratio as described herein.

In a non-limiting embodiment, the catalyst system comprising a metal compound, a ligand comprising a diphosphino aminyl moiety, and a cocatalyst has a diphosphino aminyl moiety to metal of the metal compound molar ratio greater than 1.8:1. In some non-limiting embodiments, the catalyst system has a diphosphino aminyl moiety to metal of the metal compound molar ratio greater than 2.0:1; alternatively, greater than 2.5:1; or alternatively, greater than 3:1. In other non-limiting embodiments, the catalyst system has a diphosphino aminyl moiety to metal of the metal compound molar ratio ranging from 1.8 to 10:1; alternatively, ranging from 2.0:1 to 10:1; alternatively, ranging from 3:1 to 8:1; or alternatively, 4:1 to 6:1. In an embodiment, the metal compound of the catalyst system comprises chromium and the diphosphino aminyl moiety to metal molar ratio can be stated as a diphosphino aminyl moiety to chromium molar ratio.

In a non-limiting embodiment, the catalyst system comprising a metal compound, a ligand comprising a diphosphino aminyl moiety, and a cocatalyst has a diphosphino aminyl moiety to metal of the metal compound molar ratio greater than 1.8:1 and a cocatalyst metal to metal of the metal compound molar ratio greater than 200:1. In some non-limiting embodiments, the catalyst system has a diphosphino aminyl moiety to metal of the metal compound molar ratio greater than 1.8:1 and a cocatalyst metal to metal of the metal compound molar ratio greater than 200:1; alternatively, a diphosphino aminyl moiety to metal of the metal compound molar ratio greater than 2.0:1 and a cocatalyst metal to metal of the metal compound molar ratio greater than 300:1; alternatively, a diphosphino aminyl moiety to metal of the metal compound molar ratio greater than 2.5:1 and a cocatalyst metal to metal of the metal compound molar ratio greater than 400:1; alternatively, a diphosphino aminyl moiety to metal of the metal compound molar ratio ranging from 1.8 to 10:1 and an cocatalyst metal to metal of the metal compound molar ratio ranging from 100:1 to 3,000:1; alternatively, a diphosphino aminyl moiety to metal of the metal compound molar ratio ranging from 2.0:1 to 10:1 and a cocatalyst metal to metal of the metal compound molar ratio ranging from 400:1 to 1600:1; alternatively, a diphosphino aminyl moiety to metal of the metal compound molar ratio ranging from 3:1 to 8:1 and a cocatalyst metal to metal of the metal compound molar ratio ranging from 500:1 to 1,200:1; or alternatively, a diphosphino aminyl moiety to metal of the metal compound molar ratio ranging from 4:1 to 6:1 and a cocatalyst metal to metal of the metal compound molar ratio ranging from 600:1 to 1,000:1. In an embodiment, the metal compound of the catalyst system comprises chromium and the cocatalyst comprises aluminum. In such case, the diphosphino aminyl moiety to metal of the metal compound molar ratio can be stated as a diphosphino aminyl moiety to chromium molar ratio and the cocatalyst metal to metal of the metal compound molar ratio ranging can be stated as an aluminum to chromium molar ratio.

In a non-limiting embodiment, the catalyst system comprises a metal compound comprising chromium, a diphosphino aminyl ligand, and an aluminoxane. In some non-limiting embodiments, the catalyst system comprising a metal compound comprising chromium, a diphosphino aminyl ligand having at least one diphosphino aminyl moiety, and an aluminoxane; alternatively, a metal compound comprising chromium, a diphosphino aminyl ligand comprising at least two diphosphino aminyl moieties and linking group linking the aminyl nitrogen atoms of the aminyl moieties, and an aluminoxane; or alternatively, a metal compound comprising chromium, a diphosphino aminyl ligand comprising only 2 diphosphino aminyl moieties and a linking group linking the aminyl nitrogen atoms of the 2 diphosphino aminyl moieties, and an aluminoxane.

The catalyst components disclosed herein may be contacted to form an olefin oligomerization catalyst system. The amount of each component used to prepare an olefin oligomerization catalyst system can be any amount such that, when combined to form the catalyst system, oligomerization occurs upon contact with one or more olefins. Generally, a molar excess of the metal alkyl cocatalyst is used. Contacting of the catalyst components can be done under any conditions sufficient to thoroughly contact the components. Typically, contacting is performed in an inert atmosphere, such as, for example, nitrogen and/or argon. The reaction temperature for the disclosed methods of making a catalyst for use in oligomerizing an olefin can be any temperature. For ease of operation, ambient temperature can be employed. In order to effectuate a more efficient reaction, temperatures which maintain the reagents in a liquid state or dispersed state are desirable. In an embodiment, the reaction temperature for contacting the metal compound and the diphosphino aminyl ligand, or for contacting the catalyst and the cocatalyst, is maintained at less than about 120° C.; alternatively, less than about 100° C.;

alternatively, less than about 75° C.; alternatively, less than about 50° C.; or alternatively less than about 25° C. The preparation of the olefin oligomerization catalyst system at a low temperature may increase catalyst activity and reduce levels of undesirable co-product polymer.

In the various embodiments disclosed herein, contacting of catalyst components may occur in one or more contact zones. A contact zone is a zone in which the components are commingled and/or combined, and thereby contacted. The contact zone may be disposed in a vessel, e.g. a storage tank, tote, container, mixing vessel, reactor, etc.; a length of pipe, e.g. a tee, inlet, injection port, or header for combining component feed lines into a common line; or any other suitable apparatus for bringing the components into contact. As used herein, the terms contacted and combined refer to any addition sequence, order, or concentration for contacting or combining two or more catalyst components. In some embodiments, contacting of components may occur in one or more upstream contact zone(s) prior to further contacting with other catalyst component(s) in one or more downstream contact zone(s). Where a plurality of contact zones are employed, contacting may occur simultaneously across the contact zones, sequentially across the contact zones, or both, as is suitable for a given embodiment. Contacting may be carried out in a batch or continuous process, as is suitable for a given embodiment.

In embodiments utilizing a vessel for contacting the components, the components may be optionally mixed by a mixer disposed in the vessel and the formed mixture may then be removed for subsequent processing. In embodiments utilizing a tee or other means for combing lines such as a header, an optional in-line mixer may be placed in the commingled catalyst feed line to ensure that adequate contacting of the combined components takes place, and the mixture is thus formed as it passes through the commingled feed line. Where a method of making a catalyst recites contact or combination of catalyst components, such may be carried out by contacting or combining all or a portion of such components in various embodiments.

As used herein, a composition comprising a catalyst component includes the catalyst component alone or in combination with one or more additional compounds, solvents, or both. None, some, or all of the contacting steps may be carried out in the presence of a solvent (sometimes referred to as an optional solvent), which may be introduced to a contact zone via inclusion with one or more compositions comprising a catalyst component or may be introduced separately to a contact zone, for example in a solvent line or as an initial charge to a contact zone.

In an embodiment, water, acidic protons or both may be abated from any or all of the components of the described catalyst system using methods and conditions known to one of ordinary skill in the art. Such methods and conditions are disclosed in detail in U.S. patent application Ser. No. 11/207,232 filed Aug. 19, 2005 and entitled "Methods of Preparation of an Olefin Oligomerization Catalyst" which was previously disclosed herein.

In an embodiment, the olefin oligomerization catalyst system can further comprise a solvent. The solvent may be a hydrocarbon solvent, a halogenated hydrocarbon solvent, or combinations thereof. Generally, the catalyst system solvent or diluent can comprise a $C_4$ to $C_{20}$ hydrocarbon; alternatively, a $C_4$ to $C_{10}$ hydrocarbon; alternatively, $C_1$ to $C_{15}$ halogenated hydrocarbon; or alternatively, $C_1$ to $C_{10}$ halogenated hydrocarbon. The hydrocarbon solvent can be a saturated hydrocarbon, an aromatic hydrocarbon, or an olefinic hydrocarbon. In an embodiment, the saturated hydrocarbon solvent or diluent may comprise butane, isobutane, pentane, n-hexane, hexanes, cyclohexane, n-heptane or n-octane, or mixtures thereof. In some embodiments, the aromatic solvent can be a $C_6$ to $C_{20}$ aromatic compound. Suitable aromatic hydrocarbons can include benzene, toluene, mixed xylenes, ortho-xylene, meta-xylene, para-xylene, ethylbenzene, or mixtures thereof. Suitable halogenated catalyst solvents or diluents can include, carbon tetrachloride, chloroform, methylene chloride, dichloroethane, trichloroethane, chlorobenzene, or dichlorobenzene, or mixtures thereof. In an embodiment, the solvent can be ethylbenzene.

The catalyst and catalyst systems described in the present application can be employed in the oligomerization of olefins. Such a process can be carried out by contacting the catalyst or catalyst system with one or more olefin monomers under reaction conditions suitable for polymerization or oligomerization of olefins. In some embodiments, the oligomerization process comprises: a) contacting an olefin, a metal complex, and a cocatalyst; and b) forming an olefin oligomer product. In other embodiments, the oligomerization process is an ethylene oligomerization process (or alpha olefin production process) comprising: a) contacting ethylene, a metal complex, and a cocatalyst; and b) forming a product stream comprising olefins. In other embodiments, the oligomerization process is an alpha olefin production process comprising: a) contacting ethylene, a metal complex, and a cocatalyst; and b) forming a product stream comprising an alpha olefin. Generally, the metal complex can be any structure provided herein or have any description as described herein. In further embodiments, the oligomerization process comprises: a) contacting an olefin and a catalyst system and b) forming an olefin oligomer product. In other embodiments, the oligomerization process is an ethylene oligomerization process (or alpha olefin production process) comprising: a) contacting ethylene and a catalyst system; and b) forming a product stream comprising olefins. In yet other embodiments, the oligomerization process is an alpha olefin production process comprising: a) contacting ethylene and a catalyst system; and b) forming a product stream comprising an alpha olefin. Generally, the catalyst system may be any catalyst system described herein.

The process can comprise additional steps such as deactivating the catalyst and isolating the olefin oligomer. Suitable monomers for the olefin oligomerization can be olefins having 2 to 20 carbon atoms; alternatively, olefins having 2 to 3 carbon atoms; alternatively, ethylene; or alternatively, propylene. In yet other embodiments, olefin oligomerization process (or the ethylene oligomerization process) further comprises contacting hydrogen with the olefin (or ethylene), the metal complex, and the cocatalyst. In further embodiments, the alpha olefin production process further comprises contacting hydrogen with the ethylene, the metal complex, and the cocatalyst.

In an embodiment, the metal complex utilized in the olefin oligomerization process can have the Structure X:

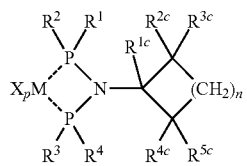

Structure X wherein $R^1$, $R^2$, $R^3$, and $R^4$ can be any substituent described herein or have any substituent pattern described herein for the dialkyl phosphino aminyl moiety, $R^{1c}$, $R^{2c}$, $R^{3c}$, $R^{4c}$, and $R^{5c}$ can be any substituent described herein, have any substituent pattern described herein for the cycloalkyl aminyl nitrogen group, and/or have any substituent pattern necessary to meet a particular aspect of the diphosphino aminyl ligand described herein, n of the cycloalkyl aminyl nitrogen group can be any value described herein, and M-$X_p$ can be any metal compound described herein. In an embodiment, $R^{2c}$ can be any alkyl group described herein, $R^{1c}$, $R^{3c}$, $R^{4c}$, and $R^5$ are hydrogen, and M-$X_p$ comprises chromium. In some embodiments, $R^{2c}$ can be a $C_1$ to $C_4$ alkyl group and $R^{1c}$, $R^{3c}$, $R^{4c}$, and $R^5$ is hydrogen, and M-$X_p$ comprises chromium. In some embodiments, $R^{2c}$ is a methyl group, $R^{1c}$, $R^{3c}$, $R^{4c}$, and $R^5$ are hydrogen, and M-$X_p$ comprises chromium. In other embodiments, the metal complex utilized in the olefin oligomerization process can have the Structure XI:

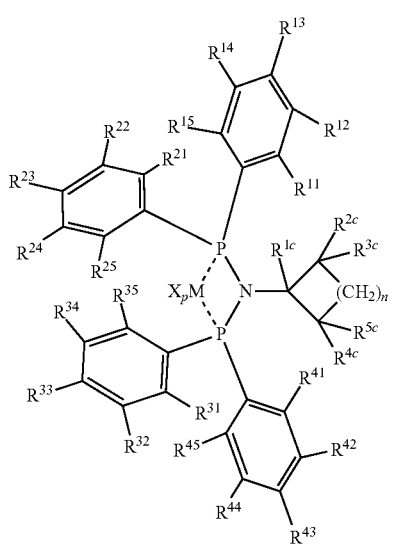

Structure XI wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ can be any substituent described herein or have any substituent pattern described herein for the diphosphino aminyl moiety, $R^{1c}$, $R^{2c}$, $R^{3c}$, $R^{4c}$, and $R^{5c}$ can be any substituent described herein, have any substituent pattern described herein for the cycloalkyl aminyl nitrogen group, and/or have any substituent pattern necessary to meet a particular aspect of the diphosphino aminyl ligand described herein, n of the cycloalkyl aminyl nitrogen group can be any value described herein, and M-$X_p$ can be any metal compound described herein. In an embodiment, $R^{2c}$ can be any alkyl group described herein, $R^{1c}$, $R^{3c}$, $R^{4c}$, and $R^5$ are hydrogen, and M-$X_p$ comprises chromium. In some embodiments, $R^{2c}$ can be a $C_1$ to $C_4$ alkyl group and $R^{1c}$, $R^{3c}$, $R^{4c}$, and $R^5$ is hydrogen, and M-$X_p$ comprises chromium. In some embodiments, $R^{2c}$ is a methyl group, $R^{1c}$, $R^{3c}$, $R^{4c}$, and $R^{5c}$ are hydrogen, and M-$X_p$ comprises chromium. In other embodiments, the metal complex utilized in the olefin oligomerization process can have the Structure XII:

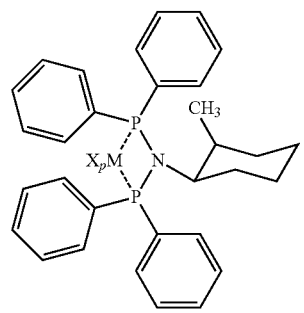

Structure XII wherein M-$X_p$ can be any metal compound described herein. In some embodiments, M-$X_p$ comprises chromium.

In an embodiment, the metal complex utilized in the olefin oligomerization process can comprise a metal compound complexed to a heteroatomic ligand comprising multiple diphosphino aminyl moieties and a linking group linking the aminyl nitrogen atoms of the diphosphino aminyl moieties. Generally, the metal complex described as a metal compound complexed to a heteroatomic ligand comprising multiple diphosphino aminyl moieties and a linking group linking the aminyl nitrogen atoms of the diphosphino aminyl moieties can be any metal compound complexed to a heteroatomic ligand comprising multiple diphosphino aminyl moieties and a linking group linking the aminyl nitrogen atoms of the diphosphino aminyl moieties described herein. In some embodiments, the metal complex utilized in the olefin oligomerization process can comprise a metal compound complexed to a heteroatomic ligand comprising only 2 diphosphino aminyl moieties and a linking group linking the aminyl nitrogen atoms of the two diphosphino aminyl moieties.

In a non-limiting embodiment, the metal complex utilized in the olefin oligomerization process can have the Structure XVI:

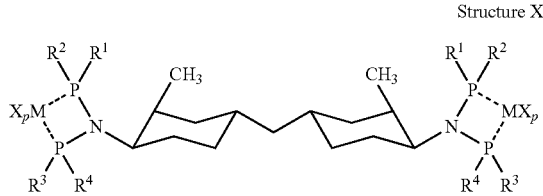

Structure XVI wherein $R^1$, $R^2$, $R^3$, and $R^4$ can be any substituent or have any substituent pattern described herein for the diphosphino aminyl moiety, and M-$X_p$ can be any metal compound described herein. In some embodiments, M-$X_p$ comprises chromium. In other embodiments, the metal complex utilized in the olefin oligomerization process can have the Structure XVII:

Structure XVII

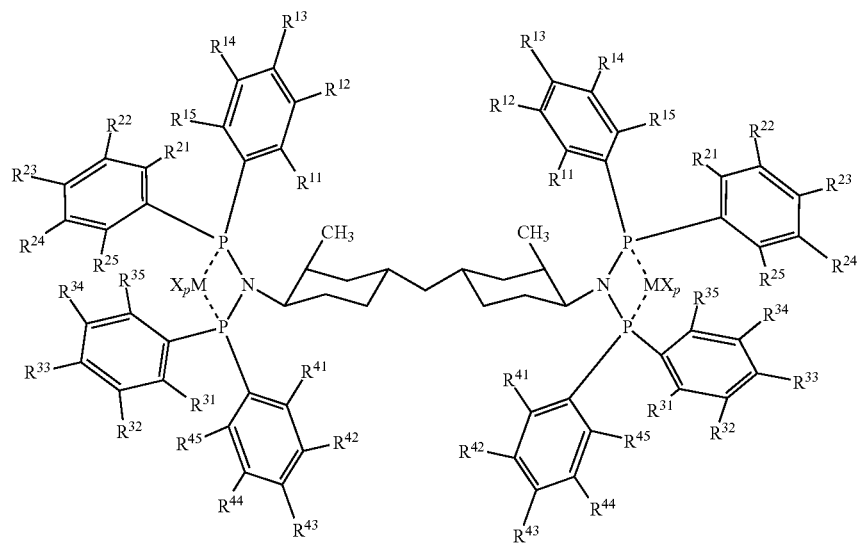

wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ can be any substituent or have any substituent pattern described herein for the diphosphino aminyl moiety, $M\text{-}X_p$ can be any metal compound described herein. In some embodiments, $M\text{-}X_p$ comprises chromium. In yet other embodiments, the metal complex utilized in the olefin oligomerization on process can have the Structure XVIII.

Structure XVIII

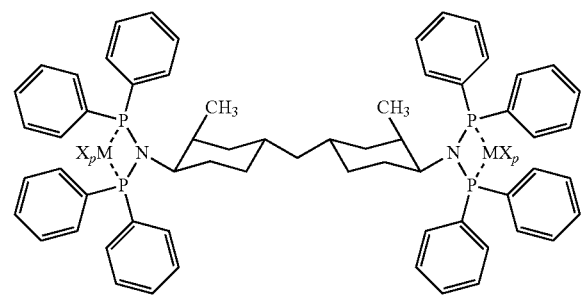

wherein $M\text{-}X_p$ can be any metal compound described herein. In some embodiments, $M\text{-}X_p$ comprises chromium.

In an embodiment, the oligomerization can occur in a solvent or diluent. In some embodiments, the solvent or diluent can comprise a $C_4$ to $C_{20}$ hydrocarbon; or alternatively, a $C_4$ to $C_{10}$ hydrocarbon. The hydrocarbon solvent can be a saturated hydrocarbon, an aromatic hydrocarbon, or mixture thereof. In some embodiments, the saturated hydrocarbon solvent can be a $C_4$ to $C_{10}$ saturated hydrocarbon. In other embodiments, the saturated solvent can be butane, isobutane, pentane, n-hexane, hexanes, heptane, octane, cyclohexane, or mixtures thereof. In some embodiments, the aromatic solvent can be a $C_6$ to $C_{20}$ aromatic compound. In some embodiments, the aromatic solvent can be benzene, toluene, xylene(s), ethylbenzene, or mixtures thereof.

Unless specified otherwise, the terms contacted, combined, and "in the presence of" refer to any addition sequence, order, or concentration for contacting or combining two or more components of the oligomerization process. Combining or contacting of oligomerization components, according to the various methods described herein may occur in one or more contact zones under suitable contact conditions such as temperature, pressure, contact time, flow rates, etc. . . . The contact zone can be disposed in a vessel (e.g. a storage tank, tote, container, mixing vessel, reactor, etc.), a length of pipe (e.g. a tee, inlet, injection port, or header for combining component feed lines into a common line), or any other suitable apparatus for bringing the components into contact. The processes may be carried out in a batch or continuous process as is suitable for a given embodiment, with physical parameters of the contact zone being specified accordingly.

In an embodiment, the oligomerization can be a continuous process carried out in one or more reactors. In some embodiments, the continuous oligomerization process reactor can comprise a loop reactor, a tubular reactor, a continuous stirred tank reactor (CSTR), or combinations thereof. In other embodiments, the continuous oligomerization process reactor can be a loop reactor; alternatively, a tubular reactor; or alternatively, a continuous stirred tank reactor (CSTR). In other embodiments, the continuous polymerization or oligomerization process reactor can be employed in the form of different types of continuous reactors in combination, and in various arrangements.

Suitable oligomerization process conditions such as temperatures, pressures and times can be impacted by a number of factors such as the metal complex stability, metal complex activity, cocatalyst identity, cocatalyst activity, desired product distribution, and/or desired product purity among others. Provided the teachings of the present disclosure, one skilled in the art will recognize how to adjust the oligomerization process conditions to achieve the desired objectives.

The concentration of the diphosphino aminyl complexed metal compound can be any concentration needed to produce the desired oligomerization product. In an embodiment, the concentration of the diphosphino aminyl complexed metal compound is greater than or equal to $5 \times 10^{-6}$ equivalents/liter; alternatively greater than or equal to $1 \times 10^{-5}$ equivalents/liter;

or alternatively, greater than or equal to $2.5 \times 10^{-5}$ equivalents/liter. In other embodiments, the concentration of the diphosphino aminyl complexed metal compound can range from $5 \times 10^{-6}$ to $5 \times 10^{-3}$ equivalents/liter; alternatively, range from $1 \times 10^{-5}$ to $1 \times 10^{-4}$ equivalents/liter; or alternatively, range from $2.5 \times 10^{-5}$ to $6 \times 10^{-5}$ equivalents/liter.

The reaction temperature of the oligomerization temperature can be any reaction temperature required to produce the desired oligomerization product. In some embodiments, the reaction temperature for the oligomerization can range from −20° C. to 200° C. In some embodiments, the oligomerization temperature ranges from 0° C. to 150° C.; alternatively, ranges from 10° C. to 150° C.; alternatively, ranges from 20° C. to 100° C.; or alternatively, ranges from 30° C. to 80° C.

The reaction pressure of the oligomerization can be any reaction pressure required to produce the desired oligomerization product. In some embodiments, the oligomerization pressure can be greater than or equal to 1 psig (6.9 kPa); alternatively, greater than or equal to 50 psig (344 kPa); alternatively, greater than or equal to 100 psig (689 kPa); or alternatively, greater than or equal to 150 psig (1.0 MPa). In other embodiments, the oligomerization pressure can range from 1 psig (6.9 kPa) to 5,000 psig (34.5 MPa); alternatively, 50 psig (344 kPa) to 4,000 psig (27.6 MPa); alternatively, 100 psig (689 kPa) to 3,000 psig (20.9 MPa); or alternatively, 150 psig (1.0 MPa) to 2,000 psig (13.8 MPa). In embodiments wherein the monomer is a gas (e.g. ethylene), the oligomerization can be carried out under a monomer gas pressure. When the oligomerization reaction produces alpha olefins, the reaction pressure can be the monomer ethylene pressure. In some embodiments, the ethylene pressure can be greater than or equal to 1 psig (6.9 kPa); alternatively, greater than or equal to 50 psig (344 kPa); alternatively, greater than or equal to 100 psig (689 kPa); or alternatively, greater than or equal to 150 psig (1.0 MPa). In other embodiments, the ethylene pressure can range from 1 psig (6.9 kPa) to 5,000 psig (34.5 MPa); alternatively, 50 psig (344 kPa) to 4,000 psig (27.6 MPa); alternatively, 100 psig (689 kPa) to 3,000 psig (20.9 MPa); or alternatively, 150 psig (1.0 MPa) to 2,000 psig (13.8 MPa). In some cases when ethylene is the monomer, inert gases can form a portion of the total reaction pressure. In the cases where inert gases form a portion of the reaction pressure, the previously stated ethylene pressures can be the applicable ethylene partial pressures of the oligomerization reaction. In the situation where the monomer provides all or a portion of the oligomerization reaction pressure, the reaction system pressure can decrease as the gaseous monomer is consumed. In this situation, additional gaseous monomer and/or inert gas can be added to maintain a desired oligomerization reaction pressure. In an embodiment, additional gaseous monomer can be added to the oligomerization reaction at a set rate (e.g. for a continuous flow reactor), at different rates (e.g. to maintain a set system pressure in a batch reactor). In other embodiments, the oligomerization reaction pressure can be allowed to decrease without adding any additional gaseous monomer and/or inert gas.

In embodiments wherein hydrogen is contacted with the ethylene, metal complex, and cocatalyst, hydrogen may be added in any amount that produces the desired effect described herein. In some embodiments, the hydrogen partial pressure can be greater than or equal to 1 psig (kPa); alternatively, greater than or equal to 5 psig (34 kPa); alternatively, greater than or equal to 10 psig (69 kPa); or alternatively, greater than or equal to 15 psig (100 kPa). In other embodiments, the hydrogen partial pressure can range from 1 psig (6.9 kPa) to 500 psig (3.5 MPa); alternatively, 5 psig (34 kPa) to 400 psig (2.8 MPa); alternatively, 10 psig (69 kPa) to 300 psig (2.1 MPa); or alternatively, 15 psig (100 kPa) to 200 psig (1.4 MPa).

The reaction time of the oligomerization reaction can be any reaction time required to produce the desired quantity of oligomerization product, obtain a desired catalyst productivity, and/or obtain a desired conversion of monomer. In some embodiments, the polymerization or oligomerization reaction time can range from 1 minute to 8 hours; alternatively, from 5 minutes to 5 hours; alternatively, from 10 minutes to 2.5 hours; or alternatively, from 15 minutes to 2 hours.

In an embodiment, the oligomerization process produces an oligomerization product comprising an olefin trimer, an olefin tetramer, or mixtures thereof. In some embodiments, the olefin production process produces a reactor effluent comprising an ethylene trimer (hexene) and an ethylene tetramer (octene). In other embodiments, an alpha olefin production process produces a reactor effluent comprising 1-hexene and 1-octene. In yet other embodiments, the alpha olefin production process produces a reactor effluent enriched in 1-hexene and 1-octene.

In an embodiment, the liquid oligomerized reactor effluent (or liquid oligomer product, or liquid oligomer product mixture) of the alpha olefin production process comprises greater than or equal to 60 wt. % of an oligomerized product having 6 and 8 carbon atoms (or alternatively, $C_6$ and $C_8$ oligomer product). In some embodiments, the liquid oligomerproduct mixture of the alpha olefin production process comprises greater than or equal to 70 wt. % of an oligomerized product having 6 to 8 carbon atoms; alternatively, greater than or equal to 75 wt. % of an oligomerized product having 6 to 8 carbon atoms; alternatively, greater than or equal to 80 wt. % of an oligomerized product having 6 to 8 carbon atoms; alternatively, greater than or equal to 85 wt. % of an oligomerized product having 6 to 8 carbon atoms; or alternatively, greater than or equal to 90 wt. % of an oligomerized product having 6 to 8 carbon atoms. In other embodiments, the liquid oligomerproduct mixture of the alpha olefin production process comprises from 60 to 99.5 wt. % of an oligomerized product having 6 to 8 carbon atoms; alternatively, from 70 to 99 wt. % of an oligomerized product having 6 to 8 carbon atoms; alternatively, from 75 to 97.5 wt. % of an oligomerized product having 6 to 8 carbon atoms; or alternatively, from 80 to 95 wt. % of an oligomerized product having 6 to 8 carbon atoms. Throughout this application, liquid oligomerized reactor effluent (or liquid oligomer product) refers to the oligomerized product having from 4 to 18 carbon atoms. The liquid oligomerized reactor effluent may also be referred to as a liquid oligomer product or liquid oligomer product mixture.

In an embodiment, the liquid oligomerized reactor effluent (or liquid oligomer product, or liquid oligomerized product mixture) of the alpha olefin production process that comprises greater than or equal to 60 wt. % of an oligomerized product having 6 and 8 carbon atoms, or any other percent of oligomerized product having 6 to 8 carbon atoms described herein, comprises at least 30 wt. % of an oligomerized product having 8 carbon atoms; alternatively, at least 40 wt. % of an oligomerized product having 8 carbon atoms; alternatively, at least 45 wt. % of an oligomerized product having 8 carbon atoms; alternatively, at least 50 wt. % of an oligomerized product having 8 carbon atoms; or alternatively, at least 55 wt. % of an oligomerized product having 8 carbon atoms. In other embodiments, the liquid oligomerized product mixture of the alpha olefin production process that comprises greater than or equal to 60 wt. % of an oligomerized product having 6 and 8 carbon atoms, or any other percent of oligomerized product having 6 to 8 carbon atoms described herein, comprises from 30 to 80 wt % of an oligomerized product having 8 carbon atoms; or alternatively, comprises from 40 to 70 wt % of an oligomerized product having 8 carbon atoms. In yet other embodiments, the liquid oligomerized product mixture of the alpha olefin production process that comprises greater than or equal to 60 wt. % of an oligomerized product having 6 and 8 carbon atoms, or any other percent of oligomerized product having 6 to 8 carbon atoms described herein, has a mass (or weight) ratio of oligomerized product having 8 carbon atoms to oligomerized product having 6 carbon atoms ranging from 0.5 to 2.4; alternatively, from 0.7 to 2.2; or alternatively, from 0.9 to 2.0. The oligomerized product having 8 carbon atoms may also be referred to as a $C_8$ oligomer product. The mass (or weight) ratio of oligomerized product having 8 carbon atoms to oligomerized product having 6 carbon atoms may also be referred to as a mass (or weight) ratio of $C_8$ oligomer product to $C_6$ oligomer product, an oligomerized product $C_8:C_6$ mass (or weight) ratio, or a $C_8:C_6$ oligomer product mass (or weight) ratio.

In an embodiment, the oligomerized product having 6 carbon atoms comprises greater than or equal to 85 wt. % 1-hexene. In some embodiments, the oligomerized product having 6 carbon atoms comprises greater or equal to 87.5 wt. % 1-hexene; alternatively, greater than or equal to 90 wt % 1-hexene; alternatively, greater than or equal to 91 wt. % 1-hexene; or alternatively, greater than or equal to 92 wt. % 1-hexene. In other embodiments, the oligomerized product having 6 carbon atoms comprises from 85 to 99 wt % 1-hexene; alternatively, from 87.5 to 98 wt % 1-hexene; alternatively, from 90 to 97 wt % 1-hexene; alternatively, from 91 to 96 wt % 1-hexene. The oligomerized product having 6 carbon atoms may also be referred to as a $C_6$ oligomer product.

In an embodiment, the oligomerized product having 8 carbon atoms comprises greater than or equal to 97 wt. % 1-octene. In some embodiments, the oligomerized product having 8 carbon atoms comprises greater than or equal to 97.5 wt. % 1-octene; alternatively, greater than or equal to 98 wt % 1-octene; alternatively, greater than or equal to 98.5 wt. % 1-octene; or alternatively, greater than or equal to 99 wt. % 1-octene. In other embodiments, the oligomerized product having 8 carbon atoms comprises from 97 to 99.8 wt % 1-octene; alternatively, from 97.5 to 99.6 wt % 1-octene; alternatively, from 98 to 99.7 wt % 1-octene; alternatively, from 98.5 to 99.5 wt % 1-octene.

In an embodiment, the oligomerized product having 6 carbon atoms comprises greater than or equal to 90 wt. % 1-hexene and the oligomerized product having 8 carbon atoms comprises greater than or equal to 97 wt. % 1-octene. In some embodiments, the oligomerized product having 6 carbon atoms comprises greater than or equal to 91 wt. % 1-hexene and the oligomerized product having 8 carbon atoms comprises greater than or equal to 97.5 wt. % 1-octene. In some embodiments, the oligomerized product having 6 carbon atoms comprises greater than or equal to 92 wt. % 1-hexene and the oligomerized product having 8 carbon atoms comprises greater than or equal to 98 wt. % 1-octene. In other embodiments, the oligomerized product having 6 carbon atoms comprises from 90 to 97 wt. % 1-hexene and the oligomerized product having 8 carbon atoms comprises from 98 to 99.7 wt. % wt. % 1-octene. In yet other embodiments, the oligomerized product having 6 carbon atoms comprises from 91 to 96 wt. % 1-hexene and the oligomerized product having 8 carbon atoms comprises from 98.5 to 99.5 wt. % 1-octene.

In an embodiment, the catalyst comprising a metal compound complexed to a heteroatomic ligand having at least two diphosphino aminyl moieties has an increased oligomerization activity. In some embodiments, the catalyst comprising a metal compound complexed to a heteroatomic ligand comprising at least two diphosphino aminyl moieties has an oligomerization activity greater than the catalyst comprising a metal compound complexed to a heteroatomic ligand having only one diphosphino aminyl moiety, the same diphosphino aminyl moiety, and a similar structure about the diphosphino aminyl moiety's aminyl nitrogen atom. In an embodiment, the catalyst comprising a metal compound complexed to a diphosphino aminyl ligand having two diphosphino aminyl moieties increases the activity by at least 30%; alternatively, 40%; alternatively, 50%; or alternatively, 60%, in comparison to a similar catalyst comprising a metal compound complexed to a diphosphino aminyl ligand having only one diphosphino aminyl moiety, the same diphosphino aminyl moiety, and a similar structure about the diphosphino aminyl moiety's aminyl nitrogen atom.

In an embodiment, the catalyst comprising a metal compound complexed to a heteroatomic ligand having at least two diphosphino aminyl moieties produces a liquid oligomerized reactor effluent having a decreased $C_8:C_6$ oligomerized product ratio (by weight) as compared to the liquid oligomerized reactor effluent produced from a catalyst comprising a metal compound complexed to a heteroatomic ligand having only one diphosphino aminyl moiety, the same diphosphino aminyl moiety, and a similar structure about the diphosphino aminyl moiety's aminyl nitrogen atom. In an embodiment, the catalyst comprising a metal compound complexed to a heteroatomic ligand having at least two diphosphino aminyl moieties produces a liquid oligomerized reactor effluent having an $C_6$ oligomerized product having an increased 1-hexene content as compared to the liquid oligomerized reactor effluent produced from a catalyst comprising a metal compound complexed to a heteroatomic ligand having only one diphosphino aminyl moiety, the same diphosphino aminyl moiety, and a similar structure about the diphosphino aminyl moiety's aminyl nitrogen atom. The term having a similar structure about the diphosphino aminyl moiety's aminyl nitrogen atom refers to the heteroatomic ligand structure within 3 carbon atoms of the aminyl nitrogen. For example, one would compare two metal catalysts having only one tertiary carbon atom adjacent to each carbon atom to which the aminyl nitrogen atom of the diphosphino aminyl moiety is attached, two metal catalysts having the aminyl nitrogen atom of the diphosphino aminyl moiety attached to saturated cyclic ring carbon, or two metal catalysts having the aminyl nitrogen atom of the diphosphino aminyl moiety attached to an aromatic ring carbon.

In an embodiment, the oligomerization process that comprises contacting an olefin, a metal complex, a cocatalyst and hydrogen, has an increased activity as compared to the process carried out in the absence of hydrogen. In some embodiments, the addition of hydrogen to the oligomerization reaction increased the catalyst activity by greater than 25%; alternatively, greater than 40%; alternatively, greater than 65%; or alternatively, greater than 80%.

In an embodiment, the oligomerization process that comprises contacting an olefin, a metal complex, a cocatalyst and hydrogen, produces a liquid oligomerized reactor effluent having a decreased $C_8:C_6$ oligomerized product ratio as compared to the liquid oligomerized reactor effluent produced in the absence of hydrogen. In some embodiments, the addition of hydrogen to the oligomerization reaction decreases the $C_8:C_6$ weight ratio of the oligomerized product by greater than 20%; alternatively, greater than 30%; or alternatively, greater than 40%.

In an embodiment, the oligomerization process that comprises contacting an olefin, a metal complex, a cocatalyst and hydrogen, produces a liquid oligomerized reactor effluent with an oligomerized product having 6 carbon atoms with an increased 1-hexene content as compared to the liquid oligomerized reactor effluent produced in the absence of hydrogen.

In an aspect, the amount of polymer produced by olefin oligomerization process may be reduced by providing and/or controlling one or more olefin production (or oligomerization) parameters. In an embodiment, the amount of polymer produced by the olefin oligomerization process can be reduced by providing and/or controlling a concentration of the diphosphino aminyl complexed metal compound. In some embodiments, the amount of polymer produced by the olefin oligomerization process can be reduced by providing and/or controlling a cocatalyst metal to the catalyst metal molar ratio. In other embodiments, the amount of polymer produced by the olefin oligomerization process can be reduced by providing and/or controlling a diphosphino aminyl moiety to catalyst metal equivalent ratio. In yet other embodiments, the amount of polymer produced by the olefin oligomerization process can be reduced by providing and/or controlling a hydrogen partial pressure during the olefin oligomerization.

In an aspect, the amount of polymer produced in the method to oligomerize olefins can be reduced by providing an increased concentration of diphosphino aminyl complexed metal compound. In an embodiment, the amount of polymer produced can be reduced by providing a concentration of diphosphino aminyl complexed metal compound greater than or equal to $2 \times 10^{-5}$ equivalents/liter; alternatively, greater than or equal to $2.5 \times 10^{-5}$ equivalents/liter; or alternatively, greater than or equal to $2.75 \times 10^{-5}$ equivalents/liter. In some embodiments, the amount of polymer produced by the olefin oligomerization process can be reduced by providing a concentration of diphosphino aminyl complexed metal compound ranging from $2 \times 10^{-5}$ to $1 \times 10^{-4}$ equivalents/liter; alternatively, ranging from $2.5 \times 10^{-5}$ to $8 \times 10^{-4}$ equivalents/liter; or alternatively, ranging from $2.75 \times 10^{-5}$ to $6 \times 10^{-5}$ equivalents/liter.

In an aspect, the amount of polymer produced in the method to oligomerize olefins can be reduced by providing an increased cocatalyst metal to the catalyst metal molar ratio. In an embodiments, the amount of polymer produced can be reduced by providing a cocatalyst metal to the catalyst metal molar ratio greater than or equal to 400:1; alternatively, greater than or equal to 500:1; or alternatively, greater than or equal to 600:1. In some embodiments, the amount of polymer produced can be reduced by providing a cocatalyst metal to the catalyst metal molar ratio ranging from 400:1 to 1600:1; alternatively, ranging from 500:1 to 1200:1; or alternatively, ranging from 600:1 to 1000:1.

In an aspect, the amount of polymer produced in the method to oligomerize olefins can be reduced by providing an increased the diphosphino aminyl moiety to catalyst metal molar ratio. In an embodiment, the amount of polymer produced can be reduced by providing a diphosphino aminyl moiety to catalyst metal molar ratio greater than or equal to 2:1; alternatively, greater than or equal to 3:1; or alternatively, greater than or equal to 4:1. In some embodiments, the amount of polymer produced can be reduced by providing diphosphino aminyl moiety to catalyst metal molar ratio ranging from 2:1 to 10:1; alternatively ranging from 3:1 to 8:1; or alternatively, ranging from 4:1 to 6:1.

In an aspect, the amount of polymer produced in the method to oligomerize olefins can be reduced by providing and/or controlling a partial pressure of hydrogen to the olefin production process. While it should be noted that the presence of hydrogen is not necessarily required to produce an oligomerization product having an acceptable quantity of polymer, the amount of polymer produced by the oligomerization process may be further reduced by the presence of hydrogen. Additionally, it has been observed that the presence of too much hydrogen may increase the quantity of polymer produced. Thus, it has been surprisingly discovered that there is an optimum range for the hydrogen partial pressure. In an embodiment, the amount of polymer produced in the method to oligomerize olefins can be reduced by providing a hydrogen partial pressure ranging from 1 psi (6.9 kPa) to 40 psi (275 kPa); alternatively, from 2.5 psi (17.2 kPa) to 35 psi (241 kPa); or alternatively, range from 5 psi (103 kPa) to 30 psi (206 kPa).

In an embodiment, the amount of polymer produced by the olefin oligomerization process can be reduced by providing and/or controlling an olefin production process parameter selected from the group consisting of a) a concentration of diphosphino aminyl complexed metal compound, b) a cocatalyst metal to the catalyst metal molar ratio, c) a diphosphino aminyl moiety to catalyst metal molar ratio, d) a hydrogen partial pressure during the olefin oligomerization, or any combination of a, b, c, and d thereof. In some embodiments, a method for reducing an amount of polymer produced in an olefin production process comprises a) contacting an olefin, a diphosphino aminyl ligand metal complex, a cocatalyst, and hydrogen, b) providing and/or controlling an olefin production process parameter selected from the group consisting of i) a concentration of diphosphino aminyl complexed metal compound, ii) a cocatalyst metal to the catalyst metal molar ratio, iii) a cocatalyst metal to the catalyst metal molar ratio, iv) a hydrogen partial pressure, or any combination of i, ii, iii, and iv thereof, and c) forming an olefin oligomer product.

The concentration of the diphosphino aminyl complexed metal compound, the cocatalyst metal to catalyst metal molar ratio, the diphosphino aminyl moiety to catalyst metal molar ratio, and hydrogen partial pressure are independent elements of the olefin oligomerization process and thus these elements can have any value (or value range) described herein or have any combination of the individually provided values described herein. In an embodiment, a method for reducing an amount of polymer produced in an olefin production process comprises a) contacting an olefin, a diphosphino aminyl ligand metal complex, a cocatalyst, and hydrogen, b) providing an olefin production process parameter selected from the group consisting of i) a concentration of diphosphino aminyl complexed metal compound greater than $2 \times 10^{-5}$ equivalents/liter, ii) a cocatalyst metal to the catalyst metal molar ratio greater than 400:1, iii) a diphosphino aminyl moiety to catalyst metal molar ratio greater than 2:1, iv) a hydrogen partial pressure ranging from 1 psi (6.9 kPa) to 40 psi (275 kPa), or any combination of i, ii, iii, and iv thereof, and c) forming an olefin oligomer product. In some embodiments, the olefin production process is an alpha olefin production process wherein the olefin is ethylene and the olefin oligomer product comprises alpha olefins.

In an aspect, the amount of polymer produced by the olefin oligomerization process can be reduced by providing and/or controlling the concentration of diphosphino aminyl complexed metal compound and the cocatalyst metal to the catalyst metal molar ratio. Absent changes in other parameters, providing and/or controlling the concentration of diphosphino aminyl complexed metal compound and the cocatalyst metal to catalyst metal molar ratio can produce an oligomerized product having a reduced amount of polymer. The provided concentration of diphosphino aminyl complexed metal compound and the provided cocatalyst metal to catalyst metal molar ratio can have any value (or range) or combination of values (or ranges) individually described herein. Non-limiting combinations include a concentration of diphosphino aminyl complexed metal compound greater than or equal to $2 \times 10^{-5}$ equivalents/liter and a cocatalyst metal to catalyst metal molar ratio greater than or equal to 400:1; alternatively, a concentration of diphosphino aminyl complexed metal compound greater than or equal to $2.5 \times 10^{-5}$ equivalents/liter and a cocatalyst metal to catalyst metal molar ratio greater than or equal to 500:1; or alternatively, a concentration of diphosphino aminyl complexed metal compound greater than or equal to $2.75 \times 10^{-5}$ equivalents/liter and a cocatalyst metal to catalyst metal molar ratio greater than or equal to 600:1. Other non-limiting combinations include a concentration of diphosphino aminyl complexed metal compound ranging from $2 \times 10^{-5}$ to $1 \times 10^{-4}$ equivalents/liter and a cocatalyst metal to catalyst metal molar ratio ranging from 400:1 to 1600:1; alternatively, a concentration of diphosphino aminyl complexed metal compound ranging from $2.5 \times 10^{-5}$ to $8 \times 10^{-4}$ equivalents/liter and a cocatalyst metal to catalyst metal molar ratio ranging from 500:1 to 1200:1; or alternatively, a concentration of diphosphino aminyl complexed metal compound ranging from $2.75 \times 10^{-5}$ to $6 \times 10^{-5}$ equivalents/liter and a cocatalyst metal to catalyst metal molar ratio ranging from 600:1 to 1000:1.

In an embodiment, the amount of polymer produced by the olefin oligomerization process can be reduced by providing and/or controlling the concentration of diphosphino aminyl complexed metal compound and the diphosphino aminyl moiety to catalyst metal molar ratio. Absent changes in other parameters, providing and/or controlling the concentration of diphosphino aminyl complexed metal compound and the diphosphino aminyl moiety to catalyst metal molar ratio can produce an oligomerized product having a reduced amount of polymer. The provided concentration of diphosphino aminyl complexed metal compound and the provided diphosphino aminyl moiety to catalyst metal molar ratio can have any value (or range) or combination of values (or ranges) individually described herein. Non-limiting combinations include a concentration of diphosphino aminyl complexed metal compound greater than or equal to $2 \times 10^{-5}$ equivalents/liter and a diphosphino aminyl moiety to catalyst metal molar ratio greater than or equal to 2:1; alternatively, a concentration of diphosphino aminyl complexed metal compound greater than or equal to $2.5 \times 10^{-5}$ equivalents/liter and a diphosphino aminyl moiety to catalyst metal molar ratio greater than or equal to 3:1; or alternatively, a concentration of diphosphino aminyl complexed metal compound greater than or equal to $2.75 \times 10^{-5}$ equivalents/liter and a diphosphino aminyl moiety to catalyst metal molar ratio greater than or equal to 4:1. Other non-limiting combinations include a concentration of diphosphino aminyl complexed metal compound ranging from $2 \times 10^{-5}$ to $1 \times 10^{-4}$ equivalents/liter and a diphosphino aminyl moiety to catalyst metal molar ratio ranging from 2:1 to 10:1; alternatively, a concentration of diphosphino aminyl complexed metal compound ranging from $2.5 \times 10^{-5}$ to $8 \times 10^{-4}$ equivalents/liter and a diphosphino aminyl moiety to catalyst metal molar ratio ranging from 3:1 to 8:1; or alternatively, a concentration of diphosphino aminyl complexed metal compound ranging from $2.75 \times 10^{-5}$ to $6 \times 10^{-5}$ equivalents/liter and a diphosphino aminyl moiety to catalyst metal molar ratio ranging from 4:1 to 6:1.

In an embodiment, the amount of polymer produced by the olefin oligomerization process can be reduced by providing and/or controlling the cocatalyst metal to the catalyst metal molar ratio and the diphosphino aminyl moiety to catalyst metal molar ratio. Absent changes in other parameters, providing and/or controlling the cocatalyst metal to the catalyst metal molar ratio and the diphosphino aminyl moiety to catalyst metal molar ratio can produce an oligomerized product having a reduced amount of polymer. The provided cocatalyst metal to the catalyst metal molar ratio and the provided diphosphino aminyl moiety to catalyst metal molar ratio can have any value (or range) or combination of values (or ranges) individually described herein. Non-limiting combinations include a cocatalyst metal to the catalyst metal molar ratio greater than or equal to 400:1 and a diphosphino aminyl moiety to catalyst metal molar ratio greater than or equal to 2:1; alternatively, a cocatalyst metal to the catalyst metal molar ratio greater than or equal to 500:1 and a diphosphino aminyl moiety to catalyst metal molar ratio greater than or equal to 3:1; or alternatively, a cocatalyst metal to the catalyst metal molar ratio greater than or equal to 600:1 and a diphosphino aminyl moiety to catalyst metal molar ratio greater than or equal to 4:1. Other non-limiting combinations include a cocatalyst metal to the catalyst metal molar ratio ranging from 400:1 to 1600:1 and a diphosphino aminyl moiety to catalyst metal molar ratio ranging from 2:1 to 10:1; alternatively, a cocatalyst metal to the catalyst metal molar ratio ranging from than 500:1 to 1200:1 and a diphosphino aminyl moiety to catalyst metal molar ratio ranging from 3:1 to 8:1; or alternatively, a cocatalyst metal to the catalyst metal molar ratio ranging from 600:1 to 1000:1 and a diphosphino aminyl moiety to catalyst metal molar ratio ranging from 4:1 to 6:1.

In an embodiment, the amount of polymer produced by the olefin oligomerization process can be reduced by providing and/or controlling the concentration of diphosphino aminyl complexed metal compound, the cocatalyst metal to catalyst metal molar ratio, and the diphosphino aminyl moiety to catalyst metal molar ratio. Absent changes in other parameters, providing and/or controlling the concentration of diphosphino aminyl complexed metal compound, the cocatalyst metal to the catalyst metal molar ratio, and the diphosphino aminyl moiety to catalyst metal molar ratio can produce an oligomerized product having a reduced amount of polymer. The provided concentration of diphosphino aminyl complexed metal compound, the provided cocatalyst metal to the catalyst metal molar ratio, and the provided diphosphino aminyl moiety to catalyst metal molar ratio can have any value (or range) or combination of values (or ranges) individually described herein. Non-limiting combinations include a concentration of diphosphino aminyl complexed metal compound greater than or equal to $2 \times 10^{-5}$ equivalents/liter, a cocatalyst metal to the catalyst metal molar ratio greater than 400:1, and a diphosphino aminyl moiety to catalyst metal molar ratio greater than or equal to 2:1; alternatively, a concentration of diphosphino aminyl complexed metal compound greater than or equal to $2.5 \times 10^{-5}$ equivalents/liter, a cocatalyst metal to the catalyst metal molar ratio greater than or equal to 500:1, and a diphosphino aminyl moiety to catalyst metal molar ratio greater than or equal to 3:1; or alternatively, a concentration of diphosphino aminyl complexed metal compound greater than or equal to $2.75 \times 10^{-5}$ equivalents/liter, a cocatalyst metal to the catalyst metal molar ratio greater than or equal to 600:1, and a diphosphino aminyl moiety to catalyst metal molar ratio greater than or equal to 4:1. Other non-limiting combinations include a concentration of diphosphino aminyl complexed metal compound ranging from $2 \times 10^{-5}$ to $1 \times 10^4$ equivalents/liter, a cocatalyst metal to the catalyst metal molar ratio ranging from 400:1 to 1600:1, and a diphosphino aminyl moiety to catalyst metal molar ratio ranging from 2:1 to 10:1; alternatively, a concentration of diphosphino aminyl complexed metal compound ranging from $2.5 \times 10^{-5}$ to $8 \times 10^{-4}$ equivalents/liter, a cocatalyst metal to the catalyst metal molar ratio ranging from 500:1 to 1200:1, and a diphosphino aminyl moiety to catalyst metal molar ratio ranging from 3:1 to 8:1; or alternatively, a concentration of diphosphino aminyl complexed metal compound ranging from $2.75 \times 10^{-5}$ to $6 \times 10^{-5}$ equivalents/liter, a cocatalyst metal to the catalyst metal molar ratio ranging from 600:1 to 1000:1, and a diphosphino aminyl moiety to catalyst metal molar ratio ranging from 4:1 to 6:1.

In an embodiment, the amount of polymer produced by the olefin oligomerization process can be reduced by providing and/or controlling the cocatalyst metal to the catalyst metal molar ratio, the diphosphino aminyl moiety to catalyst metal molar ratio, and the hydrogen partial pressure. Absent changes in other parameters, providing and/or controlling the cocatalyst metal to the catalyst metal molar ratio, the diphosphino aminyl moiety to catalyst metal molar ratio, and the hydrogen partial pressure, can produce an oligomerized product having a reduced amount of polymer. The provided cocatalyst metal to the catalyst metal molar ratio, the provided diphosphino aminyl moiety to catalyst metal molar ratio, and the provided hydrogen partial pressure can have any value (or range) of combination of values (or ranges) individually described herein. Non-limiting combinations include a cocatalyst metal to the catalyst metal molar ratio greater than or equal to 400:1, a diphosphino aminyl moiety to catalyst metal molar ratio greater than or equal to 2:1, and a hydrogen partial pressure ranging from 1 psi (6.9 kPa) to 40 psi (275 kPa); alternatively, a cocatalyst metal to the catalyst metal molar ratio greater than or equal to 500:1, a diphosphino aminyl moiety to catalyst metal molar ratio greater than or equal to 3:1, and a hydrogen partial pressure ranging from 2.5 psi (17.2 kPa) to 35 psi (241 kPa); or alternatively, a cocatalyst metal to the catalyst metal molar ratio greater than or equal to 600:1, a diphosphino aminyl moiety to catalyst metal molar ratio greater than or equal to 4:1, and a hydrogen partial pressure ranging from 5 psi (103 kPa) to 30 psi (206 kPa). Other non-limiting combinations include a cocatalyst metal to the catalyst metal molar ratio ranging from 400:1 to 1600:1, a diphosphino aminyl moiety to catalyst metal molar ratio ranging from 2:1 to 10:1, and a hydrogen partial pressure ranging from 1 psi (6.9 kPa) to 40 psi (275 kPa); alternatively, a cocatalyst metal to the catalyst metal molar ratio ranging from 500:1 to 1200:1, a diphosphino aminyl moiety to catalyst metal molar ratio ranging from 3:1 to 8:1, and a hydrogen partial pressure ranging from 2.5 psi (17.2 kPa) to 35 psi (241 kPa); or alternatively, a cocatalyst metal to the catalyst metal molar ratio ranging from 600:1 to 1000:1, a diphosphino aminyl moiety to catalyst metal molar ratio ranging from 4:1 to 6:1, and a hydrogen partial pressure ranging from 5 psi (103 kPa) to 30 psi (206 kPa).

In an embodiment, the amount of polymer produced by the olefin oligomerization process can be reduced by providing and/or controlling the concentration of diphosphino aminyl complexed metal compound, the cocatalyst metal to the catalyst metal molar ratio, the diphosphino aminyl moiety to catalyst metal molar ratio, and the hydrogen partial pressure during the olefin oligomerization. Absent changes in other parameters, providing and/or controlling the concentration of diphosphino aminyl complexed metal compound, the cocatalyst metal to the catalyst metal molar ratio, the diphosphino aminyl moiety to catalyst metal molar ratio, and the hydrogen partial pressure can produce an oligomerized product having a reduced the amount of polymer. The provided concentration of diphosphino aminyl complexed metal compound, the provided cocatalyst metal to the catalyst metal molar ratio, the provided diphosphino aminyl moiety to catalyst metal molar ratio, and the provided hydrogen partial pressure can have any value (or range) or combination of values (or ranges) individually described herein. Non-limiting combinations include having a concentration of diphosphino aminyl complexed metal compound greater than or equal to $2 \times 10^{-5}$ equivalents/liter, having a cocatalyst metal to the catalyst metal molar ratio greater than or equal to 400:1, having a diphosphino aminyl moiety to catalyst metal molar ratio greater than or equal to 2:1, and having a hydrogen partial pressure ranging from 1 psi (6.9 kPa) to 40 psi (275 kPa); alternatively, having a concentration of diphosphino aminyl complexed metal compound greater than or equal to $2.5 \times 10^{-5}$ equivalents/liter, having a cocatalyst metal to the catalyst metal molar ratio greater than or equal to 500:1, having a diphosphino aminyl moiety to catalyst metal molar ratio greater than or equal to 3:1, and having a hydrogen partial pressure ranging from 2.5 psi (17.2 kPa) to 35 psi (241 kPa); or alternatively, having a concentration of diphosphino aminyl complexed metal compound greater than or equal to $2.75 \times 10^{-5}$ equivalents/liter, having a cocatalyst metal to the catalyst metal molar ratio greater than or equal to 600:1, having a diphosphino aminyl moiety to catalyst metal molar ratio greater than or equal to 4:1, and having a hydrogen partial pressure ranging from 5 psi (103 kPa) to 30 psi (206 kPa). Other non-limiting combinations include having a concentration of diphosphino aminyl complexed metal compound ranging from $2 \times 10^{-5}$ to $1 \times 10^{-4}$ equivalents/liter, having a cocatalyst metal to the catalyst metal molar ratio ranging from 400:1 to 1600:1, having a diphosphino aminyl moiety to catalyst metal molar ratio ranging from 2:1 to 10:1, and having a hydrogen partial pressure ranging from 1 psi (6.9 kPa) to 40 psi (275 kPa); alternatively, having a concentration of diphosphino aminyl complexed metal compound ranging from $2.5 \times 10^{-5}$ to $8 \times 10^{-4}$ equivalents/liter, having a cocatalyst metal to the catalyst metal molar ratio ranging from 500:1 to 1200:1, having a diphosphino aminyl moiety to catalyst metal molar ratio ranging from 3:1 to 8:1, and having a hydrogen partial pressure ranging from 2.5 psi (17.2 kPa) to 35 psi (241 kPa); or alternatively, having a concentration of diphosphino aminyl complexed metal compound ranging from $2.75 \times 10^{-5}$ to $6 \times 10^{-5}$ equivalents/liter, having a cocatalyst metal to the catalyst metal molar ratio ranging from 600:1 to 1000:1, a having diphosphino aminyl moiety to catalyst metal molar ratio ranging from 4:1 to 6:1, and a having hydrogen partial pressure ranging from 5 psi (103 kPa) to 30 psi (206 kPa).

In an embodiment, the amount of polymer produced by providing and/or controlling the concentration of diphosphino aminyl complexed metal compound in the olefin oligomerization process as described herein, the cocatalyst metal to the catalyst metal molar ratio as described herein, the diphosphino aminyl moiety to catalyst metal molar ratio as described herein, and/or the hydrogen partial pressure as described herein, is less than 10 weight percent. Alternatively, the amount of polymer produced by providing and/or controlling the concentration of diphosphino aminyl complexed metal compound in the olefin oligomerization process as described herein, the cocatalyst metal to the catalyst metal molar ratio as described herein, the diphosphino aminyl moiety to catalyst metal molar ratio as described herein, and/or the hydrogen partial pressure as described herein, is less than 7.5 weight percent; alternatively, less than 5 weight percent; alternatively, less than 2.5 weight percent; alternatively less than 1 weight percent; alternatively, less than 0.75 weight percent; or alternatively less than 0.5 weight percent.

EXAMPLES

The invention having been generally described, the following examples are given as particular embodiments of the invention and to demonstrate the practice and advantages thereof. It is understood that the examples are given by way of illustration and are not intended to limit the specification of the claims in any manner.

Example 1

In the example runs below, a standard solution of the ligand, typically having a concentration of approximately 10 mg/ml, was prepared by dissolving/suspending the ligand in a solvent (typically ethylbenzene). A standard solution of the chromium compound, typically having a concentration of 5 mg/ml, was prepared by dissolving/suspending the chromium compound in a solvent (typically ethylbenzene).

The catalyst was prepared by transferring the appropriate amount of ligand and chromium solutions into a thin-walled glass vial (e.g. and NMR tube). The thin-walled glass vial was tightly capped and then strapped to the impeller shaft of a Zipperclave™ reactor. The reactor was sealed and then air was removed from the reactor interior by multiple successive vacuum evacuations and charging with nitrogen. After the successive vacuum evacuations of the reactor interior, a final vacuum was left on the reactor. Under static vacuum, the reaction solvent containing the appropriate quantity of cocatalyst was charged to the reactor through a reactor charging port. Ethylene was then charged to the reactor to a pressure approximately equal to 50 percent of the desired reaction pressure. Stirring was initiated to break the glass vial strapped to the reactor impeller shaft and initiate the reaction. Upon stabilization of the reactor pressure due to dissolution of ethylene into the liquid phase, the desired quantity of hydrogen, if any, was added to the reactor to obtain the desired hydrogen partial pressure. The reactor was heated to the desired reaction temperature. The ethylene pressure was then increased to the desired pressure. Ethylene was then subsequently fed to the reactor on demand to maintain the desired ethylene pressure for the remainder of the reaction. The reaction temperature was maintained by the appropriate use of heating coils and internal cooling coils. Upon reaction completion, the reactor was depressurized and the product isolated. The reaction products were then analyzed by gas chromatography (GC) using an internal standard such as the reaction solvent or an inert hydrocarbon (e.g. nonane).

The product samples were analyzed by the GC for the amount of hexene, octene, and $C_6$ isomers, $C_8$ isomers, and higher oligomers. From this information the selectivity, purity, and conversion was calculated. Selectivity, $(C_6+C_8)$ wt. %, refers to the weight percent of oligomerized product having 6 and 8 carbon atoms found in the liquid oligomerization product. Purity, $(1-C_6+1-C_8)$ wt. % of all liquids), refers to the weight percent of 1-hexene and 1-octene found in the liquid oligomerization product. Activity can be stated as the grams product (liquid oligomerization product, oligomerized product having 6 carbon atoms, oligomerized product having 8 carbon atoms, oligomerized product having 6 and 8 carbon atoms, grams 1-hexene, grams 1-octene, grams 1-hexene+1-octene or any combination or ratio thereof etc. . . . ) produced per gram of catalyst or catalyst component (grams metal, gram ligand, gram cocatalyst, grams cocatalyst metal). Details of the specific reactions conditions and product formation are given in Table 2 where the reaction carried out in the presence of a metal compound complexed to a diphosphino aminyl ligand having one diphosphino aminyl moiety are given in columns 1, 4, 5 and 8 while those carried out in the presence of a metal compound complexed to a diphosphino aminyl ligand having 2 diphosphino aminyl moieties are given in columns 2, 3, 6 and 7. MMAO refers to the cocatalyst (modified methylaluminoxane) and the metal compound is chromium (III) acetylacetonate also referred to as $Cr(acac)_3$. Runs 1-8

Experimental runs 1-8 provide information relating to olefin production using metal catalyst comprising a metal compound complexed to a ligand comprising a diphosphino aminyl ligand.

TABLE 2

Olefin Oligomerization Runs 1-8

| | Run # | | | | | | | |
|---|---|---|---|---|---|---|---|---|
| | 1 | 2 | 3 | 4 | 5 | 6 | 7 | 8 |
| Ligand Structure | III | VIII | VIII | III | III | VIII | VIII | III |
| Metal Compound | Cr(acac)$_3$ | Cr(acac)$_3$ | Cr(acac)$_3$ | Cr(acac)$_3$ | Cr(acac)$_3$ | Cr(acac)$_3$ | Cr(acac)$_3$ | Cr(acac)$_3$ |
| Cocatalyst | MMAO | MMAO | MMAO | MMAO | MMAO | MMAO | MMAO | MMAO |
| Diphosphino aminyl moiety (mg) | 18 | 24 | 24 | 20 | 20 | 18 | 12 | 16 |
| Diphosphino aminyl moiety (meq) | 0.0374 | 0.0493 | 0.0493 | 0.0416 | 0.0416 | 0.037 | 0.0246 | 0.0333 |
| Metal Compound (mg) | 10 | 10 | 10 | 10 | 10 | 7.5 | 5 | 7.5 |
| Metal Compound (mmol) | 0.029 | 0.029 | 0.029 | 0.029 | 0.029 | 0.021 | 0.014 | 0.021 |
| Al:Cr molar ratio | 500 | 500 | 300 | 300 | 300 | 300 | 300 | 300 |
| Temperature (° C.) | 60 | 60 | 60 | 60 | 60 | 60 | 60 | 60 |
| Ethylene Pressure (MPa) | 6.89 | 6.89 | 6.89 | 6.89 | 6.89 | 6.89 | 6.89 | 6.89 |
| H$_2$ Pressure (kPa) | | | | | 345 | 345 | 345 | 345 |
| Reaction time (minutes) | 90 | 60 | 90 | 90 | 90 | 90 | 90 | 90 |
| Liquid product - calc'd (grams) | 482.88 | 719.72 | 659.39 | 392.14 | 687.95 | 898.16 | 711.45 | 550.23 |
| g liquid product/g Cr | 324390 | 483497 | 442969 | 263433 | 462150 | 804494 | 955877 | 492849 |
| g liquid product/g ligand | 26827 | 29988 | 27475 | 19607 | 34397 | 49898 | 59287 | 34390 |
| g liquid product/g Al | 1250 | 1863 | 2845 | 1692 | 2968 | 5163 | 6139 | 3163 |
| (C$_6$ + C$_8$) of all liquids (wt. %) | 91.3 | 89.3 | 88.9 | 92.8 | 88 | 85.7 | 84.8 | 90.7 |
| (1-C$_6$ + 1-C$_8$) of all liquids (wt. %) | 88.2 | 86.6 | 86 | 89.3 | 85.2 | 82.8 | 82.1 | 87.1 |
| C$_8$/C$_6$ mass ratio | 2.61 | 1.81 | 1.85 | 2.73 | 2.02 | 1.07 | 0.97 | 1.87 |
| 1-hexene in C6 fraction (%) | 87.95 | 91.63 | 90.71 | 85.75 | 90.19 | 92.94 | 93.66 | 88.74 |
| 1-octene in C8 fraction (%) | 99.3 | 99.19 | 98.68 | 98.29 | 98.82 | 97.8 | 98.45 | 98.68 |

The examples show an increased catalyst activity for a catalyst comprising a metal compound complexed to a diphosphino aminyl ligand having two diphosphino aminyl moieties. For example, Run 2 carried out with a catalyst comprising a metal compound complexed to a diphosphino aminyl ligand having two diphosphino aminyl moieties has an activity (grams liquid oligomerization product/gram chromium) approximately 50% greater than a Run 1 carried out with a catalyst comprising a metal compound complexed to a diphosphino aminyl ligand having only one diphosphino aminyl moiety, the same diphosphino aminyl moiety, and a similar structure about the diphosphino aminyl moiety's aminyl nitrogen atom. Similarly, Run 6 carried out with a catalyst comprising a metal compound complexed to a diphosphino aminyl ligand having two diphosphino aminyl moieties has an activity (grams liquid oligomerization product/gram chromium) approximately 60 to 75% greater than a Run 5 or Run 8 carried out with a catalyst comprising a metal compound complexed to a diphosphino aminyl ligand having only one diphosphino aminyl moiety, the same diphosphino aminyl moiety, and a similar structure about the diphosphino aminyl moiety's aminyl nitrogen atom.

A comparison of Run 4 to Runs 5 or 8, and/or a comparison of Runs 2 or 3 to Runs 6 or 7 demonstrate that the addition of hydrogen to the oligomerization reaction increases the activity of the catalyst comprising a metal compound complexed to a ligand comprising a diphosphino aminyl moiety. Furthermore, a comparison of Run 4 to Runs 5 or 8, and/or a comparison of Runs 2 or 3 to Runs 6 or 7 demonstrate that the addition of hydrogen to the oligomerization reaction produces an oligomerization product having a lower $C_8$:$C_6$ weight ratio. Furthermore, a comparison of Run 4 to Runs 5 or 8, and/or a comparison of Runs 2 or 3 to Runs 6 or 7 demonstrate that the addition of hydrogen to the oligomerization reaction produces an olefin oligomer having 6 carbon atoms with an increased 1-hexene content.

The examples indicate that the oligomerization catalyst comprising a metal compound complexed to a diphosphino aminyl ligand having two diphosphino aminyl moieties has an increased activity as compared to the catalyst comprising a metal compound complexed to a diphosphino aminyl ligand having only one diphosphino aminyl moiety, the same diphosphino aminyl moiety, and a similar structure about the diphosphino aminyl moiety's aminyl nitrogen atom. The examples further indicated that the oligomerization catalyst comprising a metal compound complexed to a diphosphino aminyl ligand having two diphosphino aminyl moiety produces a reactor effluent comprising a lower $C_8$:$C_6$ oligomerized product ratio (by weight) than a catalyst comprising a metal compound complexed to a diphosphino aminyl ligand having only one diphosphino aminyl moiety, the same diphosphino aminyl moiety and a similar structure about the diphosphino aminyl moiety's aminyl nitrogen atom. The examples further indicated that the oligomerization catalyst comprising a metal compound complexed to a diphosphino aminyl ligand having two diphosphino aminyl moiety produces a reactor effluent having an $C_6$ oligomerized product having an increased 1-hexene content as compared to a catalyst comprising a metal compound complexed to a diphosphino aminyl ligand having the same diphosphino aminyl moiety and a similar structure about the diphosphino aminyl moiety's aminyl nitrogen atom.

Runs 9-24

Experimental runs 9-24 provide information relating to the effect(s) that the concentration of diphosphino aminyl complexed metal compound, the cocatalyst metal to the catalyst metal molar ratio, the diphosphino aminyl moiety to catalyst metal molar ratio, and/or the hydrogen partial pressure during the olefin oligomerization has on the olefin oligomer product (e.g. the amount of polymer produced) produced by the olefin production process comprising a) contacting an olefin, a diphosphino aminyl ligand metal complex, a cocatalyst, and hydrogen, and b) forming olefin oligomers.

TABLE 3

Olefin Oligomerization Runs 9-16

| | Run # | | | | | | | |
|---|---|---|---|---|---|---|---|---|
| | 9 | 10 | 11 | 12 | 13 | 14 | 15 | 16 |
| Ligand Structure | VIII | VIII | VIII | VIII | VIII | VIII | VIII | VIII |
| Metal Compound | Cr(acac)$_3$ | Cr(acac)$_3$ | Cr(acac)$_3$ | Cr(acac)$_3$ | Cr(acac)$_3$ | Cr(acac)$_3$ | Cr(acac)$_3$ | Cr(acac)$_3$ |
| Cocatalyst | MMAO | MMAO | MMAO | MMAO | MMAO | MMAO | MMAO | MMAO |
| Diphosphino aminyl moiety (mg) | 18 | 24 | 30 | 15 | 15 | 15 | 15 | 15 |
| Diphosphino aminyl moiety (meq) | 0.037 | 0.049 | 0.062 | 0.031 | 0.031 | 0.031 | 0.031 | 0.031 |
| Metal Compound (mg) | 3.75 | 5.00 | 6.25 | 3.13 | 3.13 | 3.13 | 3.13 | 3.13 |
| Metal Compound (mmol) | 0.011 | 0.014 | 0.018 | 0.009 | 0.009 | 0.009 | 0.009 | 0.009 |
| Bulk solvent (cyclohexane), (ml) | 400 | 400 | 400 | 400 | 400 | 400 | 400 | 400 |
| Chromium Concentration (M) | 2.68E−05 | 3.58E−05 | 4.47E−05 | 2.24E−05 | 2.24E−05 | 2.24E−05 | 2.24E−05 | 2.24E−05 |
| Al:Cr molar ratio | 400 | 400 | 400 | 800 | 670 | 400 | 800 | 800 |
| Diphosphino aminyl moiety/Cr equivalent molar ratio | 3.443 | 3.443 | 3.443 | 3.443 | 3.443 | 3.443 | 3.443 | 3.443 |
| Temperature (° C.) | 60 | 60 | 60 | 60 | 60 | 60 | 60 | 60 |
| Ethylene Pressure (MPa) | 6.89 | 6.89 | 6.89 | 6.89 | 6.89 | 6.89 | 6.89 | 6.89 |
| H$_2$ pressure (kPa) | 345 | 345 | 345 | 345 | 345 | 345 | 0 | 68.9 |
| Reaction time (minutes) | 90 | 90 | 90 | 90 | 90 | 90 | 90 | 90 |
| Liquid Product (grams) | 675 | 708 | 712 | 781 | 755 | n.d. | 533 | 522 |
| Polymer (grams) | 190 | 330 | 54 | 31 | 45 | 223 | 21 | 17 |
| Polymer (wt. %) | 22.0 | 31.8 | 7.1 | 3.9 | 5.6 | 90.0 | 3.8 | 3.1 |
| g liquid product/g Cr | 1208477 | 950794 | 765015 | 1679554 | 1622710 | n.d. | 1145391 | 1123079 |
| g product/g Cr | 1548847 | 1394171 | 822573 | 1747054 | 1719447 | n.d. | 1190535 | 1158549 |
| g product/g Cr/hr | 1032565 | 929447 | 548382 | 1164703 | 1146298 | n.d. | 793690 | 772366 |
| g liquid product/g ligand | 37477 | 29486 | 23725 | 52086 | 50323 | n.d. | 35521 | 34829 |
| g product/g ligand | 48033 | 43236 | 25510 | 54180 | 53323 | n.d. | 36921 | 35929 |
| ($C_6$ + $C_8$) of all products (wt. %) | 68.5 | 59.7 | 82.5 | 83.7 | 83.5 | n.d. | 87.6 | 88.1 |
| $C_8$/$C_6$ mass ratio | 1.23 | 0.99 | 1.33 | 1.44 | 1.20 | n.d. | 2.13 | 2.03 |

TABLE 3-continued

Olefin Oligomerization Runs 9-16

| | Run # | | | | | | | |
|---|---|---|---|---|---|---|---|---|
| | 9 | 10 | 11 | 12 | 13 | 14 | 15 | 16 |
| 1-hexene in $C_6$ fraction (wt. %) | 93.2 | 93.8 | 93.0 | 93.0 | 93.4 | n.d. | 90.3 | 91.2 |
| 1-octene in $C_8$ fraction (wt. %) | 98.8 | 98.5 | 99.0 | 99.0 | 98.8 | n.d. | 99.5 | 99.4 |
| Liquid Product Carbon Number Distribution (wt %) | | | | | | | | |
| $C_4$ | 0.6 | 0.6 | 0.6 | 0.5 | 0.6 | n.d. | 0.4 | 0.5 |
| $C_6$ | 38.6 | 43.2 | 37.4 | 35.0 | 39.4 | n.d. | 28.3 | 28.9 |
| $C_8$ | 47.4 | 42.6 | 49.6 | 50.4 | 47.4 | n.d. | 60.2 | 58.5 |
| $C_{10}$ | 3.9 | 4.4 | 3.3 | 3.6 | 3.8 | n.d. | 2.0 | 2.1 |
| $C_{12}$ | 4.8 | 4.7 | 4.5 | 5.4 | 5.0 | n.d. | 3.5 | 3.5 |
| $C_{14-18}$ | 2.7 | 2.6 | 2.6 | 3.1 | 2.0 | n.d. | 2.8 | 2.7 |

TABLE 4

Olefin Oligomerization Runs 17-23

| | Run # | | | | | | |
|---|---|---|---|---|---|---|---|
| | 17 | 18 | 19 | 20 | 21 | 22 | 23 |
| Ligand Structure | VIII | VIII | VIII | VIII | VIII | VIII | III |
| Metal Compound | $Cr(acac)_3$ | $Cr(acac)_3$ | $Cr(acac)_3$ | $Cr(acac)_3$ | $Cr(acac)_3$ | $Cr(acac)_3$ | $Cr(acac)_3$ |
| Cocatalyst | MMAO | MMAO | MMAO | MMAO | MMAO | MMAO | MMAO |
| Diphosphino aminyl moiety (mg) | 15 | 20 | 10 | 15 | 30 | 40 | 40 |
| Diphosphino aminyl moiety (meq) | 0.031 | 0.041 | 0.021 | 0.031 | 0.062 | 0.082 | 0.082 |
| Metal Compound (mg) | 3.13 | 3.13 | 3.13 | 3.13 | 6.25 | 6.25 | 6.25 |
| Metal Compound (mmol) | 0.009 | 0.009 | 0.009 | 0.009 | 0.018 | 0.018 | 0.018 |
| Bulk solvent (cyclohexane), (ml) | 400 | 400 | 400 | 400 | 600 | 600 | 600 |
| Chromium Concentration (M) | 2.24E−05 | 2.24E−05 | 2.24E−05 | 2.24E−05 | 2.98E−05 | 2.98E−05 | 2.98E−05 |
| Al:Cr molar ratio | 800 | 800 | 800 | 800 | 800 | 800 | 800 |
| Diphosphino aminy moiety/Cr equivalent molar ratio | 3.443 | 4.591 | 2.295 | 3.443 | 3.443 | 4.591 | 4.591 |
| Temperature (° C.) | 60 | 60 | 60 | 60 | 60 | 60 | 60 |
| Ethylene Pressure (MPa) | 6.89 | 6.89 | 6.89 | 6.89 | 6.89 | 6.89 | 6.89 |
| $H_2$ pressure (kPa) | 172 | 172 | 172 | 172 | 172 | 172 | 172 |
| Reaction time (minutes) | 90 | 90 | 90 | 120 | 90 | 120 | 120 |
| Liquid Product (grams) | 698 | 644 | 811 | 754 | 1214 | 1060 | 1596 |
| Polymer (grams) | 19 | 12 | 48 | 72 | 26 | 6 | 5 |
| Polymer (wt. %) | 2.6 | 1.7 | 5.6 | 8.7 | 2.1 | 0.6 | 0.3 |
| g liquid product/g Cr | 1500361 | 1384767 | 1743615 | 1621599 | 1304515 | 1139594 | 1715836 |
| g product/g Cr | 1541604 | 1410348 | 1846801 | 1775303 | 1332677 | 1146259 | 1721210 |
| g product/g Cr/hr | 1027736 | 940232 | 1231200 | 887652 | 888451 | 573129 | 860605 |
| g liquid product/g ligand | 46529 | 32208 | 81109 | 50289 | 40456 | 26506 | 39909 |
| g product/g ligand | 47808 | 32803 | 85909 | 55056 | 41329 | 26661 | 40034 |
| ($C_6$ + $C_8$) of all products (wt. %) | 86.2 | 87.6 | 82.6 | 79.9 | 89.0 | 86.3 | 87.1 |
| $C_8/C_6$ mass ratio | 1.63 | 1.63 | 1.46 | 1.51 | 1.92 | 1.59 | 2.39 |
| 1-hexene in $C_6$ fraction (wt. %) | 92.5 | 92.6 | 92.6 | 92.7 | 91.6 | 93.0 | 87.8 |
| 1-octene in $C_8$ fraction (wt. %) | 99.3 | 99.3 | 99.3 | 99.2 | 99.1 | 99.4 | 99.4 |
| Liquid Product Carbon Number Distribution (wt %) | | | | | | | |
| $C_4$ | 0.5 | 0.4 | 0.4 | 0.5 | 0.4 | 0.3 | 0.6 |
| $C_6$ | 33.2 | 33.1 | 35.0 | 34.2 | 30.8 | 33.1 | 25.5 |
| $C_8$ | 53.6 | 53.9 | 51.0 | 51.6 | 59.0 | 52.5 | 61.0 |
| $C_{10}$ | 3.0 | 2.8 | 3.5 | 3.4 | 2.2 | 3.3 | 2.3 |
| $C_{12}$ | 4.8 | 4.6 | 5.3 | 5.2 | 4.0 | 6.0 | 5.2 |
| $C_{14-18}$ | 2.9 | 2.8 | 3.1 | 3.1 | 2.4 | 3.4 | 4.4 |

Without further elaboration, it is believed that one skilled in the art can, using the description herein, utilize the present invention to its fullest extent. While preferred embodiments of the invention have been shown and described, modifications thereof can be made by one skilled in the art without departing from the spirit and teachings of the invention. The embodiments and examples described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc.

should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent that they provide exemplary, procedural or other details supplementary to those set forth herein.

What is claimed is:

1. An oligomerization process comprising: a) contacting an olefin, hydrogen and a catalyst system comprising a metal compound, a ligand comprising a diphosphino aminyl moiety, and a cocatalyst; and b) forming an olefin oligomer product, wherein the ligand comprising the diphosphino aminyl moiety is represented by the general structure:

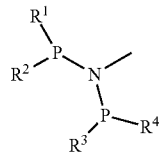

wherein $R^1$, $R^2$, $R^3$, and $R^4$ may each independently be an alkyl group, a cycloalkyl group, a substituted cycloalkyl group, an aromatic group, or a substituted aromatic group and wherein the substituents on the substituted cycloalkyl group and/or substituted aromatic group comprise an alkyl group.

2. The process of claim 1, further comprising providing a process parameter selected from the group consisting of a) a concentration of diphosphino aminyl complexed metal compound greater than $2 \times 10^{-5}$ equivalents/liter or equal to, b) a cocatalyst metal to metal of the metal compound molar ratio greater than or equal to 400:1, c) a diphosphino aminyl moiety to metal of the metal compound molar ratio greater than or equal to 2:1, d) a hydrogen partial pressure ranging from 1 psi (6.9 kPa) to 40 psi (275 kPa), or any combination of a, b, c, and d thereof.

3. The process of claim 1, wherein the catalyst system oligomerization activity is increased as compared to the oligomerization process performed in the absence of hydrogen.

4. The process of claim 1, wherein the olefin oligomer product has a lower $C_8:C_6$ oligomer product weight ratio as compared to the oligomerization process performed in the absence of hydrogen.

5. The process of claim 1, wherein an $C_6$ olefin oligomer product has an increased 1-hexene content as compared to the oligomerization process performed in the absence of hydrogen.

6. The process of claim 1, wherein the ligand comprising the diphosphino aminyl moiety comprises at least one tertiary carbon atom adjacent to a carbon atom to which the aminyl nitrogen atom of the diphosphino aminyl moiety is attached.

7. The process of claim 1, wherein the ligand comprising a diphosphino aminyl moiety has Structure I:

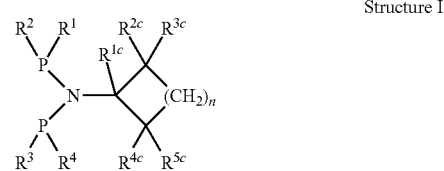

Structure I wherein $R^1$, $R^2$, $R^3$, and $R^4$ are each independently an alkyl group, a cycloalkyl group, a substituted cycloalkyl group, an aromatic group, or a substituted aromatic group, $R^{1c}$, $R^{2c}$, $R^{3c}$, $R^{4c}$, and $R^{5c}$ are each independently hydrogen or an alkyl group, and n ranges from 2 to 4; and wherein the metal compound, comprises a group IVB, VB, or VIB metal.

8. The process of claim 7, wherein the ligand comprising a diphosphino aminyl moiety has Structure II:

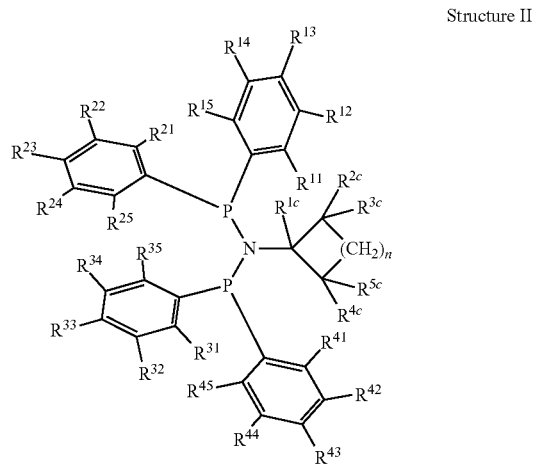

Structure II $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are each independently, hydrogen, or an alkyl group.

9. The process of claim 7, wherein the ligand comprising a diphosphino aminyl moiety has Structure III:

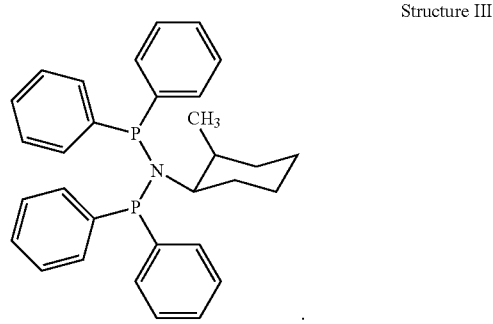

Structure III

10. The process of claim 7, wherein metal compound comprises chromium, titanium, or vanadium.

11. The process of claim 7, wherein the metal compound has the formula $MX_p$ where M is chromium, p is 2 or 3, and each X is a $C_1$ to $C_{20}$ carboxylate, acetonate, alkoxide, or phenoxide.

12. The process of claim 7, wherein the metal compound is chromium (III) acetylacetonate.

13. The process of claim 1, wherein the ligand comprising a diphosphino aminyl moiety comprises at least two diphosphino aminyl moieties and a linking group linking each aminyl nitrogen atom of the diphosphino aminyl moieties; and wherein the metal compound comprises a group IVB, VB, or VIB metal.

14. An oligomerization process comprising: a) contacting an olefin, hydrogen and a catalyst system comprising a metal compound, a ligand comprising a diphosphino aminyl moiety, and a cocatalyst; and b) forming an olefin oligomer product, wherein the ligand comprising a diphosphino aminyl moiety comprises at least two diphosphino aminyl moieties and a linking group linking each aminyl nitrogen atom of the diphosphino aminyl moieties, wherein the metal compound comprises a group IVB, VB, or VIB metal, and wherein the ligand comprising a diphosphino aminyl moiety has Structure VII:

Structure VII

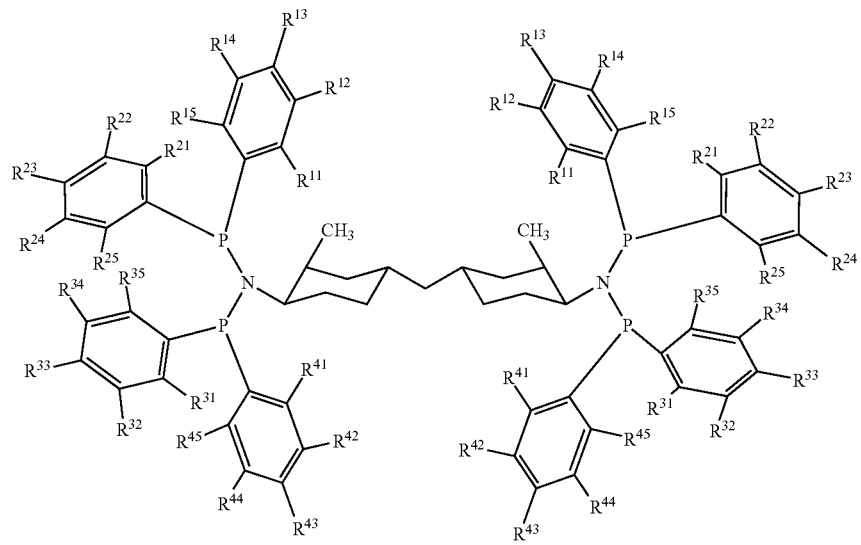

wherein $R^{11}$, $R^{12}$, $R^{13}$, $R^{14}$, $R^{15}$, $R^{21}$, $R^{22}$, $R^{23}$, $R^{24}$, $R^{25}$, $R^{31}$, $R^{32}$, $R^{33}$, $R^{34}$, $R^{35}$, $R^{41}$, $R^{42}$, $R^{43}$, $R^{44}$, and $R^{45}$ are each independently hydrogen, an alkyl group, an alkoxy group, or a halogen atom.

15. An oligomerization process comprising: a) contacting an olefin, hydrogen and a catalyst system comprising a metal compound, a ligand comprising a diphosphino aminyl moiety, and a cocatalyst; and b) forming an olefin oligomer product, wherein the ligand comprising a diphosphino aminyl moiety comprises at least two diphosphino aminyl moieties and a linking group linking each aminyl nitrogen atom of the diphosphino aminyl moieties, wherein the metal compound comprises a group IVB, VB, or VIB metal, and wherein the ligand comprising a diphosphino aminyl moiety has Structure VIII:

Structure VIII

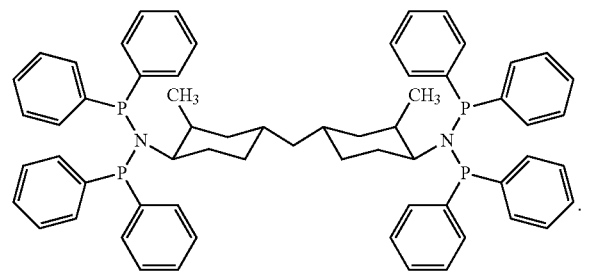

16. The process of claim 13, wherein metal compound comprises chromium, titanium, or vanadium.

17. The process of claim 13, wherein the metal compound has the formula $MX_p$ where M is chromium, p is 2 or 3, and each X is a $C_1$ to $C_{20}$ carboxylate, acetonate, alkoxide, or phenoxide.

18. The process of claim 13, wherein the metal compound is chromium (III) acetylacetonate.

19. A process for reducing an amount of polymer produced in an olefin production process comprising:

a) contacting an olefin, hydrogen, and a catalyst system comprising a metal compound, a ligand comprising a diphosphino aminyl moiety, and a cocatalyst, wherein the ligand comprising the diphosphino aminyl moiety is represented by the general structure:

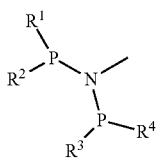

wherein $R^1$, $R^2$, $R^3$, and $R^4$ may each independently be an alkyl group, a cycloalkyl group, a substituted cycloalkyl group, an aromatic group, or a substituted aromatic group and wherein the substituents on the substituted cycloalkyl group and/or substituted aromatic group comprise an alkyl group;

b) providing an olefin production process parameter selected from the group consisting of i) a concentration of diphosphino aminyl complexed metal compound greater than or equal to $2 \times 10^{-5}$ equivalents/liter, ii) a cocatalyst metal to metal of the metal compound molar ratio greater than or equal to 400:1, iii) a diphosphino aminyl moiety to metal of the metal compound molar ratio greater than or equal to 2:1, iv) a hydrogen partial pressure ranging from 1 psi (6.9 kPa) to 40 psi (275 kPa), or any combination of i, ii, iii, and iv thereof: and c) forming an olefin oligomer product.

20. The process of claim 19, wherein the metal compound comprises a group IVB, VB, or VIB metal and the diphosphino aminyl ligand comprises at least two diphosphino aminyl moieties and a linking group linking the aminyl nitrogen atoms of the diphosphino aminyl moieties.

21. The process of claim 19, wherein the diphosphino aminyl ligand has Structure I:

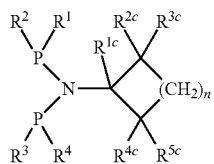

Structure I wherein $R^1$, $R^2$, $R^3$, and $R^4$ are each independently an alkyl group, a cycloalkyl group, a substituted cycloalkyl group, an aromatic group, or a substituted aromatic group, $R^{1c}$, $R^{2c}$, $R^{3c}$, $R^{4c}$, and $R^{5c}$ are each independently hydrogen or an alkyl group, and n ranges from 2 to 4; and wherein the metal compound comprises a group IVB, VB, or VIB metal.

* * * * *